US008510125B2

(12) United States Patent
Sasai et al.

(10) Patent No.: US 8,510,125 B2
(45) Date of Patent: Aug. 13, 2013

(54) DATABASE SYSTEM, PROGRAM, AND INFORMATION PROCESSING METHOD

(75) Inventors: Kosuke Sasai, Kobe (JP); Akane Hashiya, Habikino (JP); Masumi Azuma, Osaka (JP); Kyoko Ishigaki, Kobe (JP); Hiroshi Inada, Toynaka (JP)

(73) Assignees: Konica Minolta Medical & Graphic, Inc., Kobe-Shi (JP); Hyogo Prefecture, Kobe-Shi (JP)

( * ) Notice: Subject to any disclaimer, the term of this patent is extended or adjusted under 35 U.S.C. 154(b) by 1206 days.

(21) Appl. No.: 11/974,968

(22) Filed: Oct. 16, 2007

(65) Prior Publication Data

US 2008/0097795 A1    Apr. 24, 2008

(30) Foreign Application Priority Data

Oct. 18, 2006  (JP) ................................ 2006-284053

(51) Int. Cl.
*G06F 19/00* (2011.01)
*G06Q 10/00* (2012.01)

(52) U.S. Cl.
USPC .................................................. 705/2; 705/3

(58) Field of Classification Search
USPC ..................................................... 705/2, 3, 4
See application file for complete search history.

(56) References Cited

U.S. PATENT DOCUMENTS

2002/0032583 A1*   3/2002   Joao ................................ 705/2

FOREIGN PATENT DOCUMENTS

| JP | 07-056947 | 3/1995 |
|---|---|---|
| JP | 2001-282538 | 10/2001 |
| JP | 2002-342491 | 11/2002 |
| JP | 2003-022325 | 1/2003 |
| JP | 2004-118566 | 4/2004 |
| JP | 2004-133774 | 4/2004 |

* cited by examiner

*Primary Examiner* — Sean K Hunter
(74) *Attorney, Agent, or Firm* — Brinks Hofer Gilson & Lione

(57) ABSTRACT

A disease-symptom-combination DB storing information obtained by combining each of disease name elements indicative of diseases with one or more symptom elements each indicative of a symptom, and a disease-care-combination DB storing information obtained by combining each of the disease name elements with a plurality of care elements each indicative of a care are stored in a storing unit. A server control unit recognizes one or more symptom elements from the symptom information and detects one disease name element combined with all of the symptom elements from the disease-symptom-combination DB. Further, a plurality of care elements combined with the one disease name element are detected from the disease-care-combination DB. Disease care information obtained by combining the one disease name element with the plurality of care elements is generated and visibly output in a display unit.

26 Claims, 54 Drawing Sheets

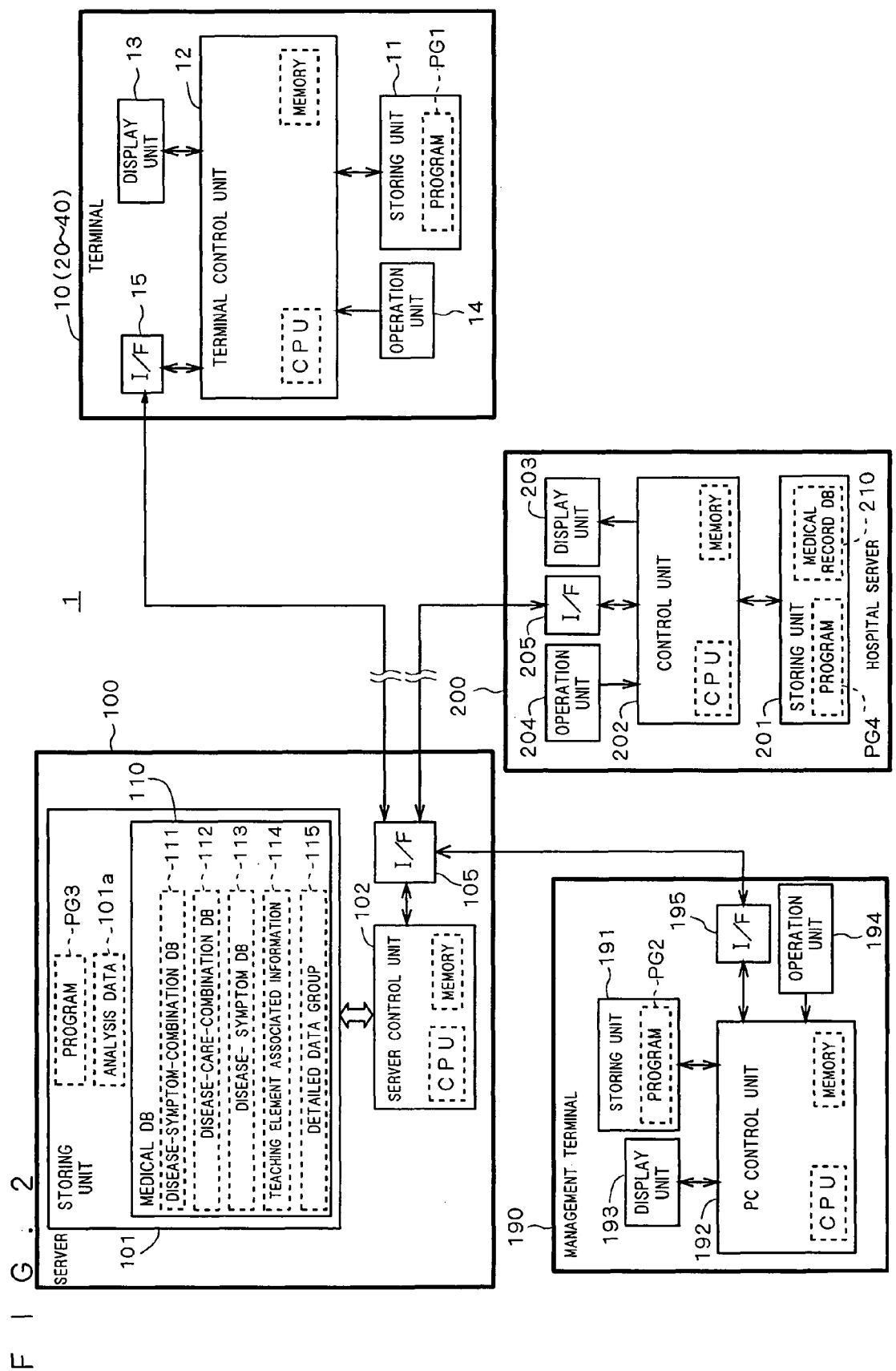

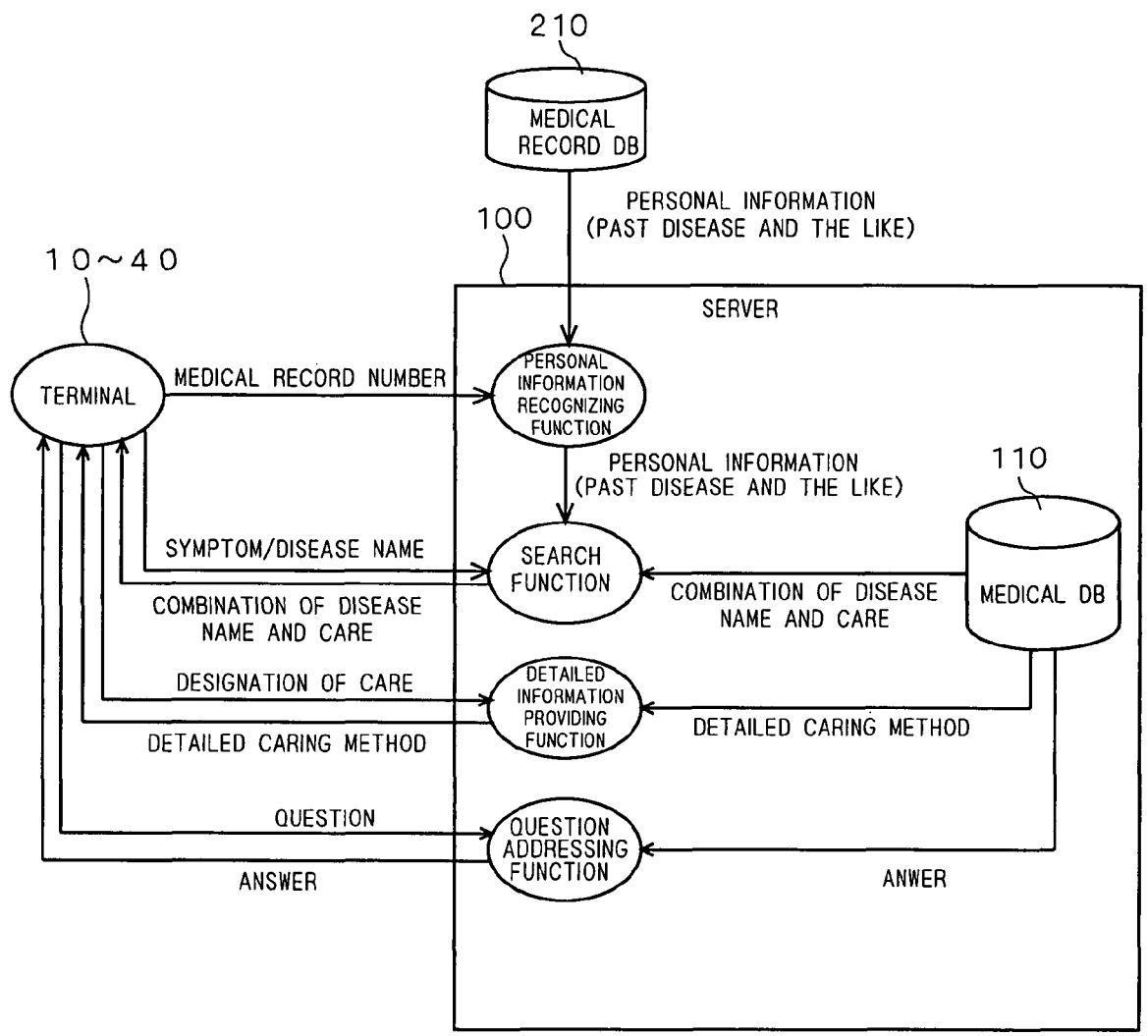

F I G. 4

| | REGION | MAIN SYMPTOM | DETAILED DATA 1 | DETAILED DATA 2 | DETAILED DATA 3 | DETAILED DATA 4 |
|---|---|---|---|---|---|---|
| 1 | CONSTITUTIONAL SYMPTOM | FEVER | HIGH FEVER | SHORT TIME | | |
| 2 | | | | LONG TIME | | |
| 3 | | | MEDIUM FEVER | SHORT TIME | | |
| 4 | | | | LONG TIME | | |
| 5 | | | SLIGHT FEVER | SHORT TIME | | |
| 6 | | | | LONG TIME | | |
| 7 | | FATIGUE | | | | |
| 8 | | CHILL AND RIGOR | | | | |
| 9 | | SWEATING | PALM | | | |
| 10 | | LYMPHADENOPATHY | | | | |
| 11 | | CYANOSIS | LIPS OF MOUTH, PALM | | | |
| 12 | HEAD | HEADACHE | | | | |
| 13 | | INSOMNIA | | | | |
| 14 | BONES AND MUSCLES | JOINT PAIN AND MUSCLE PAIN | | | | |
| 15 | NOSE | RUNNY NOSE | | | | |
| 16 | | COUGHING | | | | |
| 17 | | EXPECTORATION | PURULENT SPUTUM | | | |
| 18 | THROAT | SORE THROAT | DURING SWALLOWING | SOMETIMES RADIATION TO EARS | | |
| 19 | | SNEEZE | | | | |
| 20 | | DYSPNEA | | | | |
| 21 | | RASH | | | | |
| 22 | MOUTH | | KOPLIK'S SPOTS | | | |
| 23 | | JAUNDICE | | | | |
| 24 | | | | | | |
| 25 | SKIN | RASH | REAR SIDE OF EARS, FACE, TOP → BODY TRUNK AND FOUR LIMBS | IRREGULAR SHAPE | A FEW mm TO 1 cm | RED SPOT / SPOTTY |
| 26 | | | FACE → SPREAD TO BODY TRUNK AND FOUR LIMBS | | 2 mm TO 5 mm | MACULOPAPULE |

F I G. 5

| | REGION | MAIN SYMPTOM | DETAILED DATA 1 | DETAILED DATA 2 | DETAILED DATA 3 | DETAILED DATA 4 |
|---|---|---|---|---|---|---|
| 27 | EXCRETION | DIARRHEA | MUCOUS TO WATERY/BLOODY STOOL | | | |
| 28 | | | AQUEOUS ROT SMELL TO BLOODY STOOL | | | |
| 29 | | CONSTIPATION | | | | |
| 30 | | NAUSEA AND VOMITING | | | | |
| 31 | | URINARY DISTURBANCE | URINARY BLADDER STIMULATION SYMPTOM (MICTION PAIN AND FREQUENT URINATION) | | | |
| 32 | | | PYURIA | | | |
| 33 | ABDOMEN | ABDOMINAL PAIN | | | | |
| 34 | | | UMBILICAL REGION PAIN | | | |
| 35 | | | PAIN IN RIGHT LOWER PART OF ABDOMEN | | | |
| 36 | | | CENTER OF UNDERBELLY | | | |
| 37 | | | LEFT LOWER PART OF ABDOMEN | | | |
| 38 | | | RIGHT UPPER PART OF ABDOMEN | COLICKY PAIN | | INTENSE PAIN |
| 39 | | | LEFT UPPER PART OF ABDOMEN | | | |
| 40 | | | EPIGASTRIUM | | | |
| 41 | | | EPIGASTRIC REGION PAIN | COLICKY PAIN | | |
| 42 | | | LATERAL REGION OF ABDOMEN | DULL PAIN | | |
| 43 | | LOSS OF APPETITE | | | | |
| 44 | EYES | HYPEREMIA | TUNICA CONJUNCTIVA BULBI | | | |

FIG. 6

| | COLD | INFLUENZA | ADENOIDITIS | PNEUMONIA | MEASLES | RUBELLA | APPENDICITIS | ACUTE CHOLECYSTITIS | ACUTE CHOLANGITIS | HEPATITIS B | ACUTE PYELONEPHRITIS | SALMONELLOSIS | CAMPYLOBACTER INFECTION |
|---|---|---|---|---|---|---|---|---|---|---|---|---|---|
| 1 | | ⊚ | ⊚ | | ○ | | | | ⊚ | | ⊚ | | |
| 2 | ○ | | | ⊚ | | | | | | | | | |
| 3 | ○ | ○ | ○ | ○ | ○ | ○ | ⊚ | ○ | ○ | ○ | ○ | ○ | ○ |
| 4 | ○ | ○ | | | | | | | | | | | |
| 5 | ○ | ⊚ | | | | ⊚ | ○ | ⊚ | | ⊚ | | ⊚ | ⊚ |
| 6 | ○ | | | ○ | | | | | | | | | |
| 7 | ○ | ○ | | ○ ○ | | ○ | | | | ⊚ | | | ○ ○ |
| 8 | ○ | | | | | | ○ | | ○ | | | | |
| 9 | ○ | | | | | | | | | | | | |
| 10 | ○ | | | | | ○ | | | | | | | |
| 11 | | | | ○ ○ | | | | | | ○ | | | ○ |
| 12 | ○ | ○ | ○ | | | | | | | | | | |
| 13 | | | | | | | | | | | | | |
| 14 | | ⊚ | | | | ○ | | | | | | | |
| 15 | ○ | ○ ○ | | | ○ | ○ | | | | | | | |
| 16 | ○ | ○ | | ○ | ○ | ○ | | | | | | | |
| 17 | ○ | | | | | | | | | | | | |
| 18 | | ○ | ⊚ | ⊚ | | ○ | | | | | | | |
| 19 | ○ | | | ○ | | | | | | | | | |
| 20 | ○ | | ⊚ | ○ | | | | | | | | | |
| 21 | | | | | ○ | | | | | | | | |
| 22 | ○ | | | | | | | | | | | | |
| 23 | | | | | ● | | | | | | | | |
| 24 | | | | | | | | | ⊚ | ⊚ | | | |
| 25 | | | | | ○ | | | | | | | | |
| 26 | | | | | | ⊚ | | | | | | | |

FIG. 7

| | COLD | INFLUENZA | ADENOIDITIS | PNEUMONIA | MEASLES | RUBELLA | APPENDICITIS | ACUTE CHOLECYSTITIS | ACUTE CHOLANGITIS | HEPATITIS B | ACUTE PYELONEPHRITIS | SALMONELLOSIS | CAMPYLOBACTER INFECTION |
|---|---|---|---|---|---|---|---|---|---|---|---|---|---|
| 27 | ○ | | | | | | | | | | | | |
| 28 | | | | | | | | | | | | ◎ | |
| 29 | | | | | | | | | | | | | ◎ |
| 30 | ○ | | | | | | ○ | | | | | ○ | |
| 31 | | ○ | | | | | ○ | | | | | | |
| 32 | | | | | | | | | ○ | ○ | ◎ | ○ | |
| 33 | ○ | | | | | | | | | | ○ | | ○ |
| 34 | | ○ | | | | | | | | | | | |
| 35 | | | | | | | ◎ | | | | | | |
| 36 | | | | | | | ◎ | | | | | | |
| 37 | | | | | | | | | | | | | |
| 38 | | | | | | | | | | | | | |
| 39 | | | | | | | | ◎ | | | | | |
| 40 | | | | | | | | | | | | | |
| 41 | | | | | | | | | | | | | |
| 42 | | | ○ | | | | | | ◎ | | | | |
| 43 | ○ | | | | | | | | | ○ | ◎ | | |
| 44 | | | | | | ○ | | | | | | | |
| 45 | | | | | | | | | | | | | |

FIG. 8

| RELATED SYMPTOM | SYMPTOM | STATE | PERIOD | DISEASE | PAST DISEASE | INITIAL CARE | CARE CLASSIFICATION | CARE | DETAILS |
|---|---|---|---|---|---|---|---|---|---|
| NONE | | | | INFLUENZA | NONE | CONSULT A DOCTOR | PROCEDURE | (HOT OR COLD) COMPRESS | 1 |
| | | | | | HIGH BLOOD PRESSURE | | | | 1 |
| | | | | | DIABETES | | | | 2 |
| | | | | | SCLERODERMA | | | | 3 |
| NONE | FEVER | HIGH FEVER | SHORT TIME | | NONE | CONSULT A DOCTOR | PROCEDURE | (HOT OR COLD) COMPRESS | 1 |
| | | | | | HIGH BLOOD PRESSURE | | | | 1 |
| | | | | | DIABETES | | | | 2 |
| | | | | | SCLERODERMA | | | | 3 |
| CHILL AND RIGOR (COLD AND SHAKING) | | | | ADENOIDITIS | NONE | CONSULT A DOCTOR | PROCEDURE | (HOT OR COLD) COMPRESS | 4 |
| | | | | | HIGH BLOOD PRESSURE | | | | 5 |
| | | | | | DIABETES | | | | 6 |
| | | | | | SCLERODERMA | | | | 7 |
| • • • | • • • | • • • | • • • | • • • | • • • | • • • | • • • | • • • | • • • |
| NONE | | | | INFLUENZA | NONE | CONSULT A DOCTOR | PROCEDURE | FLUID INTAKE | 11 |
| | | | | | HIGH BLOOD PRESSURE | | | | 11 |
| | | | | | DIABETES | | | | 12 |
| | | | | | SCLERODERMA | | | | 13 |
| NONE | FEVER | HIGH FEVER | SHORT TIME | | NONE | CONSULT A DOCTOR | PROCEDURE | FLUID INTAKE | 11 |
| | | | | | HIGH BLOOD PRESSURE | | | | 11 |
| | | | | | DIABETES | | | | 12 |
| | | | | | SCLERODERMA | | | | 13 |
| CHILL AND RIGOR (COLD AND SHAKING) | | | | ADENOIDITIS | NONE | CONSULT A DOCTOR | PROCEDURE | FLUID INTAKE | 14 |
| | | | | | HIGH BLOOD PRESSURE | | | | 15 |
| | | | | | DIABETES | | | | 16 |
| | | | | | SCLERODERMA | | | | 17 |
| • • • | • • • | • • • | • • • | • • • | • • • | • • • | • • • | • • • | • • • |

F I G . 9

| | (HOT OR COLD) COMPRESS |
|---|---|
| 1 | COOL THE REGIONS WHERE ARTERIES EXTEND SUCH AS THE FOREHEAD, UNDERARMS, THE NECK, AND THE GROIN WITH AN ICE BAG, A COLD PACK, AN ICE PILLOW, OR THE LIKE. BE CAREFUL NOT TO COOL THE SAME REGION FOR MORE THAN ONE HOUR. |
| 2 | COOL THE REGIONS WHERE ARTERIES EXTEND SUCH AS THE FOREHEAD, UNDERARMS, THE NECK, AND THE GROIN WITH AN ICE BAG, A COLD PACK, AN ICE PILLOW, OR THE LIKE. WHEN BLOOD FLOW IN LIMBS IS POOR, COOL ONLY THE HEAD. BE CAREFUL NOT TO COOL THE SAME REGION FOR MORE THAN ONE HOUR. |
| 3 | COOL THE FOREHEAD WITH AN ICE BAG, A COLD PACK, AN ICE PILLOW, OR THE LIKE. DURING COOLING, NOT TO COOL YOUR LIMBS. BE CAREFUL NOT TO COOL THE SAME REGION FOR MORE THAN ONE HOUR. |
| 4 | SINCE THERE IS SHAKING, WARM THE BODY WITH BEDDING OR THE LIKE. COOL ONLY THE FOREHEAD. IN THE CASE OF USING ELECTRIC BLANKET OR HOT PILLOW, BE CAREFUL NOT TO BURN THE BODY. |
| 5 | SINCE THERE IS SHAKING, WARM THE BODY WITH BEDDING OR THE LIKE. COOL ONLY THE FOREHEAD. IN THE CASE OF USING ELECTRIC BLANKET OR HOT PILLOW, BE CAREFUL NOT TO BURN THE BODY. |
| 6 | SINCE THERE IS SHAKING, WARM THE BODY WITH BEDDING OR THE LIKE. COOL ONLY THE FOREHEAD. IN THE CASE OF USING ELECTRIC BLANKET OR HOT PILLOW, BE CAREFUL NOT TO BURN THE BODY. IF BLOOD FLOW TO LEGS IS POOR, BE VERY CAREFUL BECAUSE TEMPERATURE SENSIBILITY MAY BE LOW. |
| 7 | SINCE THERE IS SHAKING, WARM THE BODY WITH BEDDING OR THE LIKE. COOL ONLY THE FOREHEAD. IN THE CASE OF USING ELECTRIC BLANKET OR HOT PILLOW, BE CAREFUL NOT TO BURN THE BODY. |
| ⋮ | ⋮ |

FIG. 10

| | FLUID INTAKE |
|---|---|
| 11 | AT THE TIME OF FEVER, FLUID BECOMES INSUFFICIENT DUE TO SWEATING OR THE LIKE. TAKE SUFFICIENT FLUID. SINCE ELECTROLYTE ALSO TENDS TO BE INSUFFICIENT, DRINK WATER AND, PREFERABLY, A SPORTS DRINK INCLUDING ELECTROLYTE. |
| 12 | AT THE TIME OF FEVER, FLUID BECOMES INSUFFICIENT DUE TO SWEATING OR THE LIKE. TAKE SUFFICIENT FLUID. SINCE ELECTROLYTE ALSO TENDS TO BE INSUFFICIENT, DRINK WATER AND, PREFERABLY, A SPORTS DRINK INCLUDING ELECTROLYTE. BE CAREFUL NOT TO TAKE TOO MUCH Na. |
| 13 | AT THE TIME OF FEVER, FLUID BECOMES INSUFFICIENT DUE TO SWEATING OR THE LIKE. TAKE SUFFICIENT FLUID. SINCE ELECTROLYTE ALSO TENDS TO BE INSUFFICIENT, DRINK WATER AND, PREFERABLY, A SPORTS DRINK INCLUDING ELECTROLYTE. HOWEVER, SPOTRS DRINK CONTAINS ALSO SUGAR, SO THAT BE CAREFUL NOT TO TAKE TOO MUCH SUGAR. |
| ⋮ | ⋮ |

F I G . 1 1
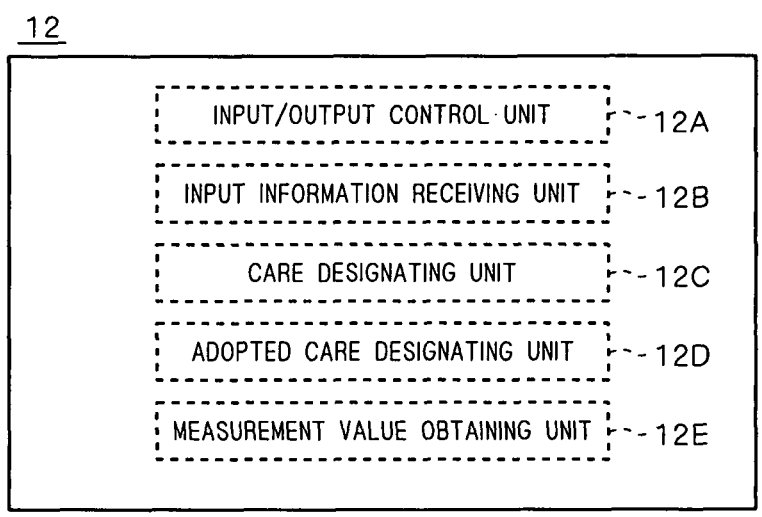

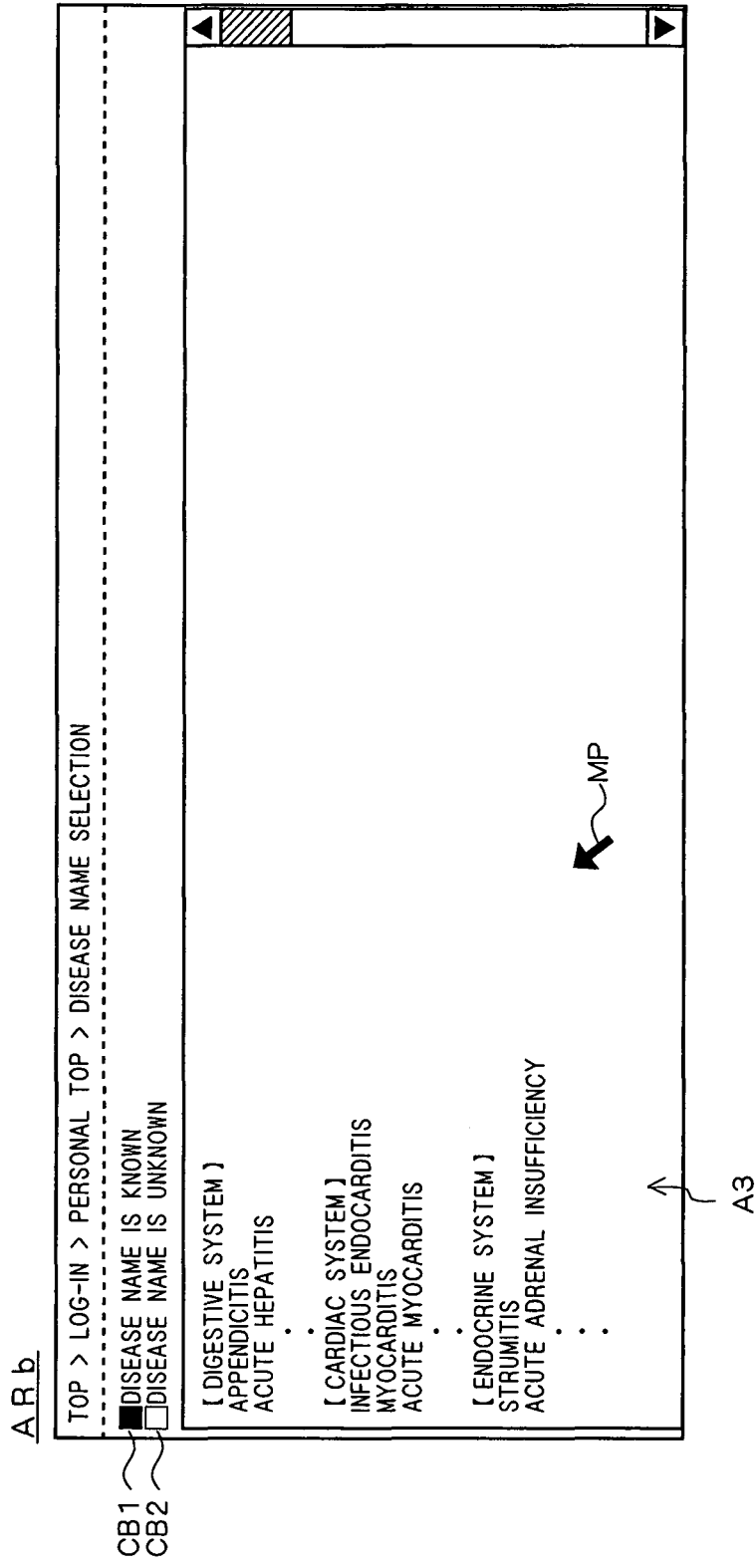

FIG. 22

ARc

TOP > LOG-IN > PERSONAL TOP > DISEASE NAME SELECTION > DETAILED SYMPTON

BK1 — ■DETAILED SYMPTOM SELECTION■
DISEASE : APPENDICITIS
●SELECT FROM THE FOLLOWING PULL-DOWN MENUES
PD — PATIENT : [SELF ▼]  SEX : [MALE ▼]  AGE : [51 TO 65 ▼]
●SELECT FROM THE PULL-DOWN NEMUES (REQUIRED).  ← MP
DS — FEVER : [37.0 TO 37.9℃ (SLIGHT FEVER) ▼]  PERIOD : [ONE DAY ▼]
STATE OF FEVER :
PF — [BODY TEMPERATURE VARIATION IN ONE DAY IS 1℃ OR LESS ▼]

●SELECT PAST DISEASES AND ENTER TO CHECK BOXES
SF — [DIABETES] [GLOMERULONEPHRITIS]
[HYPERTENSION] [ASTHMA]
[EGG ALLERGY]

●PLEASE FILL IN PAST DISEASE WHICH IS NOT IN THE OPTIONS
[    ] [    ] [    ]   — CK

[NEXT] — NB1
[RESET] — RB1

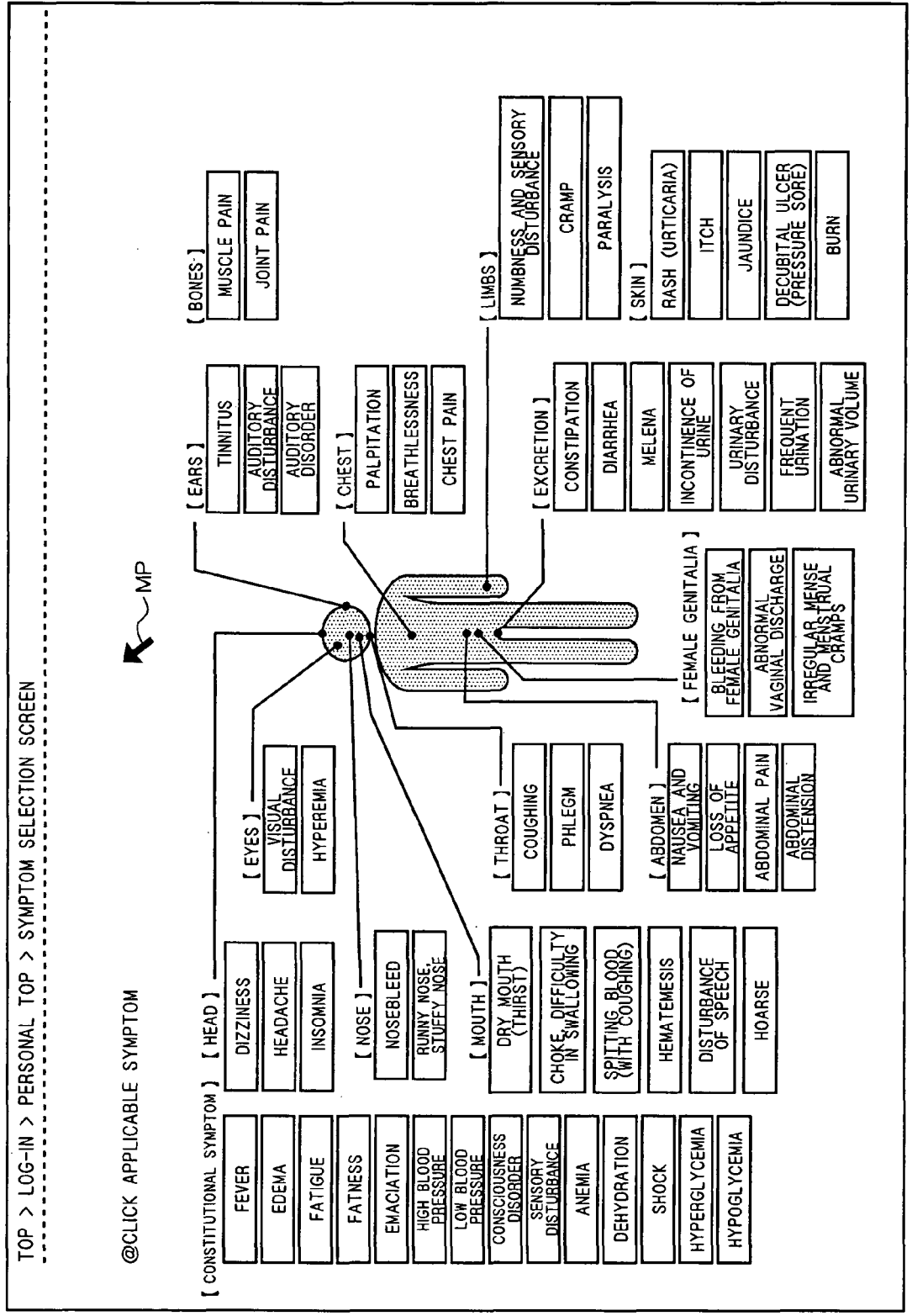

FIG. 25

ARf

TOP> LOG-IN > PERSONAL TOP > DISEASE NAME SELECTION > DETAILED SYMPTON

■DETAILED SYMPTOM SELECTION■ —BK1
DISEASE: NONE

●SELECT FROM THE FOLLOWING PULL-DOWN MENUES
PATIENT:    SEX:    AGE:
SELF [v]   MALE [v]   51 TO 65 [v]  ←MP
↑
PD

●SELECT FROM THE PULL-DOWN MENUES (REQUIRED).
FEVER:    PERIOD:
37.0 TO 37.9°C (SLIGHT FEVER) [v]   ONE DAY [v]
↑
DS

STATE OF FEVER:
BODY TEMPERATURE VARIATION IN ONE DAY IS 1°C OR LESS [v] —PF

●SELECT PAST DISEASES AND ENTER TO CHECK BOXES
[GLOMERULONEPHRITIS]
[DIABETES]   [ASTHMA]
[HYPERTENSION]
[EGG ALLERGY]
↑
SF

●PLEASE FILL IN PAST DISEASE WHICH IS NOT IN THE OPTIONS
[ ] [ ] [ ]  —CK

[NEXT] —NB1
[RESET] —RB1

FIG. 26

ARg

TOP>LOG-IN>PERSONAL TOP>DISEASE NAME SELECTION>DETAILED SYMPTOM>ADDITIONAL SYMPTOM>NARROW DOWN DISEASE NAMES

■SEARCH RESULT■

● THE DISEASE IS PROBABLY COLD BUT MAY BE INFLUENZA. TO DISPLAY MORE ACCURATE CARE, DISEASES HAVE TO BE NARROWED DOWN. PLEASE ANSWER THE FOLLOWING QUESTIONS.

① DID YOU RECEIVE VACCINATION AGAINST INFLUENZA?  [YES ∨]

② IF "YES", WHEN DID YOU RECEIVE IT? [WITHIN 6 MONTHS ∨]

③ DID YOU CATCH INFLUENZA IN THE PAST SIX MONTHS? [YES ∨]

④ IS YOUR FAMILY MEMBER OR CLOSE PERSON HAVING INFLUENZA? [YES ∨]

MP ← [SEARCH] — SB4

ARh

TOP>LOG-IN>PERSONAL TOP>DISEASE NAME SELECTION>DETAILED SYMPTOM>ADDITIONAL SYMPTOM>NARROW DOWN DISEASE NAMES>SELECTION

■SEARCH RESULT■

● THE DISEASE MAY BE "COLD" OR "INFLUENZA". PLEASE SELECT ONE OF THEM.

⊙ COLD
○ INFLUENZA

MP

SEARCH ⌐ SB5

FIG. 35

ARk

TOP>LOG-IN>PERSONAL TOP>SYMPTOM SELECTION SCREEN>DETAILED SYMPTOM>ADDITIONAL SYMPTOM>CARING METHOD>INPUT TO ELECTRONIC MEDICAL RECORD

● YOU CAN ADD DATA TO ELECTRONIC MEDICAL RECORD.

- BY SELECTING MEASUREMETN VALUES, THEY CAN BE REGISTERED TOGETHER WITH SYMPTOM, DISEASE NAME, AND ADOPTED CARING METHOD IN ELECTRONIC MEDICAL RECORD.

■ MEASUREMENT VALUE OF BLOOD PRESSURE :
MAXIMUM BLOOD PRESSURE : [150mmHg ∨] MX
MINIMUM BLOOD PRESSURE : [100mmHg ∨] MN

■ MEASUREMENT VALUE OF BODY TEMPERATURE : [3 8 . 1 ℃ ∨] TP

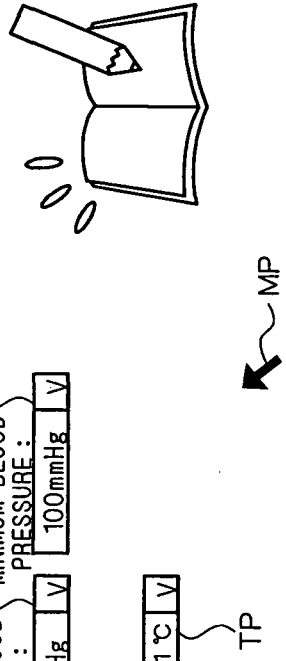
← MP

RT — [RETURN]
CL — [CLEAR]
RC — [REGISTER MEASUREMENT VALUES TOGETHER WITH SYMPTOM, DISEASE NAME, AND CARING METHOD]

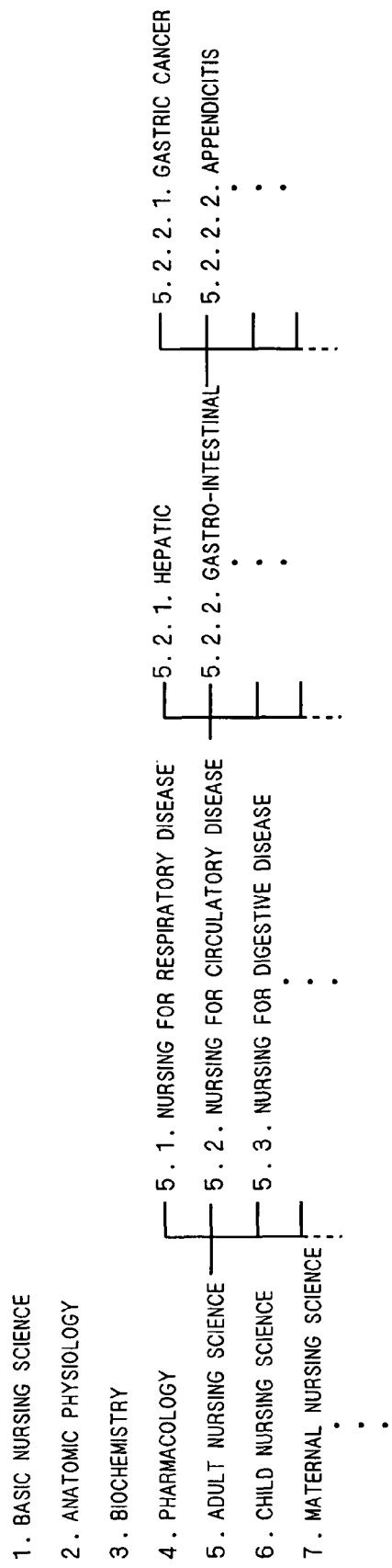

F I G . 3 8
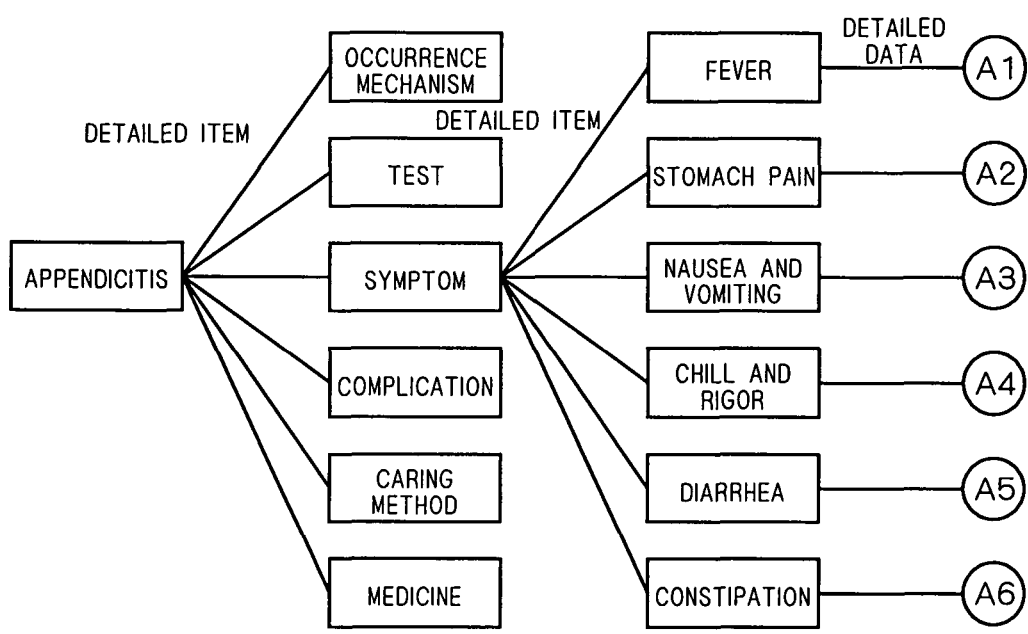

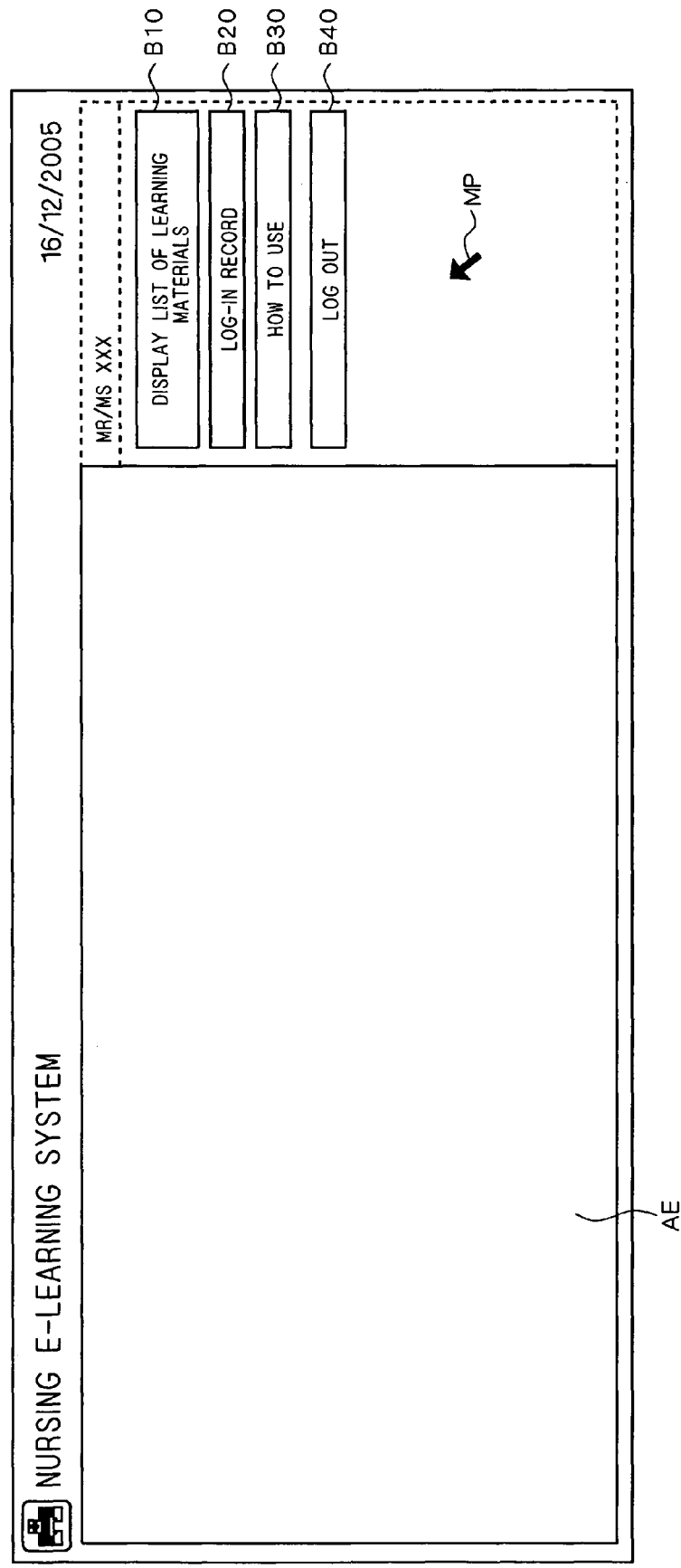

F I G. 4 4

AEa

●WRITE WHAT YOU WOULD LIKE TO KNOW, AND CLICK SEARCH BUTTON.

SB11
LS1

1. BASIC NURSING SCIENCE
2. ANATOMIC PHYSIOLOGY
3. BIOCHEMISTRY
4. PHARMACOLOGY
5. ADULT NURSING SCIENCE ─┬─ 5.1. NURSING FOR RESPIRATORY DISEASE
6. CHILD NURSING SCIENCE    ├─ 5.2. NURSING FOR CIRCULATORY DISEASE ─┬─ 5.2.1. HEPATIC
7. MATERNAL NURSING SCIENCE ├─ 5.3. NURSING FOR DIGESTIVE DISEASE    ├─ 5.2.2. GASTRO-INTESTINAL ─┬─ 5.2.2.1. GASTRIC CANCER
   ...                      ...                                       ...                          ├─ 5.2.2.2. APPENDICITIS
                                                                                                   ...  MP

LS2
SB12

●SELECT SYMPTOM DESIRED TO LEARN FROM THE LIST

1. FEVER
2. HEADACHE
3. NAUSEA
   ...

FIG. 47

AEd

COMMENT (APPENDICITIS - OCCURRENCE MECHANISM)

THE CAUSE IS NOT FULLY FOUND OUT YET. IT IS CONSIDERED THAT SOMETHING IS CLOGGED IN THE APPENDIX AND CAUSES INFLAMMATION AND INFECTION. DUE TO THE INFLAMMATION, THE APPENDIX BECOMES ENLARGED AND AN ULCER GROWS IN THE MUCOSA. FURTHER, SANIES ARE COLLECTED IN THE CAVITY. WHEN THE DISEASE BECOMES SERIOUS, THE MUCOSAL ULCERATION ENTERS THE DEEPER PART. THE WALL BECOMES GANGRENOUS, AND PERFORATED APPENDICITIS MAY DEVELOP TO GENERAL PERITONITIS. THERE IS ALSO A CASE WHERE THE APPENDIX IS ADHERED TO THE PERIPHERAL ORGANS TO FORM ABSCESS WITHOUT DESTRUCTION IN THE APPENDIX (ABSCESS AROUND THE APPENDIX).

(QUESTION) (NEXT) (BACK) (END)
         MP

FIG. 48

AEe

COMMENT (APPENDICITIS - FEVER - OCCURRENCE MECHANISM)

WHEN TISSUE DAMAGE SUCH AS INFLAMMATION OCCURS, MACROPHAGE AS IMMUNOCOMPETENT CELLS PHAGOCYTOSE, AND ENDOGENOUS PYROGEN IS GENERATED. THE ENDOGENOUS PYROGEN ACTS ON VASCULAR ENDOTHELIAL CELLS, THE TEMPERATURE REGULATORY CENTER IN THE HYPOTHALAMUS IS STIMULATED, PROSTAGLANDIN INCREASES, THE BODY TEMPERATURE ADJUSTING LEVEL IS SET TO HIGH TEMPERATURE VALUE, AND FEVER IS DEVELOPED.

(QUESTION) (NEXT) (BACK) (END)
         MP

AEh

■ANSWER■    ●QUESTION : WHY DOES APPENDICITIS OCCUR?

RETURN — MP

AEi

■ANSWER■    ●QUESTION : WHY DOES APPENDICITIS OCCUR?

ANSWER WILL BE GIVEN LATER BY EXPERTS.

RETURN — MP

FIG. 53

| RELATED SYMPTOM | SYMPTOM | STATE | PERIOD | DISEASE | PAST DISEASE | INITIAL CARE | CARE CLASSIFICATION | CARE | DETAILS |
|---|---|---|---|---|---|---|---|---|---|
| NONE | | | | INFLUENZA | NONE | CONSULT A DOCTOR | PROCEDURE | (HOT OR COLD) COMPRESS | 1,5 |
| | | | | | HIGH BLOOD PRESSURE | | | | 1,5 |
| | | | | | DIABETES | | | | 1,3,5 |
| | | | | | SCLERODERMA | | | | 2,4,5 |
| NONE | FEVER | HIGH FEVER | SHORT TIME | ADENOIDITIS | NONE | CONSULT A DOCTOR | PROCEDURE | (HOT OR COLD) COMPRESS | 1,5 |
| | | | | | HIGH BLOOD PRESSURE | | | | 1,5 |
| | | | | | DIABETES | | | | 1,3,5 |
| | | | | | SCLERODERMA | | | | 2,4,5 |
| CHILL AND RIGOR (COLD AND SHAKING) | | | | | NONE | CONSULT A DOCTOR | PROCEDURE | (HOT OR COLD) COMPRESS | 2,5,6,7 |
| | | | | | HIGH BLOOD PRESSURE | | | | 2,5,6,7 |
| | | | | | DIABETES | | | | 2,3,5,6,7 |
| | | | | | SCLERODERMA | | | | 2,4,5,6,7 |
| ... | ... | ... | ... | ... | ... | ... | ... | ... | ... |

FIG. 54

| COMPRESS | DETAILS | NUMBER |
|---|---|---|
| COLD COMPRESS | COOL THE REGIONS WHERE ARTERIES EXTEND SUCH AS THE FOREHEAD, UNDERARMS, THE NECK, AND THE GROIN WITH AN ICE BAG, A COLD PACK, AN ICE PILLOW, OR THE LIKE. | 1 |
| | COOL THE FOREHEAD WITH AN ICE BAG, A COLD PACK, AN ICE PILLOW, OR THE LIKE. | 2 |
| | WHEN BLOOD FLOW IN LIMBS IS POOR, COOL ONLY THE HEAD. | 3 |
| | DURING COOLING, NOT TO COOL YOUR LIMBS. | 4 |
| | BE CAREFUL NOT TO COOL THE SAME REGION FOR MORE THAN ONE HOUR. | 5 |
| HOT COMPRESS | WARM THE BODY WITH BEDDING OR THE LIKE. IN THE CASE OF USING ELECTRIC BLANKET OR HOT PILLOW, BE CAREFUL NOT TO BURN THE BODY. | 6 |
| | IF BLOOD FLOW TO LEGS IS POOR, BE VERY CAREFUL BECAUSE TEMPERATURE SENSIBILITY MAY BE LOW. | 7 |

FIG. 55

DBK

WARM THE BODY WITH BEDDING OR THE LIKE. IN THE CASE OF USING ELECTRIC BLANKET OR HOT PILLOW, BE CAREFUL NOT TO BURN THE BODY. IF BLOOD FLOW TO LEGS IS POOR, BE VERY CAREFUL BECAUSE TEMPERATURE SENSIBILITY MAY BE LOW. COOL THE FOREHEAD WITH AN ICE BAG, A COLD PACK, AN ICE PILLOW, OR THE LIKE. DURING COOLING, NOT TO COOL YOUR LIMBS. BE CAREFUL NOT TO COOL THE SAME REGION FOR MORE THAN ONE HOUR.

FIG. 56

| COMPRESS | CLASSIFICATION | DETAILED ELEMENT | NUMBER |
|---|---|---|---|
| COLD COMPRESS | REGION | THE FOREHEAD | A-1 |
| | | THE UNDERARMS | A-2 |
| | | THE NECK | A-3 |
| | | THE GROIN | A-4 |
| | COOLING MEANS | AN ICE BAG | B-1 |
| | | A COLD PACK | B-2 |
| | | AN ICE PILLOW | B-3 |
| | NOTE | NOT TO COOL THE SAME REGION FOR MORE THAN ONE HOUR | C-1 |
| | | NOT TO COOL YOUR LIMBS | C-2 |
| HOT COMPRESS | WARMING MEANS | ELECTRIC BLANKET | D-1 |
| | | HOT PILLOW | D-2 |
| | NOTE | BE CAREFUL NOT TO BURN THE BODY | E-1 |
| | | IF BLOOD FLOW TO LEGS IS POOR, BE VERY CAREFUL NOT TO BURN THE BODY. | E-2 |

FIG. 57

DBK

COOL THE FOREHEAD WITH AN ICE BAG, A COLD PACK, AN ICE PILLOW, OR THE LIKE. BE CAREFUL NOT TO COOL THE SAME REGION FOR MORE THAN ONE HOUR. NOT TO COOL YOUR LIMBS. WARM ELECTRIC BLANKET, HOT PILLOW, OR THE LIKE. BE CAREFUL NOT TO BURN THE BODY. IF BLOOD FLOW TO LEGS IS POOR, BE VERY CAREFUL NOT TO BURN THE BODY.

FIG. 59

| No | DETAILED DATA |
|---|---|
| 11 | BE CAREFUL WITH WATER BALANCE··· |
| 21 | AT THE TIME OF COOLING THE FEMORAL REGION,··· |
| 31 | WHEN SWEATING, CHANGE CLOTHES FREQUENTLY··· |
| 41 | NOT TO APPLY STIMULUS··· |
| 51 | THE SAME BODY POSTURE FOR TWO HOURS··· |
| 61 | DUE TO FEVER, ENERGY BECOMES··· |
| 71 | AT THE TIME OF TAKING FLUID, SACCHARIDES··· |
| 81 | TO PREVENT INFECTION··· |
| 91 | INSULIN··· |

FIG. 60

AEk

● WRITE WHAT YOU WOULD LIKE TO KNOW, AND CLICK SEARCH BUTTON.

CARING METHODS FOR A DIABETIC PATIENT HAVING FEVER
DUE TO APPENDICITIS

SEARCH
SB31
MP

● IF YOU WOULD LIKE TO KNOW CARING METHOD FROM SYMPTOM,
SELECT SYMPTOM FROM THE LIST

1. FEVER
2. HEADACHE
3. NAUSEA
    ·
    ·
    ·

DATABASE SYSTEM, PROGRAM, AND INFORMATION PROCESSING METHOD

This application is based on application No. 2006-284053 filed in Japan, the contents of which are hereby incorporated by reference.

BACKGROUND OF THE INVENTION

1. Field of the Invention

The present invention relates to a database system.

2. Description of the Background Art

In recent years, the necessity of at-home nursing/care is increasing due to social backgrounds of the medical treatment such as increase in medical expenses as the number of elderly people increases, changes in the disease structures, calculation of medical expenses according to the diagnosis procedure combination (DPC) method, reduction in the number of stay days in a hospital, and introduction of care insurance.

On the other hand, problems occur due to lack of knowledge of medical treatment of a person cared at home and his/her family, immature system of providing knowledge for nursing/care at home, and the like. In addition, a system to give knowledge and experience to nurses with no or little experience in sites of care is not ready. It is consequently an issue to be urgently worked out to construct the system for improving the quality of nursing.

To address the issue, various techniques are proposed. In the techniques, when data of a symptom is entered, various information is provided for the symptom, such as information of disease history and practice record, disease names and medical care performed for the diseases, diagnosis document of blood pressure, names of suspected diseases or of diseases to be paid his/her attention to and explanatory information thereof, disease information and medicine information for promoting the healing, and the like (for example, Japanese Patent Application Laid-Open Nos. H7-56947, 2002-342491, 2001-282538, 2003-22325, 2004-118566, and 2004-133774).

In the above techniques, however, only comment on a disease corresponding to a symptom and a general treatment for the disease are presented. The techniques have drawbacks such that the user cannot select information of a desired caring method, and an operation of making a desired caring method displayed is complicated.

SUMMARY OF THE INVENTION

The present invention is directed to a database system.

According to the present invention, the database system includes: a first database that stores information obtained by combining each of a plurality of disease name elements with one or more symptom elements, each of the plurality of disease name elements indicating a disease name, and each of the one or more symptom elements indicating a symptom; a second database that stores information obtained by combining each of the plurality of disease name elements with a plurality of care elements, each of the plurality of care elements indicating a care; a symptom recognizing unit that recognizes one or more symptom elements in response to an input of information from the user; a disease name detecting unit that detects one disease name element combined with all of one or more symptom elements recognized by the symptom recognizing unit in the first database; a care detecting unit that detects a plurality of care elements combined with one disease name element detected by the disease name detecting unit in the second database; a disease care information generating unit that generates disease care information obtained by combining one disease name element detected by the disease name detecting unit with a plurality of care elements detected by the care detecting unit; and an output control unit for visibly outputting the disease care information in an output device.

When a symptom is entered, a disease name according to the symptom and a plurality of cares are visibly presented. Therefore, information of a desired caring method according to the situations can be easily obtained.

According to another aspect of the present invention, the database system includes: a storing unit that stores related information and stores one or more pieces of detailed data each indicative of details of an item element so as to be associated with at least a part of item elements included in a plurality of item elements, the plurality of item elements indicating a plurality of items including at least a symptom, a disease, and a caring method, and the related information being information in which the plurality of item elements are associated with each other and two or more item elements of a caring method belong to each of item elements of a disease; an element recognizing unit that recognizes one or more item elements including at least an item element of a disease in response to an input of information from a user; a related information extracting unit that extracts partial related information from the related information in response to recognition of the one or more item elements by the element recognizing unit, the partial related information indicating three or more item elements including the one or more item elements and two or more item elements of a caring method associated so as to belong to the one or more item elements, and association among the three or more item elements; and a display control unit that controls so as to visibly output, in a display unit, network information obtained by associating item elements with each other in a network form on the basis of the partial related information.

When a desired item is designated in a state where a plurality of items including two or more items of a caring method are associated with each other in a network form and visibly presented, the details of the designated item are visibly presented. Therefore, the user can easily obtain the detailed information of a desired caring method according to situations.

The present invention is also directed to a computer software product including a recording medium recording a computer-readable software program that operates a computer as a database system.

The present invention is further directed to an information processing method.

Therefore, an object of the present invention is to provide a technique capable of easily obtaining information of a desired care method according to situations.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a block diagram showing the functional configuration of the nursing learning support system;

FIG. 3 is a diagram showing outline of information process operations in a nursing supporting process;

FIGS. 4 to 8 are diagrams showing concrete examples of information of a disease-symptom-combination DB;

FIGS. 9 and 10 are diagrams showing concrete examples of information of a detailed data group;

FIG. 11 is a block diagram showing functions realized by a terminal control unit;

FIG. 21 is a diagram showing a disease name selection screen of the nursing support system;

FIG. 22 is a diagram showing a detailed symptom input screen of the nursing support system;

FIG. 24 is a diagram showing a main symptom selection screen of the nursing support system;

FIG. 25 is a diagram showing a detailed symptom input screen of the nursing support system;

FIG. 26 is a diagram showing a narrow-down question screen of the nursing support system;

FIG. 35 is a diagram illustrating an electronic medical record input screen;

FIGS. 37 and 38 are diagrams showing concrete examples of teaching element associated information;

FIG. 43 is a diagram showing the configuration of a display screen of a learning support system;

FIG. 44 is a diagram showing a personal top screen of the learning support system;

FIGS. 47 and 48 are diagrams showing display examples of a comment display screen;

FIG. 53 is a diagram showing information constructing a disease-care-combination DB in a modification;

FIG. 54 is a diagram showing a concrete example of information constructing a detailed data group in a modification;

FIG. 55 is a diagram showing a state where detailed care elements are visibly output in a modification;

FIG. 56 is a diagram showing a concrete example of information constructing a detailed data group in a modification;

FIG. 57 is a diagram showing a state where detailed care elements are visibly output in a modification;

FIG. 59 is a diagram showing a concrete example of information constructing a detailed data group in a modification;

FIG. 60 is a diagram showing a personal top screen of a learning support system of a modification;

DESCRIPTION OF THE PREFERRED EMBODIMENTS

Embodiments of the present invention will be described hereinbelow with reference to the drawings.

Outline of Nursing Learning Support System

Figure 1:
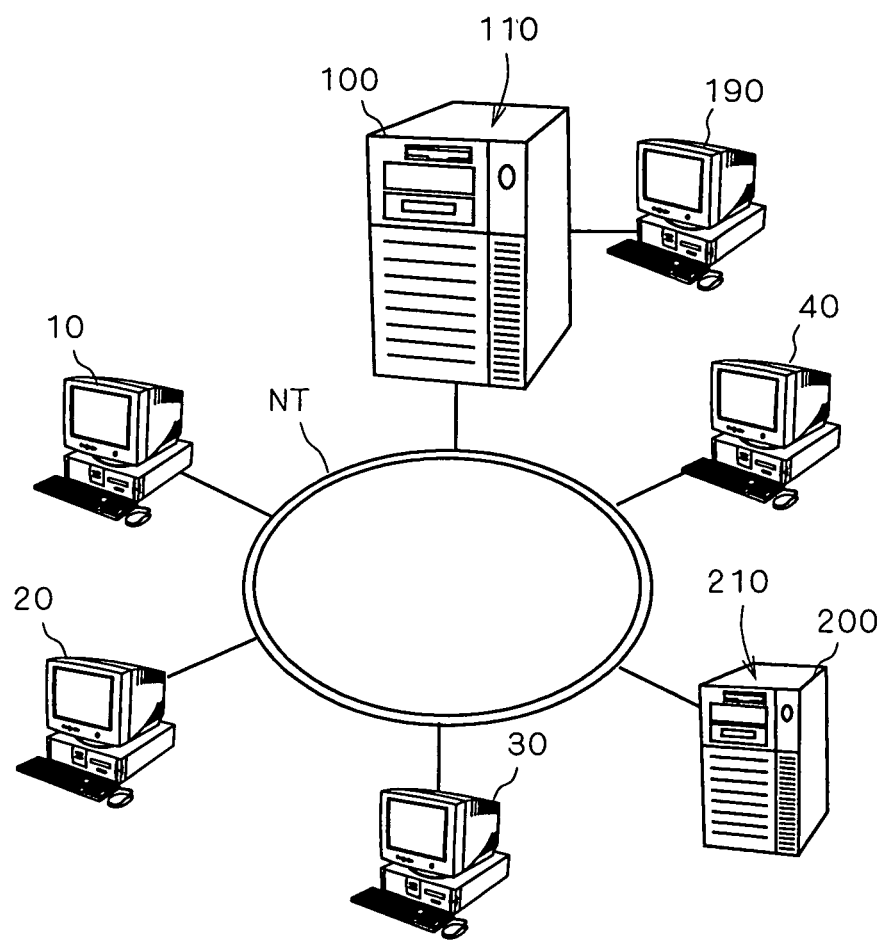
FIG. 1 is a diagram showing a schematic configuration of a nursing learning support system of an embodiment.

FIG. 1 is a diagram showing a schematic configuration of a nursing learning support system 1 according to an embodiment of the invention.

As shown in FIG. 1, the nursing learning support system 1 has a server 100, a hospital server 200, and terminals 10, 20, 30, and 40. The server 100, hospital server 200, and terminals 10 to 40 are connected to each other via a network line NT such as the Internet so that data can be transmitted/received to/from each other. To the server 100, a terminal (management terminal) 190 for managing the nursing learning support system 1 is connected so that data can be transmitted/received.

The server 100 has a database (hereinbelow, called "medical DB") 110 that stores various medical information such as information for supporting medical nursing and care and teaching material information on nursing and care. The server 100 provides information for selecting information desired to be obtained and information desired to be learned to the terminals 10 to 40 and, in response to a request from the terminals 10 to 40, provides the information for supporting nursing and care, data showing a matter of substance of a teaching on nursing, and the like to the terminals 10 to 40.

That is, the server 100 has the function of providing information for supporting nursing and care (nursing supporting function) and the function of realizing a so-called e-learning system for supporting learning by providing a learning material on nursing (learning supporting function).

The hospital server 200 is mounted in a hospital or the like and has a database (hereinbelow, called "medical record DB") 210 that stores information of electronic medical records and the like. The hospital server 200 provides the information in the medical record DB 210 to the server 100 and the terminals 10 to 40 or adds new information to the medical record DB 210 in response to a request from the server 100 and the terminals 10 to 40.

The nursing learning support system 1 functions as a database system that presents information stored in a medical DB 110, the medical record DB 210, and the like in response to a request of the user.

Functional Configuration of Nursing Learning Support System

FIG. 2 is a block diagram showing the functional configuration of the nursing learning support system 1. Since the functions of the terminals 10 to 40 are similar to each other, representative one of the terminals 10 to 40 is shown in FIG. 2 to prevent complication of the diagram.

Terminals 10 to 40

The terminals 10 to 40 are, for example, personal computers used in houses and the like. The terminals 10 to 40 may be portable terminals (PDAs) or the like. Each of the terminals 10 to 40 has, mainly, a storing unit 11, a terminal control unit 12, a display unit 13, an operation unit 14, and an interface (I/F) 15.

The storing unit 11 is constructed by, for example, a hard disk or the like and stores a program PG1 for realizing a part of the functions of the nursing learning support system 1.

The terminal control unit 12 has a CPU and a memory and realizes various functions and operations on the basis of various signals from the operation unit 14, the program PG1 stored in the storing unit 11, and the like. The terminal control unit 12 reads and executes the program PG1 stored in the storing unit 11, thereby realizing the various functions and operations of the nursing learning support system 1. Various data properly generated in the information process in the terminal control unit 12 is temporarily stored in the memory.

The display unit 13 is constructed by an output device such as a CRT or a liquid crystal panel and, in response to a signal from the terminal control unit 12, visually outputs various images.

The operation unit 14 has, for example, a keyboard, a mouse and the like and, in response to various operations of the users (patients, care persons, and the like) of the terminals 10 to 40, transmits various signals according to the operations to the terminal control unit 12.

The I/F 15 is an interface for controlling transmission/reception of data via the network line NT with the server 100 and the like.

Management Terminal 190

The management terminal 190 is constructed by, for example, a personal computer and the like. The management terminal 190 has, mainly, a storing unit 191, a PC control unit 192, a display unit 193, an operation unit 194, and an interface (I/F) 195.

The storing unit 191 is constructed by, for example, a hard disk or the like and stores a program PG2 for realizing a part of the functions of the nursing learning support system 1.

The PC control unit 192 has a CPU and a memory and realizes various functions and operations on the basis of various signals from the operation unit 194, the program PG2 stored in the storing unit 191, and the like. The PC control unit 192 reads and executes the program PG2 stored in the storing unit 191, thereby realizing the various functions and operations of the nursing learning support system 1 such as a function of controlling display of various images in the display unit 193. Various data properly generated in the information process in the PC control unit 192 is temporarily stored in the memory.

The display unit 193 is constructed by, for example, a CRT or a liquid crystal panel and, in response to a signal from the PC control unit 192, visually outputs various images.

The operation unit 194 has, for example, a keyboard, a mouse and the like. When the operation unit 194 is properly operated by the user (that is, a controller) of the management terminal 190, various signals according to the operations to the PC control unit 192 are transmitted.

The I/F 195 is an interface for controlling transmission/reception of data to/from the server 100.

Server 100

The server 100 has, mainly, a storing unit 101, a server control unit 102, and an interface (I/F) 105.

The storing unit 101 is constructed by, for example, a hard disk or the like and stores a program PG3 for realizing the functions of the server 100. The storing unit 101 stores data (hereinbelow, also called "analysis data") 101a used for a language analysis to be described later, and the medical DB 110. In the storing unit 101, various data for realizing the functions of the nursing learning support system 1 is also stored.

The medical DB 110 stores a disease-symptom-combination database (DB) 111, a disease-care-combination database (DB) 112, a disease-symptom database (DB) 113, a teaching element associated information 114, and a detailed data group 115.

The analysis data 101a includes data necessary for a so-called morphological analysis (hereinbelow, called "morphological analysis data") and data necessary for a dependency structure analysis (hereinbelow, called "dependency analysis data"). The analysis data 101a includes data of various keywords (hereinbelow called "keyword data") such as terms and phrases related to medical information such as a symptom, and data of a dictionary (hereinbelow, called "dictionary data") in which a plurality of synonyms (for example, "development of fever" and "fever onset", "stomach pain" and "stomachache", and the like) and representative words of the plurality of synonyms (for example, "fever onset" and "stomachache") are associated with each other. The dictionary data may include data of a technical dictionary such as a thesaurus dictionary. The morphological analysis data, dependency structure analysis data, keyword data, and dictionary data is entered in advance from the management terminal 190 or the like and stored in the storing unit 101. The keyword data may be obtained by machine learning.

The disease-symptom-combination DB 111 stores information (hereinbelow, called "symptom-disease-combination information") of combinations each made of each of a plurality of data elements indicative of disease names (hereinbelow, called "disease name elements") and one or more pieces of data elements indicative of symptoms of the disease name elements (hereinbelow, called "symptom element").

The disease-care-combination DB 112 stores information of combinations of a plurality of data elements indicative of cares (hereinbelow, called "care element") corresponding to each of disease name elements included in a plurality of disease name elements with each of the disease name elements. The disease-care-combination DB 112 includes information (hereinbelow, called "detailed care element combination information") of combinations each made of one or more data elements (hereinbelow, called "detailed care element") of detailed information of caring methods with the care element.

The disease-symptom DB 113 stores information of each of disease name elements included in the plurality of disease name elements combined with one or more symptom elements indicative of one or more symptoms unconditionally determined for each of the disease names.

The teaching element associated information 114 is information obtained by associating a plurality of data elements indicative of items of teachings (hereinbelow, also called "teaching elements") related to a plurality of items including at least symptoms, diseases, and care methods with each other. In the teaching element associated information 114, two or more teaching elements related to a care method belong to each of teaching elements of a disease.

The detailed data group 115 stores data showing the details (hereinbelow, called "detailed data") of each of the teaching elements of at least a part of the plurality of teaching elements. Out of the detailed data, detailed data of each of the teaching elements of the caring method also functions as one or more data elements (hereinbelow, called "detailed care element") indicative of detailed data of each of the plurality of care elements.

The server control unit 102 has a CPU and a memory and controls the operation of the nursing learning support system 1 on the basis of various signals from the management terminal 190 and the terminals 10 to 40, the program PG3, and the like. For example, the server control unit 102 reads and executes the program PG3 stored in the storing unit 101 on the basis of the signal from the management terminal 190, thereby realizing the various functions and operations of the nursing learning support system 1. Various data properly generated in the information process in the server control unit 102 is temporarily stored in the memory.

The I/F 105 is an interface for controlling transmission/reception of data via the network line NT to/from the terminals 10 to 40, the server 200, and the like, and for controlling transmission/reception of data to/from the management terminal 190.

Hospital Server 200

The hospital server 200 has, mainly, a storing unit 201, a control unit 202, a display unit 203, an operation unit 204, and an interface (I/F) 205.

The storing unit 201 is constructed by, for example, a hard disk or the like and stores a program PG4 for realizing a part of the functions of the nursing learning support system 1 and the database (medical record DB) 210 storing a number of pieces of electronic medical record information.

Each of a number of pieces of electronic medical record information stored in the medical record DB 210 includes information for specifying electronic medical record information such as a medical record number, that is, information specifying the location (hereinbelow, called "location specifying information). The electronic medical record information is described in a mode so that the personal information of a patient (for example, a past disease, sex, age, and the like) can be identified by being distinguished from other information. That is, in the medical record DB 210, one or more pieces of data elements indicative of personal information (hereinbelow, also called "personal information elements") and location specifying information such as a medical record number specifying the location of the personal information element(s) is/are stored so as to be associated with each other.

The control unit 202 has a CPU and a memory and realizes various functions and operations on the basis of various signals from the operation unit 204, the program PG4 stored in the storing unit 201, and the like. The control unit 202 reads and executes the program PG4 stored in the storing unit 201, thereby realizing the various functions and operations of the nursing learning support system 1. Various data properly generated in the information process in the control unit 202 is temporarily stored in the memory.

The display unit 203 is constructed by, for example, a CRT or a liquid crystal panel and, in response to a signal from the control unit 202, visually outputs various images.

The operation unit 204 has, for example, a keyboard, a mouse and the like. When the operation unit 204 is properly operated by the user of the hospital server 200 (for example, a doctor, a medical clerk, or the like), various signals according to the operations are sent to the control unit 202.

The I/F 205 is an interface for controlling transmission/reception of data to/from the server 100 and the like via the network line NT.

In the nursing learning support system 1, when the functions of the terminal control unit 12, the server control unit 102, the PC control unit 192, and the control unit 202 cooperate each other and transmit/receive data to/from each other, processes of the care supporting function (hereinbelow, called "care supporting process") and processes of the learning supporting function (hereinbelow, called "learning supporting process") are realized.

The care supporting process in the nursing learning support system 1 will be described first and, after that, the learning supporting process will be described.

Care Supporting Process

Outline of Care Supporting Process

FIG. 3 is a diagram showing outline of the care supporting process in the nursing learning support system 1.

In any of the terminals 10 to 40, when the user selects one or more symptoms or enters one or more symptoms in a natural sentence, with reference to the medical DB 110 by the searching function of the server 100, the disease name corresponding to the one or more symptoms is detected. Information of the combination of the disease name and the care(s) is obtained from the medical DB 110 and visibly presented in the terminals 10 to 40. When a medical record number is entered from any of the terminals 10 to 40, the server 100 properly and automatically obtains personal information (such as past disease) of the user from the medical record DB 210 communicatably connected by the personal information recognizing function. The obtained information is used for retrieval of the information of the combination between the disease name and the care(s).

In the terminals 10 to 40, when the user designates a desired care in combinations of the disease names and the cares visibly presented, information of a detailed care method corresponding to the care is read from the medical DB 110 and visibly presented in the terminals 10 to 40.

In the case where the user has a question, the user can enter the question in the terminals 10 to 40. When there is an answer to the question in the medical DB 110, the answer is visibly presented in the terminals 10 to 40. Although not shown, when there is no answer in the medical DB 110, an answer is directly sent from an expert or a controller to the terminals 10 to 40. As necessary, by adding the information of the question and the answer to the medical DB 110, the knowledge stored in the medical DB 110 is developed.

Data Stored in Medical DB in Care Supporting Process

Disease-Symptom-Combination DB 111

As described above, in the disease-symptom-combination DB 111, a number of pieces of information obtained by combining at least one disease name element and at least one symptom element (symptom-disease-combination information) are stored.

FIGS. 4 to 7 are diagrams showing a concrete example of the information of the disease-symptom-combination DB 111. In each of FIGS. 4 to 7, due to limitation in the size of the diagram, a table showing a plurality of combinations of disease name elements and symptom elements is divided into four parts.

FIGS. 4 to 7 show relations (combinations) between a plurality of (13 in the example) data elements (disease name elements) of disease name and a plurality of combinations (45 combinations in the embodiment) of symptom elements. The disease names are cold, influenza, adenoiditis, pneumonia, measles, rubella, appendicitis, acute cholecystitis, acute cholangitis, hepatitis B, acute pyelonephritis, salmonellosis, and campylobacter infection). The symptom elements are divided into a plurality of (10 in the example) classifications (whole body, head, bones and muscles, nose, throat, mouth, skin, excretion, abdomen, and eyes).

In FIGS. 4 and 5, numbers 1 to 45 are designated to 45 combinations of the symptom elements which are written line by line in order from top. Concretely, 45 combinations are formed by: symptom elements of main symptom corresponding to 25 rough symptoms (fever, fatigue, chill and rigor, sweating, lymphadenopathy, cyanosis, headache, insomia, joint/muscle pain, runny nose, coughing, expectoration, sore throat, sneeze, dyspnea, rash, jaundice, diarrhea, constipation, nausea/vomiting, urinary disturbance, abdominal pain, loss of appetite, and hyperemia) (hereinbelow, also called "main symptom elements"); and symptom elements indicating one or more detailed symptom (hereinbelow, also called "detailed symptom elements"). The number of detailed symptom elements may be one or more, and the detailed symptom elements properly include region, the degree, period, amount, the number of times, and the time of occurrence.

More specifically, each of 11 main symptoms (fever, sweating, cyanosis, expectoration, sore throat, rash in the mouth, rash in the skin, diarrhea, urinary disturbance, abdominal pain, and hyperemia) is combined with one or more of detailed symptom elements, thereby obtaining 27 combinations of symptom elements. That is, the 45 combinations of symptom elements include the 27 combinations of the symptom elements, each obtained by combining symptom element for a predetermined symptom and one or more detailed symptom elements indicating detail symptom for the predetermined symptom.

For example, the combinations include a combination of the main symptom element of "fever", a detailed symptom element of "high fever", and a detailed symptom element of "short time", and a combination of the main symptom element of "rash", a detailed symptom element of "rear side of ears, face, and top to body trunk and four limbs", the detailed symptom element of "irregular shape", the detailed symptom element of "a few mm to 1 cm", and the detailed symptom element of "red spots/spotty". "→" in the detailed symptom element is equivalent in meaning with "from".

The 14 main symptoms (fatigue, chill and rigor, lymphadenopathy, headache, insomnia, joint/muscle pain, runny nose, coughing, sneeze, dyspnea, jaundice, constipation, nausea/vomiting, and loss of appetite) are not combined with the detailed symptom element. Further, there are four combinations of the symptom elements in which four main symptoms (expectoration, sore throat, diarrhea, and abdominal pain) are not combined with the detailed symptom element.

The combinations of the symptom elements are not limited to those shown in FIGS. 4 and 5. For example, a detailed symptom element of "the body temperature variation in a day is 1° C. or less" may be added to the symptom element "fever", or the detailed symptom elements of the symptom element "fever" may be deleted.

FIGS. 6 and 7 show the relations (combinations) between the 45 symptom element combinations (the numbers 1 to 45 corresponding to the combinations are shown) and the 13 disease name elements. Concretely, a circle sign indicates a match between a disease name element and a symptom element. In the diagrams, a circle sign is shown in a symptom which appears for a disease. For example, with respect to the disease name element "cold", there are 16 combinations of the symptom elements (numbers 3, 5, 7, 8, 10, 12, 14, 15, 16, 17, 19, 21, 27, 31, 34, and 44). For each of the other disease name elements, one or more combinations of symptom elements (in the example, three or more combinations) are shown.

In FIGS. 6 and 7, three kinds of circle signs exist, which are a simple circle sign, a double-circle sign, and a solid circle sign. The circle signs are used to determine whether a disease name is preferentially detected or not in the case where a plurality of disease name elements are likely to be detected for one or more combinations of symptom elements in the detection of disease name element, which will be described later.

Concretely, the circle signs are used for a determination rule. According to the rule, when a certain disease name element matches two combinations of symptom elements marked with the double-circle signs, the disease name element is detected preferentially. When a certain disease name element matches a symptom element combination marked with a solid circle sign, the disease name element is detected preferentially. For example, in the case where the combinations of the symptom elements of Nos. 1 and 14 show the symptom of a patient, although a plurality of disease name elements corresponding to the combinations of the symptom elements of Nos. 1 and 14 exist, the disease name element "influenza" is detected preferentially. In the case where the combination of the symptom elements of No. 23 shows the symptom of a patient, the disease name element "measles" is detected preferentially.

Data can be stored in the disease-symptom-combination DB 111 by proper operation on the operation unit 194 of the management terminal 190 of the controller of the nursing learning support system 1.

Disease-Care-Combination DB 112

FIG. 8 is a diagram showing a concrete example of information of the disease-care-combination DB 112 and shows a case where the symptom is "fever", the disease name is "influenza" or "adenoiditis", and cares are "compress" and "fluid intake".

Each of lines in FIG. 8 shows information of a combination of one or more (four in the example) symptom elements, one disease name element, one personal information element, one detailed care element, and one care element (hereinbelow, also called "symptom-disease-personal information-care combination information"). In the disease-care-combination DB 112, a number of pieces of the symptom-disease-personal information-care-combination information are stored.

Concretely, FIG. 8 shows information of a combination of 10 data elements which are, from the left side in each of lines, a data element of a related symptom such as a symptom accompanying a main symptom (related symptom element), a main symptom element, two data elements indicative of detailed symptoms (in this case, a state and a period) of the main symptom (detailed symptom elements), a disease name element, a data element (personal information element) indicative of personal information (in this case, information of a past disease), a data element showing detailed information of an emergency care method (so-called initial care) (hereinbelow, also called "detailed initial care element"), a data element indicative of a classification of a care method (care classification) (hereinbelow, also called "care classification element"), a care element, and a data element indicative of detailed information of a care (detailed care element). To the detailed care element, a number specifying the detailed care element (hereinbelow, called "detailed care specifying number") is given in FIG. 8. In the detailed data group 115 which will be described later, information is stored in such a manner that the actual detailed care elements are associated with the detailed element specifying numbers.

For example, FIG. 8 shows: information of a combination of the related symptom element "none", the main symptom element "fever", the detailed symptom element "high fever", the detailed symptom element "short time", the disease name element "influenza", the personal information element "none", the initial care detailed element "consult a doctor", the care classification element "procedure", the care element "compress (to warm or cool)", and the detailed element specifying number "1"; information of a combination of the related symptom element "chill and rigor (cold and shaking)", the main symptom element "fever", the detailed symptom element "high fever", the detailed symptom element "short time", the disease name element "adenoiditis", the personal information element "diabetes", the initial care detailed element "consult a doctor", the care classification element "procedure", the care element "fluid intake", and the detailed element specifying number "16", and the like.

That is, the disease-care-combination DB 112 stores information of combinations between a plurality of disease name elements (for example, 13 disease name elements described in FIGS. 6 and 7) and a plurality of care elements corresponding to the disease name elements. The disease-care-combination DB 112 also includes information of a combination between each of the care elements and one or more detailed care elements as detailed information of the caring method (detailed element combination information).

From another viewpoint, the detailed element combination information includes information of a combination of at least one personal information element which shows at least personal information, the care element, and one or more detailed care elements and also includes information of a combination of at least one symptom element, the care element, and one or more detailed care elements. Since each of the care elements is combined with the detailed initial care element indicative of the details of an emergency caring method and the detailed care element indicative of the details of a caring method, it can be also said that each care element is combined with a plurality of detailed care elements as detailed information of a plurality of kinds of caring methods.

FIG. 8 illustrates the information of the past disease as personal information. The present invention is not limited to the information. For example, at least one of information indicating whether the patient is taking medicine or not and information indicating whether the patient has allergy or not may be properly employed as personal information.

Although FIG. 8 shows "procedure" for a disease as the care classification, the invention is not limited to "procedure". At least one of items of "treatment", "treating method", "follow-up", "initial care", "medicine", and "test" corresponding to a disease may be properly employed. That is, the caring methods properly include the "treatment", "caring method", "follow-up", "initial care", "medicine", and "test".

In FIG. 8, each piece of the symptom-disease-personal information-care-combination information includes one care element. The invention is not limited to the case. When the care elements are grouped by a care name in a broader term, the care elements may be expressed hierarchically so that two or more care elements are properly included in each symptom-disease-personal information-care-combination information. When such care elements are expressed hierarchically, one or more detailed care elements are associated with a care element in a narrower term.

The data can be stored in the disease-care-combination DB 112 by proper operation on the operation unit 194 of the management terminal 190 of the controller of the nursing learning support system 1.

The disease-symptom DB 113

The disease-symptom DB 113 stores information of a combination between each of the disease name elements and one or more symptom elements including a main symptom element unconditionally determined according to the disease name element. For example, in the case of appendicitis, when it is a known fact that the body temperature variation in one day is 1° C. or less at the occurrence of fever, the fact is stored in the disease-symptom DB 113. That is, the predetermined disease name element "appendicitis" is stored in combination with the main symptom element "fever" and the detailed symptom element "body temperature variation of 1° C. or less in a day" of the main symptom element "fever".

As also shown in FIGS. 6 and 7, each disease has various symptoms, and there are a number of symptoms common to a plurality of diseases, and only a part of the symptom elements is unconditionally determined for a disease name element. Therefore, in the disease-symptom DB 113, symptom elements of items as a part of a predetermined number of items of symptom elements requested to be entered in order to detect a disease name element and a care element by an input requesting unit 102B which will be described later are combined with each of the disease name elements.

Data can be stored in the disease-symptom DB 113 by proper operation on the operation unit 194 of the management terminal 190 of the controller of the nursing learning support system 1.

Detailed Data Group 115

FIGS. 9 and 10 are diagrams showing a concrete example of information of the detailed data group 115.

FIG. 9 shows a state where a plurality of (seven in FIG. 9) detailed care elements related to the care element "(cold or hot) compress" are stored in association with detailed element specifying numbers (1 to 7 in FIG. 9). For example, a detailed care element "Cool the regions where arteries extend such as the forehead, underarms, the neck, and the groin with an ice bag, a cold pack, an ice pillow, or the like. Be careful not to cool the same region for more than one hour" of the care element "(cold or hot) compress" is stored in association with the detailed element specifying number "1". The detailed care elements are stored so as to be associated with the other detailed element specifying numbers "1 to 7" in a similar manner. The detailed element specifying number shown in FIG. 9 corresponds to the detailed element specifying number shown in FIG. 8. That is, the care element "(cold or hot) compress" in FIG. 8 and the detailed care elements are combined in association with the detailed element specifying number.

FIG. 10 shows a state where a plurality of (three in FIG. 10) detailed care elements related to the care element "fluid intake" are stored in association with detailed element specifying numbers (11 to 13 in FIG. 10). For example, a detailed care element "When you have a fever, fluid becomes insufficient due to sweating or the like, so that take sufficient fluid. Since electrolyte also tends to be insufficient, drink water and, preferably, a sports drink including electrolyte" of the care element "fluid intake" is stored in association with the detailed element specifying number "11". The detailed care elements are stored so as to be associated with the other detailed element specifying numbers "11 and 12" in a similar manner. The detailed element specifying number shown in FIG. 10 corresponds to the detailed element specifying number shown in FIG. 8. That is, the care element "fluid intake" in FIG. 10 and the detailed care elements are combined in association with the detailed element specifying number.

Functional Configuration of Nursing Supporting Process
Functions of Terminal Control Unit 12

FIG. 11 is a diagram showing the functions realized by the terminal control unit 12 when the nursing supporting process is executed. When the nursing supporting process is executed, the terminal control unit 12 has, as functions, an input/output control unit 12A, an input information receiving unit 12B, a care designating unit 12C, an adopted care designating unit 12D, and a measurement value obtaining unit 12E.

The input/output control unit 12A controls information sent from the server 100 or the like so as to be visibly output to the display unit 13. For example, the input/output control unit 12A visibly outputs disease-care information (which will be described later) or the like in which a disease name element and a plurality of care elements are combined to the display unit 13. The input/output control unit 12A properly controls data transmission via the I/F 15.

The input information receiving unit 12B receives various information entered from the operation unit 14 in response to an input operation on the operation unit 14 of the user.

In response to a predetermined input operation on the operation unit 14 of the user in a state where the disease care information is visibly output in the display unit 13 under control of the input/output control unit 12A, the care designating unit 12C designates one of a plurality of care elements included in the disease care information (which will be described later) as a care element whose detailed care elements are to be displayed. The information of the care element designated by the care designating unit 12C is transmitted to the server control unit 102 (concretely, a detailed information detecting unit 102K to be described later) by the input/output control unit 12A.

In response to the predetermined input operation on the operation unit 14 of the user in a state where detailed care elements of the care element designated by the care designating unit 12C are visibly output in the display unit 13, the adopted care designating unit 12D designates the care element designated by the care designating unit 12C as a data element indicative of the care adopted by the user (hereinbelow, also called "adopted care element"). The information of the adopted care element designated by the adopted care designating unit 12D is transmitted to the server control unit 102 (concretely, a medical record information description control unit 102L to be described later) by the input/output control unit 12A.

In response to a predetermined input operation on the operation unit 14 of the user, the measurement value obtaining unit 12E obtains information of a measurement value of a parameter (for example, a value of body temperature, blood pressure, or the like) of a health state of a patient (hereinbelow, also called "measurement value information"). The measurement value information obtained by the measurement value obtaining unit 12E is transmitted to the server control unit 102 (concretely, the medical record information description control unit 102L which will be described later) by the input/output control unit 12A.

Functions of Server Control Unit 102

Figure 12:
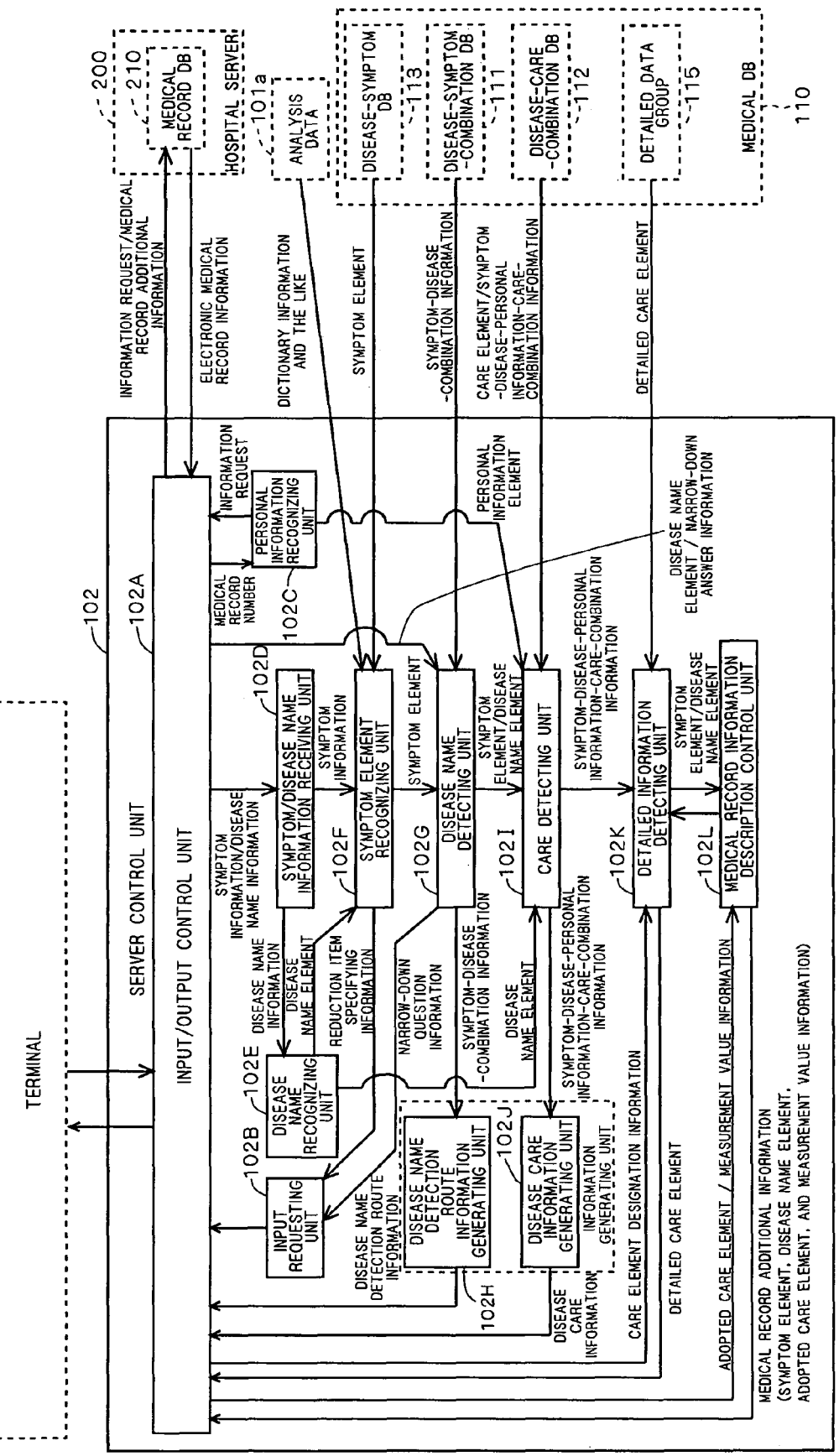
FIGS. 12 and 13 are block diagrams showing functions realized by a server control unit.
Figure 13:
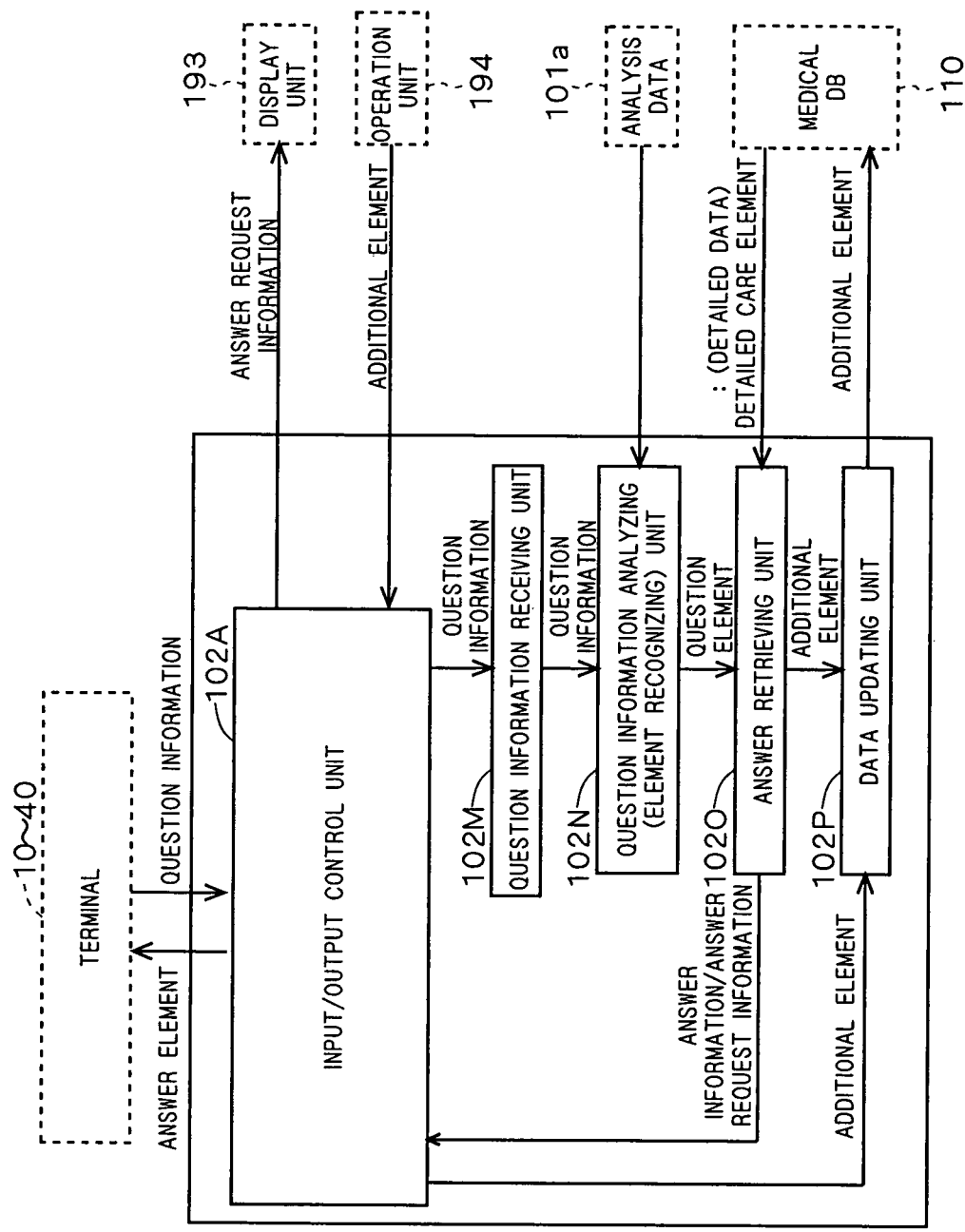

FIGS. 12 and 13 are diagrams illustrating functions realized by the server control unit 102 when the nursing supporting process is executed.

At the time of executing the nursing supporting process, the server control unit 102 has, as functions, an input/output control unit 102A, the input requesting unit 102B, a personal information recognizing unit 102C, a symptom/disease name information receiving unit 102D, a disease name recognizing unit 102E, a symptom element recognizing unit 102F, a disease name detecting unit 102G, a disease name detection route information generating unit 102H, a care detecting unit 102I, a disease care information generating unit 102J, the detailed information detecting unit 102K, the medical record information description control unit 102L, a question information receiving unit 102M, a question information analyzing unit 102N, an answer retrieving unit 102O, and a data updating unit 102P.

First, the functions shown in FIG. 12 will be described.

The input/output control unit 102A controls data transmission/reception via the I/F 105.

The input requesting unit 102B requests the terminals 10 to 40 and the like via the input/output control unit 102A or the like to enter various information. For example, to retrieve a disease name and a caring method, the input requesting unit 102B transmits information of a request to enter symptom information indicative of a symptom in a natural sentence and/or symptom elements of a predetermined number of items (necessary items) necessary to specify a disease name element. When information specifying some items (hereinbelow, also called "reduction item") which does not require an entry of a symptom element from the predetermined number of items (hereinbelow, also called "reduction item specifying information") is entered from the symptom element recognizing unit 102F (which will be described later), the input requesting unit 102B transmits information requesting an entry of symptom elements corresponding to the items remained after excluding the reduction item from the predetermined number of items.

On the basis of location specifying information specifying location of personal information (for example, a medical record number specifying the location of electronic medical record information of the user) entered by an operation on the operation unit 14 of the user in the terminals 10 to 40, the personal information recognizing unit 102C recognizes a data element (personal information element) indicative of personal information stored in the medical record DB 210 of the hospital server 200. When the personal information element is directly entered by an operation on the operation unit 14 in the terminals 10 to 40, the personal information recognizing unit 102C recognizes the personal information element as it is. The personal information recognizing unit 102C outputs the recognized one or more personal information elements to the care detecting unit 102I.

The symptom/disease name information receiving unit 102D receives information of a symptom (hereinbelow, also called "symptom information") and information of a disease name (disease name information) entered by an operation on the operation unit 14 of the user in the terminals 10 to 40 and transmitted via the input/output control unit 102A or the like. Examples of the symptom information are information of one or more symptom elements and information indicative of a symptom in a natural sentence. An example of the disease name information is a symptom name element. The symptom/disease name information receiving unit 102D transmits the disease name information to the disease name recognizing unit 102E and transmits the symptom information to the symptom element recognizing unit 102F. Discrimination between the symptom information and the disease name information is performed by, for example, clearly dividing timings at which the two pieces of information are entered from each other or giving identification information to each of the two pieces of information.

The disease name recognizing unit 102E recognizes one data element (disease name element) indicative of a disease name from the disease name information received from the symptom/disease name information receiving unit 102D. For example, when the disease name information is constructed by a single disease name element, the disease name recognizing unit 102E recognizes the disease name element. For example, a table in which information (such as numbers) for specifying disease name elements are associated with the disease name elements is prepared. When a number is entered as disease name information, the disease name recognizing unit 102E recognizes the corresponding disease name element from the number. As described above, various modes can be employed. The disease name recognizing unit 102E outputs the recognized disease name element to the disease element recognizing unit 102F and the care detecting unit 102I.

The symptom element recognizing unit 102F recognizes one or more symptom elements each indicative of a symptom from the symptom information received from the symptom/disease name information receiving unit 102D. The symptom element recognizing unit 102F transmits the recognized one or more symptom elements to the disease name detecting unit 102G.

For example, when the symptom information is constructed by one or more symptom elements, the symptom element recognizing unit 102F recognizes the symptom element. For example, a table in which information (such as numbers) for specifying symptom elements is associated with the symptom elements is prepared. When a number is entered as symptom information, the symptom element recognizing unit 102F recognizes the corresponding symptom element from the number.

In the case where the symptom information is information indicating a symptom written in a natural sentence, the symptom element recognizing unit 102F recognizes one or more symptom element by performing a predetermined language analyzing process using data for morphological analysis, data for dependency structure analysis, keyword data, and dictionary data on the natural sentence. For example, first, a process of so-called morphological analysis is performed by using the data for morphological analysis to disassemble the natural sentence to morphemes. Next, a modification relation is recognized by a process of the so-called dependency structure analysis using the data for dependency structure analysis, and a term or paragraph indicative of a symptom is recognized by using the keyword data. Finally, with the dictionary data, a synonym or the like is replaced with a representative term or the like. In this case, the keyword data may be data of a list of symptom elements included in the disease-symptom-combination DB 111.

Further, in the case where the disease name element is entered to the symptom element recognizing unit 102F in response to recognition of the disease name element by the disease name recognizing unit 102E, the symptom element recognizing unit 102F recognizes one or more symptom elements for some items combined with the disease name element in the disease-symptom DB 113. In this case, the symptom element recognizing unit 102F transmits, as a reduction item which does not require an entry of a symptom element, reduction item specifying information that specifies reduction items of symptom elements unconditionally recognized from one disease name element as a part of a predetermined number of items of symptom elements which are to request an entry of a symptom element to the input requesting unit 102B.

With reference to the disease-symptom-combination DB 111, the disease name detecting unit 102G detects a disease name element combined with all of the one or more symptom elements recognized by the symptom element recognizing unit 102F in the disease-symptom-combination DB 111.

For example, when the combination of the symptom elements of numbers 1, 3, 5, 7, 12, 14, 15, and 16 shown in FIG. 6 is recognized by the disease name recognizing unit 102E, the disease name element "influenza" combined with all of the symptom elements recognized is detected. As shown by the various kinds of circle signs in FIG. 6, one disease name element is detected by the disease name detecting unit 102G while using also information of a criterion for determining whether one disease name in the disease-symptom-combination DB 111 is preferentially detected or not. The disease name detecting unit 102G detects all of the symptom-disease-combination information including both of the combinations of recognized symptom elements and the detected one disease name element from the disease-symptom-combination DB 111, and transmits the detected information to the disease name detection route information generating unit 102H. The disease name detecting unit 102G transmits the detected one disease name element and one or more symptom elements input from the symptom element recognizing unit 102F to the care detecting unit 102I.

Further, in the case where the disease name detecting unit 102G cannot narrow down detection to one disease name element, that is, in the case where a plurality of disease name elements are detected, the disease name detecting unit 102G transmits information of a question for narrowing down the plurality of disease name elements to one disease name element (hereinbelow, also called "narrow-down question information") to the input requesting unit 102B. For example, it is sufficient to pre-set the narrow-down question information for each of a plurality of combinations of disease name elements and store it in the storing unit 101. Answer information for the narrow-down question information (hereinbelow, also called "answer information for narrow down") is transmitted from the terminals 10 to 40 to the disease name detecting unit 102G via the input/output control unit 102A. The disease name detecting unit 102G detects one disease name element on the basis of the answer information for narrow down. To realize such a process, it is sufficient to store a combination of a plurality of disease name elements, narrow-down question information, answer information for narrow down, and a narrow-down result (one disease name element or a plurality of disease name elements) so as to be associated with each other in the storing unit 101.

The disease name detection route information generating unit 102H combines the one or more symptom elements recognized by the symptom element recognizing unit 102F with one disease name element detected by the disease name detecting unit 102G, thereby generating information indicative of a route of detecting the one disease name element (hereinbelow, also called "disease name detection route information"). Concretely, on the basis of all of symptom-disease-combination information pieces entered from the disease name detecting unit 102G, the disease name detection route information generating unit 102H generates disease name detection route information by associating one or more combinations of symptom elements included in each of the symptom-disease-combination information pieces with one disease name element common to all of the symptom-disease-combination information pieces. The disease name detection route information is transmitted to the terminals 10 to 40 via the input/output control unit 102A and the like. In the terminals 10 to 40, under control of the input/output control unit 12A, the disease name detection route information is visibly output in the display unit 13.

The care detecting unit 102I detects a plurality of care elements combined with one disease name element in the disease-care-combination DB 112. Concretely, in the case where one disease name element is input from the disease name detecting unit 102G, a plurality of care elements combined with the disease name element detected by the disease name detecting unit 102G are detected from the disease-care-combination DB 112. On the other hand, in the case where one disease name element is input from the disease name recognizing unit 102E, a plurality of care elements combined with the disease name element recognized by the disease name recognizing unit 102E are detected from the disease-care-combination DB 112.

For example, in the case where a number of pieces of the symptom-disease-personal information-care-combination information are stored in the disease-care-combination DB 112 as shown in FIG. 8, the care detecting unit 102I extracts a plurality of pieces of symptom-disease-personal information-care-combination information including a combination of one disease name element, one or more symptom elements, and one or more personal information elements obtained by the disease name recognizing unit 102E, the disease name detecting unit 102G, or the personal information recognizing unit 102C, thereby detecting a plurality of care elements included in the plurality of pieces of symptom-disease-personal information-care-combination information. The care detecting unit 102I transmits the extracted plurality of pieces of symptom-disease-personal information-care-combination information to the disease care information generating unit 102J.

The disease care information generating unit 102J generates information (hereinbelow, also called "disease care information") obtained by combining one disease name element detected by the disease name detecting unit 102G and the plurality of care elements detected by the care detecting unit 102I. Concretely, on the basis of a plurality of pieces of symptom-disease-personal information-care-combination information obtained from the care detecting unit 102I, the disease care information generating unit 102J makes information obtained by combining one or more symptom elements, one or more personal information elements, and the care element included in each of the symptom-disease-personal information-care-combination information pieces depend on one disease name element common to a plurality of pieces of symptom-disease-personal information-care-combination information, thereby generating the disease care information. The disease care information is transmitted to the terminals 10 to 40 via the input/output control unit 102A or the like. At this time, in the terminals 10 to 40, the disease care information is visibly output in the display unit 13 under control of the input/output control unit 12A.

The detailed information detecting unit 102K obtains information of the care element designated by the care designating unit 12C in the terminals 10 to 40, and detects one or more detailed care element (in this example, one detailed care element) corresponding to the care element from the detailed data group 115.

As shown in FIG. 8, in the disease-care-combination DB 112, a detailed element specifying number is given to each of the care elements. As shown in FIGS. 9 and 10, a detailed care element is associated with each of the detailed element specifying numbers in the detailed data group 115. Consequently, the detailed information detecting unit 102K detects one or more detailed care elements combined with the care element designated by the care designating unit 12C in the terminals 10 to 40 in the disease-care-combination DB 112 from the detailed data group 115.

In the case where the disease-symptom-combination DB 111 has information as shown in FIG. 8, if the combination of symptom elements or the personal information element vary, detailed care elements combined with each care element vary in the disease-care-combination DB 112. In such a case, the detailed information detecting unit 102K detects one or more detailed care element combined with one care element designated by the care designating unit 12C in the terminals 10 to 40, one or more symptom elements recognized by the symptom element recognizing unit 102F, and one or more personal information elements recognized by the personal information recognizing unit 102C in the disease-care-combination DB 112. In other words, one or more detailed care elements combined with both of one care element and one or more symptom elements are detected, and one or more detailed care elements combined with both of one care element and one or more personal information elements are detected.

The detailed information detecting unit 102K transmits the detected one or more detailed care element to the terminals 10 to 40 via the input/output control unit 102A or the like. At this time, in the terminals 10 to 40, under control of the input/output control unit 12A of the terminal control unit 12, the detailed information of the caring method is visibly output in the display unit 13 on the basis of one or more detailed care elements from the detailed information detecting unit 102K. The detailed information visibly output is detailed information of a caring method corresponding to one care element designated by the care designating unit 12C in the terminals 10 to 40.

Further, in response to a request from the medical record information description control unit 102L, the detailed information detecting unit 102K transmits one or more symptom elements and one disease name element included in each of the symptom-disease-personal information-care combination information received from the care detecting unit 102I to the medical record information description control unit 102L.

The medical record information description control unit 102L controls so as to describe one disease name element detected on the basis of the input symptom, one or more symptom elements used at the time of detecting one disease name element, the care element employed by the user, and the measurement value information of a parameter of the patient into the medical record DB 210 in the hospital server 200.

Concretely, when the medical record information description control unit 102L receives one adopted care element from the adopted care designating unit 12D in the terminals 10 to 40 and receives the measurement value information from the measurement value obtaining unit 12E, the medical record information description control unit 102L requests the detailed information detecting unit 102K to transmit one or more symptom elements and one disease name element. The one or more symptom elements and one disease name element correspond to the elements recognized by the symptom element recognizing unit 102F and those detected by the disease name detecting unit 102G. When one or more symptom elements and one disease name element are obtained from the detailed information detecting unit 102K, the one disease name element, one or more symptom elements, one adopted care element, and measurement value information are transmitted as information to be added to the electronic medical record information (hereinbelow, also called "medical recorded addition information") to the hospital server 200 via the input/output control unit 102A or the like.

In the hospital server 200, by the control of the control unit 202, the medical record addition information is written in the medical record DB 210 in the storing unit 201. The electronic medical record information to which the medical record addition information is to be added is discriminated by any of various modes such as a mode using the medical record number obtained by the personal information recognizing unit 102C.

The functions shown in FIG. 13 will now be described.

The question information receiving unit 102M receives information indicative of a question (hereinbelow, also called "question information") entered by an operation on the operation unit 14 of the user in the terminals 10 to 40 via the input/output control unit 102A and the like. A case where the question information is written in a natural sentence will be described. The question information receiving unit 102M transmits the received question information to the question information analyzing unit 102N.

The question information analyzing unit 102N performs a predetermined language analyzing process on the question information, thereby recognizing a data element indicative of the question including at least one (that is, one or more) care element. In the predetermined language analyzing process, like the symptom element recognizing unit 102F, a predetermined language analyzing process using data for morphological analysis, data for dependency structure analysis, keyword data, and dictionary data is performed on the natural sentence, thereby recognizing one or more care elements. In this case, the keyword data may be data of a list of care elements included in the disease-care-combination DB 112.

The answer retrieving unit 102O searches the medical DB 110 (in this case, the disease-care-combination DB 112) for a detailed care element corresponding to at least one care element recognized by the question information analyzing unit 102N. When one or more care elements recognized by the question information analyzing unit 102N is included in the symptom-disease-personal information-care-combination information extracted by the care detecting unit 102I, the answer retrieving unit 102O obtains the detailed care element corresponding to the one care element from the detailed data group 115. The detailed care element is transmitted as information indicative of an answer (answer information) to the terminals 10 to 40 via the input/output control unit 102A or the like. In the terminals 10 to 40, the answer information is visibly output in the display unit 13 under control of the input/output control unit 12A.

On the other hand, when the one or more care elements recognized in the question information analyzing unit 102N is not included in the symptom-disease-personal information-care-combination information extracted by the care detecting unit 102I, the answer retrieving unit 102O recognizes the one care element as a new care element and transmits it as a data element to be added to the disease-care-combination DB 112 (hereinbelow, called "additional element") to the data updating unit 102P. Since answer information to the question information is not obtained from the disease-care-combination DB 112, the answer retrieving unit 102O transmits information of a request for transmitting answer information to the question information to the user (answer request information) to the input/output control unit 102A. Under control of the input/output control unit 102A and the PC control unit 192, the answer request information is visibly output in the display unit 193.

The data updating unit 102P adds the additional element from the answer retrieving unit 102O or one or more additional elements transmitted from the terminals 10 to 40 to the disease-care-combination DB 112. That is, the data updating unit 102P adds one or more additional elements (in this case, a new care element) to the plurality of care elements combined with the disease name elements in the disease-care-combination DB 112. One or more additional elements transmitted from the terminals 10 to 40 are input by an operation of the user on the operation unit 14. In this case, the data updating unit 102P adds an additional element to the disease-care-combination DB 112 so that an additional element (new care element) is added to the symptom-disease-personal information-care-combination information extracted by the care detecting unit 102I.

Operations related to Nursing Supporting Process

Figure 14:
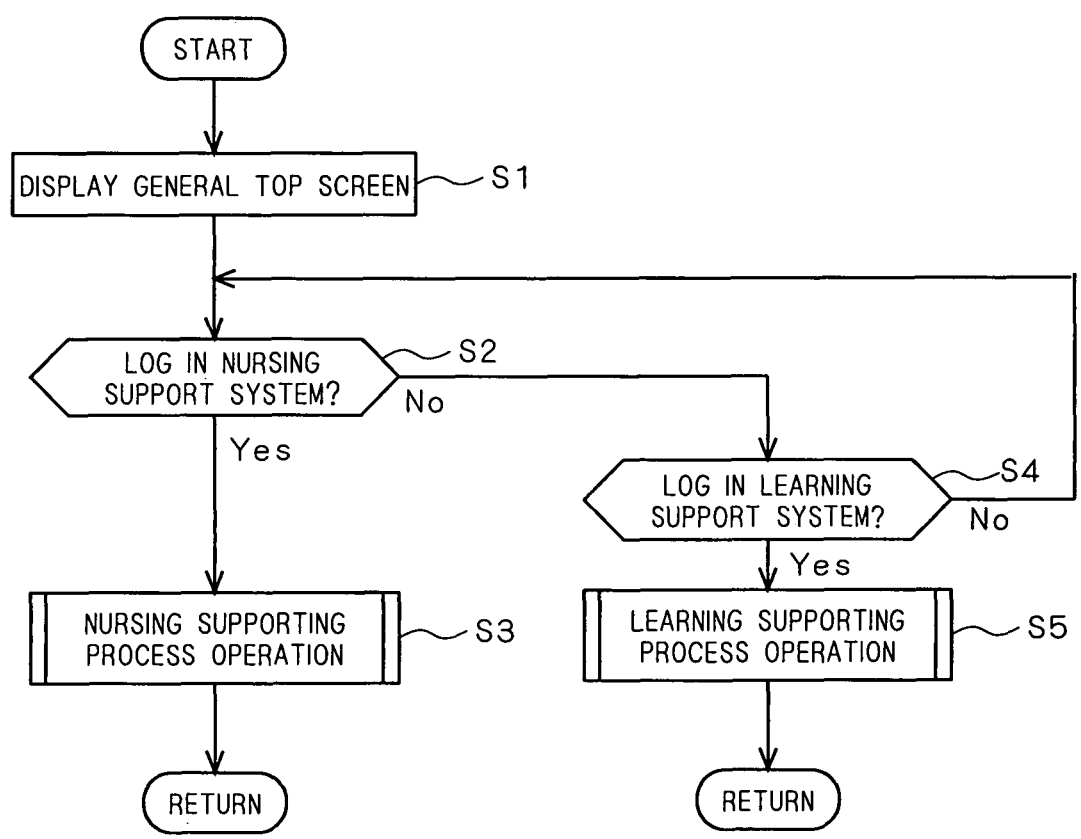
FIG. 14 is a flowchart showing the operation flow of a nursing learning support system.
Figure 15:
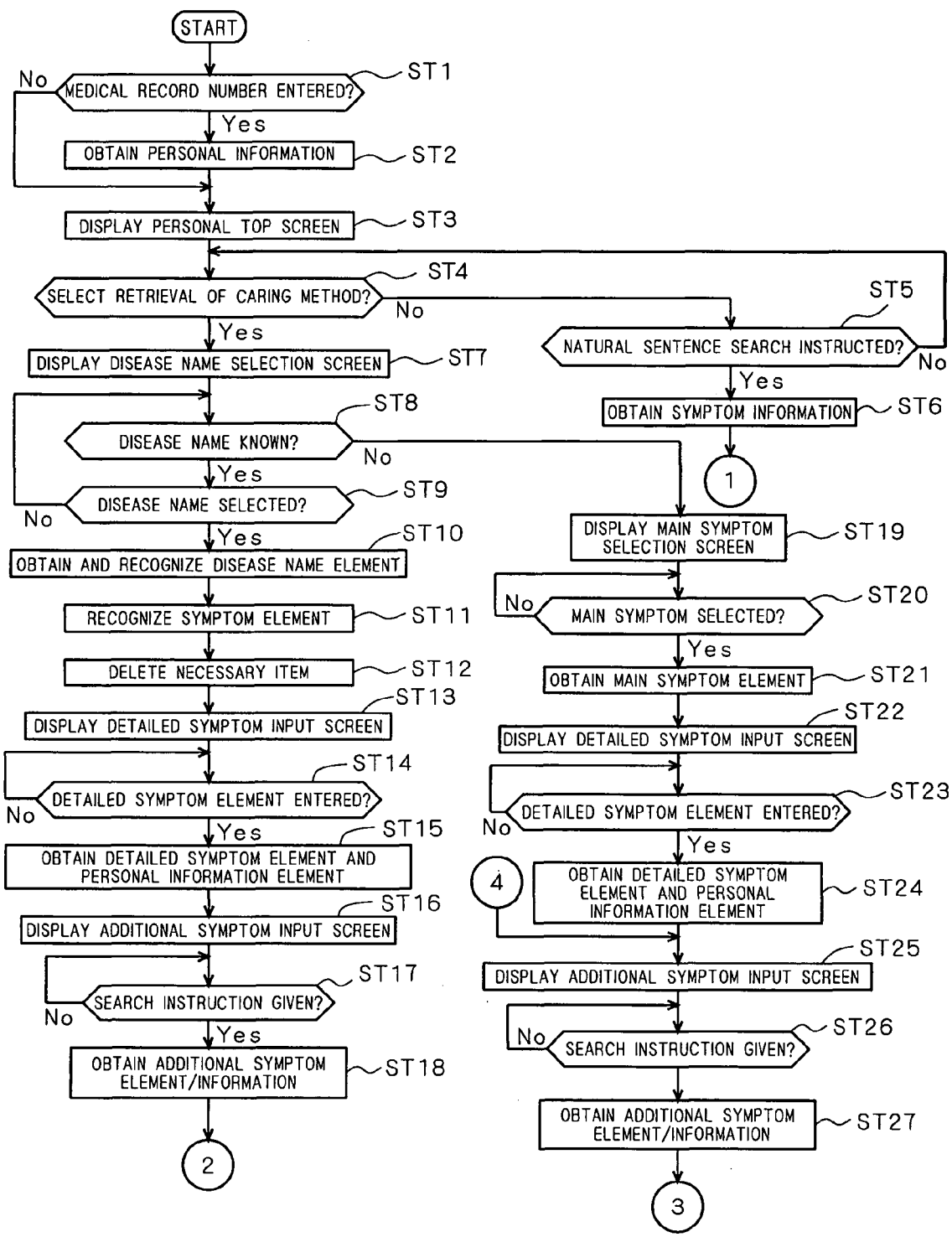
FIGS. 15 to 17 are flowcharts showing the operation flow of a nursing supporting process.
Figure 16:
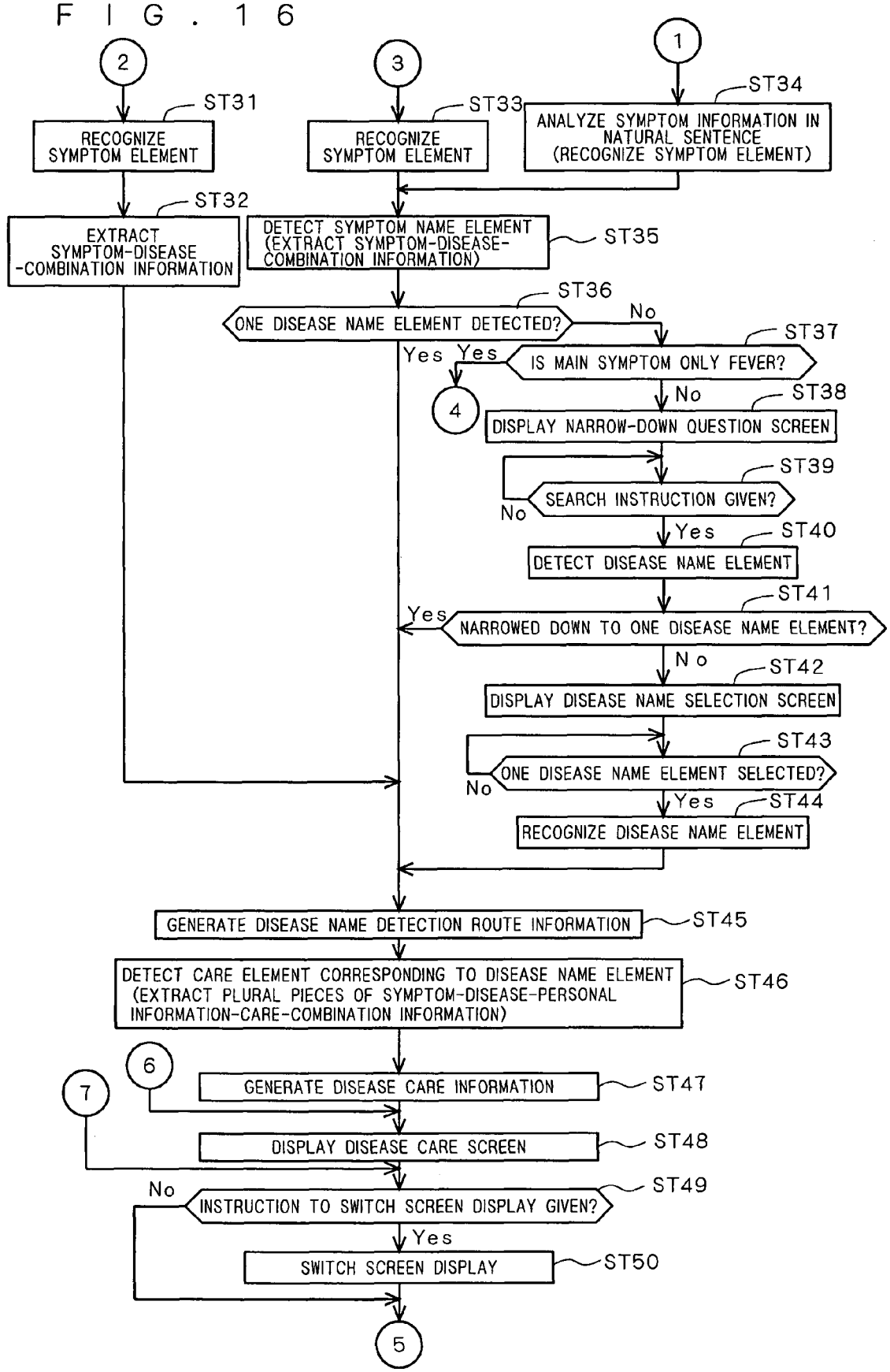
Figure 17:
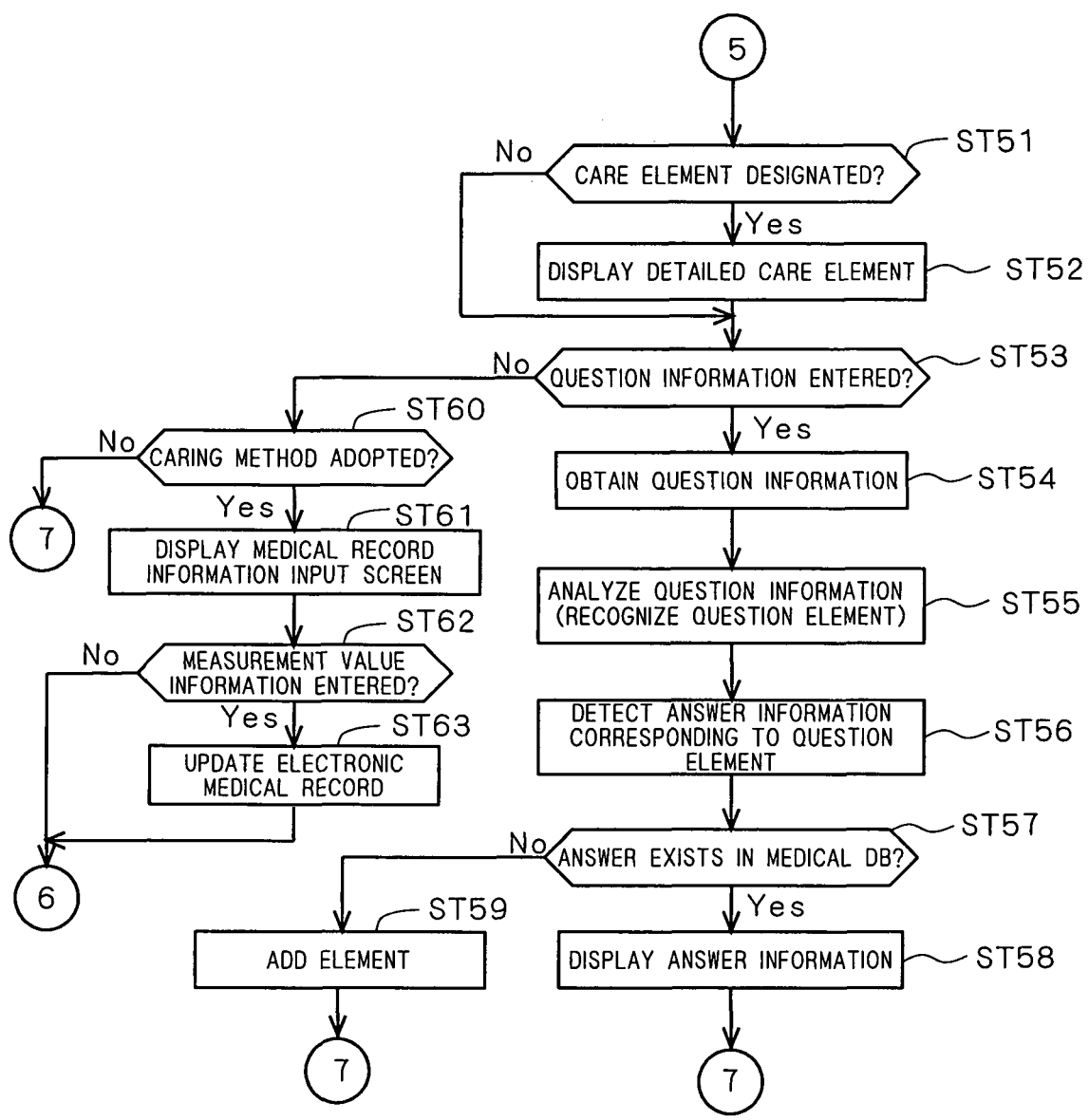

FIG. 14 is a flowchart showing the operation flow for starting operations of the nursing supporting process (nursing supporting process operations) in the nursing learning support system 1. FIGS. 15 to 17 are flowcharts showing the flow of the nursing supporting process operations. FIGS. 18 to 27, FIGS. 30 to 33, and FIG. 35 are diagrams illustrating screens visibly presented in the terminals 10 to 40 in the nursing supporting process operations. In the following, an example in which the user uses the nursing learning support system 1 in the terminal 10 as one of the terminals 10 to 40 will be described.

The operation flow shown in FIG. 14 starts when the function of the nursing learning support system 1 is started by an operation of the user on the operation unit 14 in the terminal 10, and routine advances to step S1.

In step S1, by the server control unit 102 and the input/output control unit 12A, a screen as the entrance (hereinbelow, also called "general top screen") of the nursing learning support system 1 is displayed.

Figure 18:
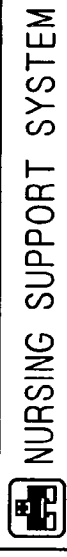
FIG. 18 is a diagram illustrating a general top screen of the nursing learning support system.

FIG. 18 is a diagram showing a general top screen G1. As shown in FIG. 18, in the general top screen G1, when the user enters "name", "ID", and "password" to boxes in a left lower area A1 by operating the operation unit 14 and clicks a log-in button LB1 with a mouse pointer MP, the user can log in an at-home nursing/care supporting system (hereinbelow, called "nursing support system"). On the other hand, when the user enters "name", "ID", and "password" to boxes in a lower right area A2 and clicks a log-in button LB2 with the mouse pointer MP, the user can log in a nursing e-learning system (hereinbelow, called "learning support system").

In general top screen G1, when the user has a patient registration card issued by a hospital as a member of the system, by entering a medical record number written in the card in addition to "name", "ID", and "password", electronic medical record information can be read. In operations of the nursing supporting process, the server control unit 102 can automatically read personal information such as a past disease from the electronic medical record information. In response to entry of the medical record number, the number of symptom entry boxes to be described later is reduced.

In step S2, whether an instruction to log in the nursing support system is given or not is determined by the server control unit 102. When the instruction to log in the nursing support system is given, the routine advances to step S3 and operation of the nursing supporting process is executed. On the other hand, when the instruction to log in the nursing support system is not given, the routine advances to step S4.

In step S4, whether the instruction to log in the learning support system is given or not is determined by the server control unit 102. When the instruction to log in the learning support system is not given, the routine returns to step S2. On the other hand, when the instruction to log in the learning support system is given, the routine advances to step S5, and operation of the learning supporting process (learning supporting process operation) is executed.

With reference to FIGS. 19 to 35, the flow of the nursing supporting process operation shown in FIGS. 15 to 17 will be described. The learning supporting process operation will be described later.

In step S3, the flow of the nursing supporting process operation shown in FIGS. 15 to 17 starts, and the routine advances to step ST1.

In step ST1, whether a medical record number is entered in the general top screen G1 or not is determined by the personal information recognizing unit 102C. When it is determined that a medical record number is entered, the routine advances to step ST2. When it is determined that a medical record number has not been entered, the routine advances to step ST3. When a medical record number as information specifying the location of electronic medical record information of the user including various personal information such as a past disease, age, sex, and the like (location specifying information) is entered in the terminal 10, the personal information recognizing unit 102C obtains the medical record number via the input/output control unit 102A or the like.

In step ST2, the personal information recognizing unit 102C obtains electronic medical record information corresponding to the medical record number entered by the user in the medical record DB 210, and analyzes the electronic medical record information, thereby recognizing and obtaining data elements (personal information elements) indicative of the personal information (information such as sex, age, a past disease, and the like). The personal information recognizing unit 102C requests the hospital server 200 to transmit the electronic medical record information on the basis of the input medical record number. The electronic medical record information is transmitted from the hospital server 200 to the server 100 via the input/output control unit 102A and the like. The personal information recognizing unit 102C recognizes one or more data elements (personal information elements) indicative of the personal information such as the past disease, age, and sex from the electronic medical record information.

In step ST3, the personal top screen of the nursing support system is displayed by the server control unit 102 and the terminal control unit 12.

Figure 19:
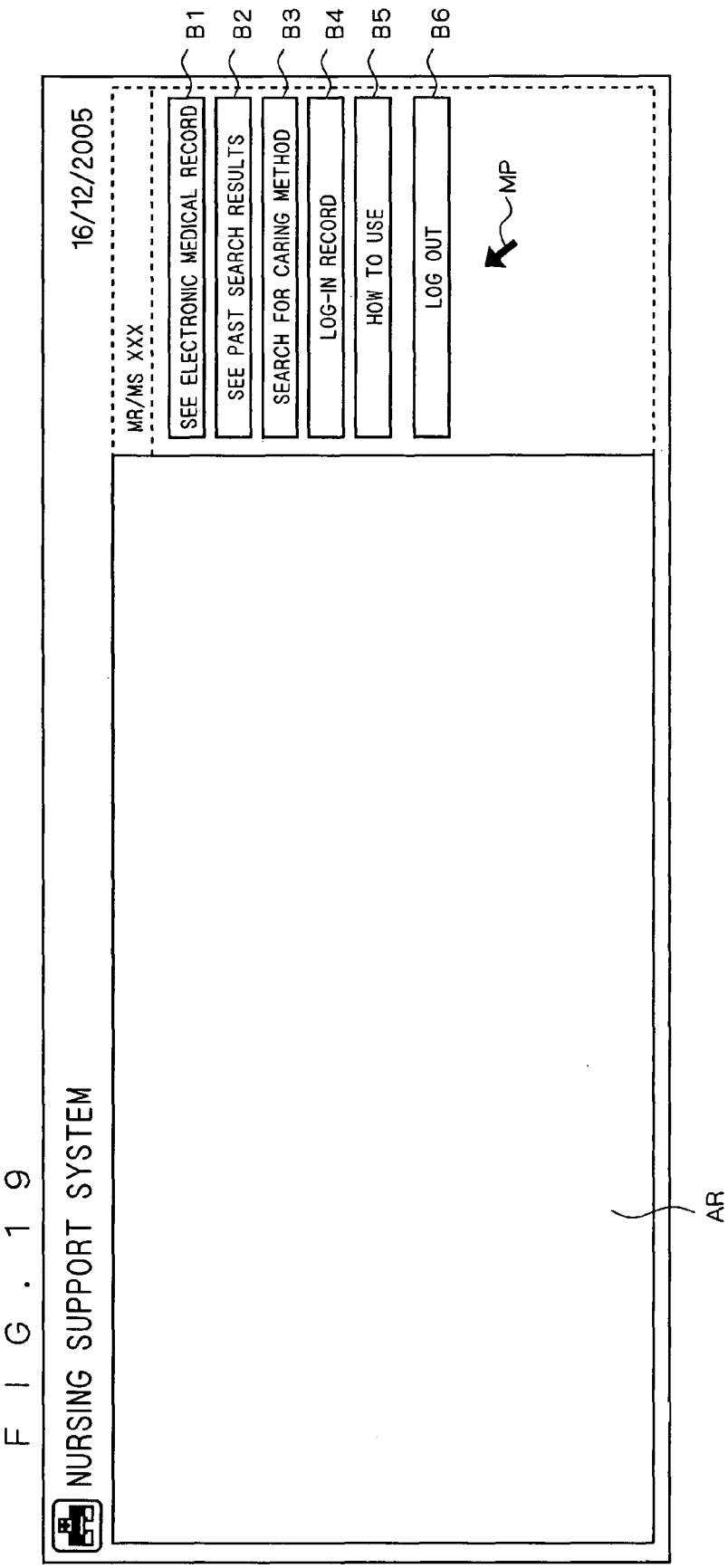
FIG. 19 is a diagram showing the configuration of a display screen of a nursing support system.

FIG. 19 is a diagram showing a screen G2 displayed on the display unit 13 (hereinbelow, also called "nursing support screen") after log-in of the nursing support system. A wide area extending in the center and a left portion in the nursing support screen G2 is an area (support information display area) AR in which various nursing support information is displayed. On the right part of the nursing support screen G2, command buttons B1 to B6 in which various commands can be entered are arranged in order from top.

Figure 20:
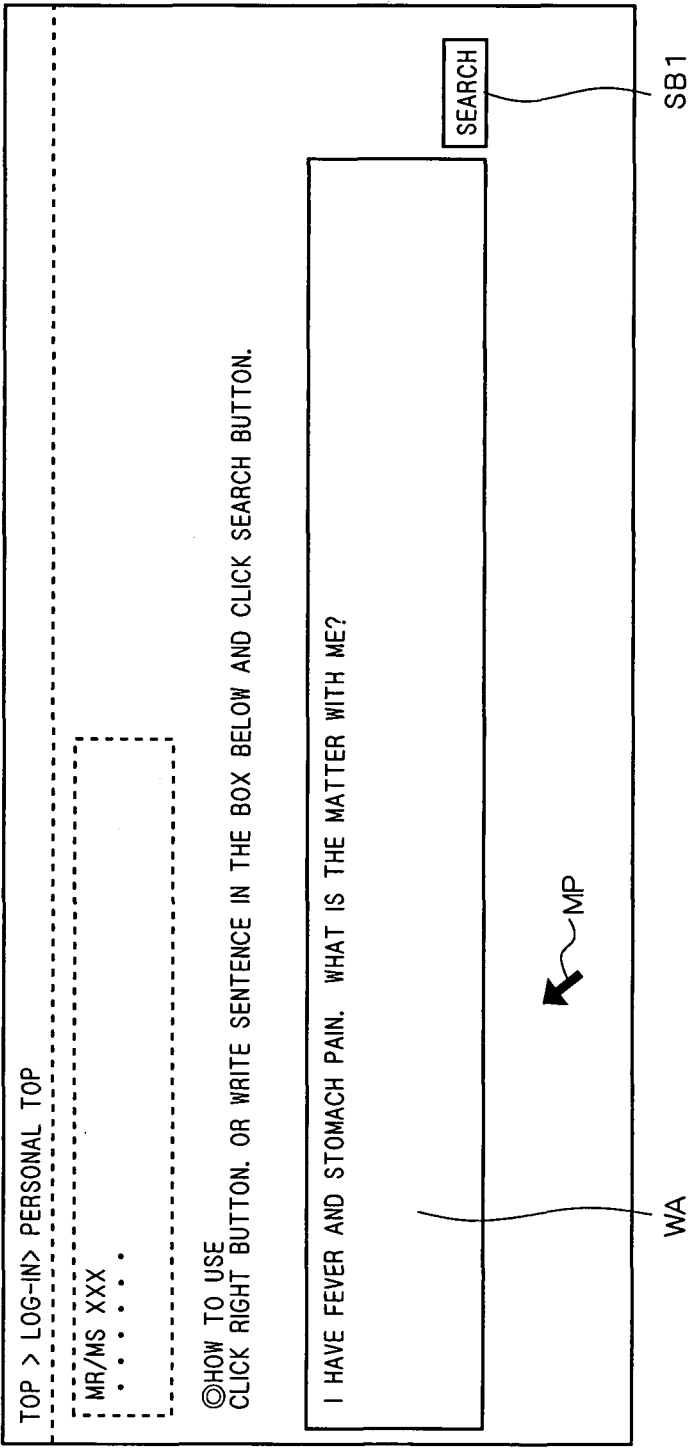
FIG. 20 is a diagram showing a personal top screen of the nursing support system.

FIG. 20 is a diagram showing a screen (hereinbelow, also called "personal top screen") ARa displayed in the support information display area AR in the nursing support screen G2 after log-in. In a center portion in the personal top screen ARa, an area WA in which information indicative of a symptom in a natural sentence (symptom information) can be entered is provided. When the user enters a natural sentence indicative of the symptom in the area WA and clicks a search button SB1 with the mouse pointer MP, a search (natural sentence search) for a disease name and a caring method based on the symptom information described in the natural sentence can be started.

In step ST4, whether a search for the caring method is selected or not is determined by the server control unit 102. When the command button B3 in the nursing support screen G2 is clicked with the mouse pointer MP to select the search for the caring method, the routine advances to step ST7. On the other hand, when the search for the caring method is not selected, the routine advances to step ST5.

In step ST5, whether a caring method natural sentence search is instructed or not is determined by the server control unit 102. When the natural sentence search is not instructed, the routine returns to step ST4. When the natural sentence search is instructed, the routine advances to step ST6.

In step ST6, the symptom information described in the natural sentence in the personal top screen ARa is obtained by the symptom/disease name information receiving unit 102D, and the routine advances to step ST34 in FIG. 16.

In step ST7, a screen for selecting a disease name (hereinbelow, also called "disease name selection screen") is displayed by the server control unit 102 and the input/output control unit 12A. The display screen in the support information display area AR shifts from the personal top screen ARa to the disease name selection screen.

FIG. 21 is a diagram showing a disease name selection screen ARb displayed in the support information display area AR of the nursing support screen G2. It is assumed that data for displaying the disease name selection screen ARb is pre-stored in the storing unit 101.

In the disease name selection screen ARb, when the user knows the disease name, the mouse pointer MP is placed on a check button CB1 provided on the left side of indication "disease name is known" in an upper left part in the disease name selection screen ARb, and the left button of the mouse is clicked (left click). Further, by placing the mouse pointer MP on one of the disease names listed in the area A3 and clicking the left button, the disease name can be selected. On the other hand, when the user does not know the disease name, the mouse pointer MP is placed on a check button CB2 provided on the left side of indication "disease name is unknown" in an upper left part in the disease name selection screen ARb, and the left button of the mouse is clicked (left click). It can change the display screen in the support information display area AR to a screen for selecting a main symptom (hereinbelow, also called "main symptom selection screen").

In step ST8, whether the user knows the disease name or not is determined by the server control unit 102. When the mouse pointer MP is placed on the check box CB1 and the left button of the mouse is clicked, it is determined that the user knows the disease name, and the routine advances to step ST9. On the other hand, when the mouse pointer MP is placed on the check box CB2 and the left button of the mouse is clicked, it is determined that the user does not know the disease name, and the routine advances to step ST19.

In step ST9, whether the disease name is selected or not is determined by the server control unit 102. When the mouse pointer MP is placed on any of the disease names listed in an area A3 in the disease name selection screen ARb and, the left button of the mouse is clicked, it is determined that the disease name is selected, and the routine advances to step ST10. On the other hand, when the disease name is not selected, the routine returns to step ST8.

In step ST10, the disease name information indicative of the disease name is obtained by the symptom/disease name information receiving unit 102D. On the basis of the disease name information, one disease name element is recognized by the disease name recognizing unit 102E.

In step ST11, by referring to the disease-symptom DB 113, one or more symptom elements including a main symptom element corresponding to one disease name element recognized in step ST1 is recognized. For example, for the disease name element "appendicitis", the main symptom element "fever" and the detailed symptom element "the body temperature variation in one day is 1° C. or less" are recognized. An item of the one or more symptom elements recognized by the symptom element recognizing unit 102F is recognized as a reduction item, and reduction item specifying information that specifies the reduction item is transmitted to the input requesting unit 102B.

In step ST12, the reduction item is eliminated from the necessary items of the symptom element on the basis of the reduction item specifying information obtained from the symptom element recognizing unit 102F, thereby reducing the necessary items. At this time, information of requesting entry of the symptom element related to the necessary items is transmitted to the terminal 10 by input requesting unit 102B via the input/output control unit 102A or the like.

In step ST13, in response to a request from the input requesting unit 102B, a screen for entering a detailed symptom related to the main symptom element recognized in step ST11 (hereinbelow, also called "detailed symptom input screen") is visibly output in the display unit 13 by the terminal control unit 12 (particularly, the input/output control unit 12A).

FIG. 22 is a diagram illustrating a detailed symptom input screen ARc displayed in the support information display area AR in the nursing support screen G2.

FIG. 22 shows the case where the disease name element "appendicitis" is recognized in step ST10 and the main symptom element "fever" and the detailed symptom element "the body temperature variation in one day is 1° C. or less" are recognized in step ST11.

As shown in FIG. 22, a box BK1 displaying the already selected disease name is provided in a left upper part in the detailed symptom input screen ARc. Below the box BK1, personal information entry boxes PD are provided, for selecting, from a pull-down menu, personal information such as the relation of the patient with the user (for example, the user himself/herself, daughter, son, or the like), sex, age, and the like. Further, below the personal information entry boxes PD, detailed symptom entry boxes DS are provided, for selecting and entering detailed situations (detailed symptom) of the main symptom "fever" such as the degree of fever (such as a temperature range), a high-fever period (the number of days or the like), and the state of fever (such as fluctuation in fever) from a pull-down menu. Since the "state of fever" is unconditionally determined for "appendicitis", the element "the body temperature variation in a day is 1° C. or less" is written as a default in a pull-down menu PF. As described above, when the disease name is known, the time and work required to enter the main and detailed symptoms is lessened, so that the caring method can be known easily in short time.

In a left lower part of the detailed symptom input screen ARc, a plurality of candidates SF of diseases suffered in the past (past-disease candidate group) are listed. By placing the mouse pointer MP on a desired candidate of a past disease and clicking the left button of the mouse, the past disease can be filled in right-lower boxes CK in which a text can be entered. As the past-disease candidate group SF, diseases corresponding to the past-disease elements included in the disease-care-combination DB 112, for example, "diabetes", "glomerulonephritis", "hypertension", "asthma", "egg allergy", and the like are listed. The user can directly write past diseases in the boxes CK.

When a command button "next" NB1 is clicked with the mouse pointer MP in a state where the personal information is displayed in the personal information entry boxes PD, the detailed symptoms are properly displayed in the detailed symptom entry boxes DS, and the past diseases are filled in the boxes CK, the personal information displayed in the personal information entry boxes PD, the detailed symptoms displayed in the detailed symptom entry boxes DS, and the past diseases filled in the boxes CK are input as the personal information elements indicative of the personal information, the detailed symptom elements of the main symptom element, and the past-disease elements. On the other hand, when a command button "reset" RB1 is clicked with the mouse pointer MP, the personal information displayed in the personal information entry boxes PD, the detailed symptoms (detailed symptoms in the necessary items) displayed in the detailed symptom entry boxes DS, and the past diseases filled in the boxes CK are cleared.

In step ST14, whether the detailed symptom elements are entered or not is determined by the server control unit 102. The determination in step ST14 is repeated until a detailed symptom and the like are written in the detailed symptom input screen ARc and the command button "next" NB1 is clicked. When the command button "next" NB1 is clicked, it is determined that the detailed symptom elements are entered, and the routine advances to step ST15.

In step ST15, a detailed symptom element indicative of a detailed symptom written in the detailed symptom input screen ARc is obtained in combination with the main symptom element and the detailed symptom element recognized in step ST11 by the symptom/disease name information receiving unit 102D. By the personal information recognizing unit 102C, the past-disease element (that is, the personal information element) indicative of the past disease displayed or written in the detailed symptom input screen ARc is obtained.

In step ST16, a screen for additionally entering a main symptom element (hereinbelow, also called "additional symptom input screen") different from the main symptom element recognized in the step ST11 is displayed on the display unit 13 by the server control unit 102 and the terminal control unit 12.

Figure 23:
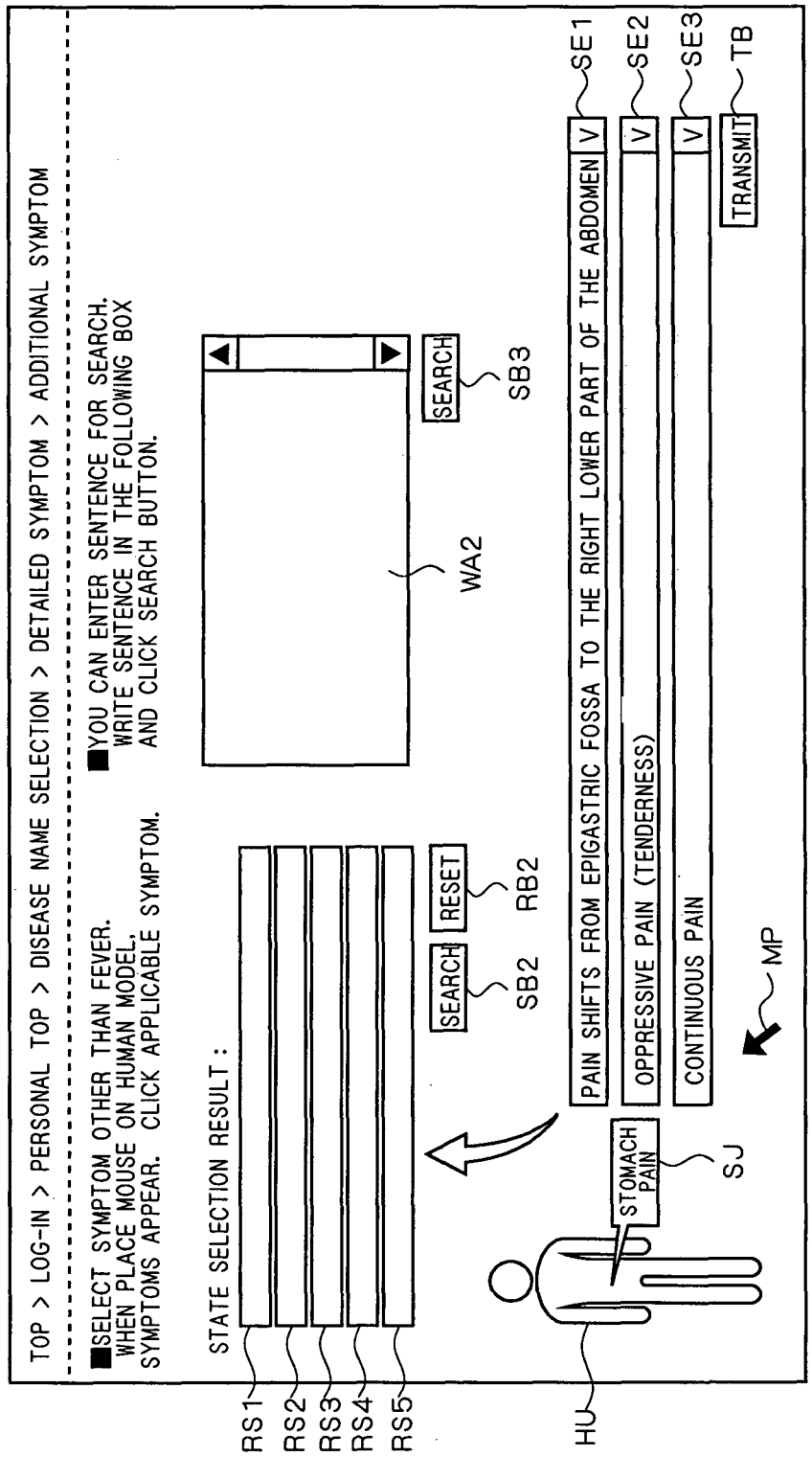
FIG. 23 is a diagram showing an additional symptom input screen of the nursing support system.

FIG. 23 is a diagram showing an additional symptom input screen ARd displayed in the support information display area AR in the nursing support screen G2.

In the additional symptom input screen ARd, when the user places the mouse pointer MP on a region (for example, an abdominal region) in which a main symptom different from the main symptom in the detailed symptom input screen ARc displayed in the step ST13 appears on a human model HU displayed in a left lower part and the right button of the mouse is clicked (right click), an additional main symptom name (for example, stomach pain) SJ occurring in the region appears. In this state, detailed symptoms of the additional main symptom (for example, "pain shifts from epigastric fossa to the right lower part of the abdomen", "oppressive pain (tenderness)", and "continuous pain") are properly selected with the mouse pointer MP in pull-down menus SE1 to SE3 provided on the right side of the additional main symptom name SJ, and a transmission button TB is clicked with the mouse pointer MP. As a state selection result, the detailed symptoms displayed in the additional main symptom name (accessory symptom) SJ and the menus SE1 to SE3 are transferred to boxes RS1 to RS5 provided in a part extending from the center to the left in the additional symptom input screen ARd.

When a search button SB2 is clicked with the mouse pointer MP, the combination of the main symptom element and the detailed symptom elements indicative of the additional main symptom and its detailed symptoms filled in the boxes RS1 to RS5 is added to the combination of the main symptom element and the detailed symptom elements recognized in step ST11 and the detailed symptom element obtained in step ST15, and start of a search for a caring method is instructed. When a reset button RB2 is clicked with the mouse pointer MP, the symptoms filled in the boxes RS1 to RS5 are deleted.

In the additional symptom input screen ARd, by filling additional symptom information in a natural sentence in a write area WA2 provided in a right part in the center portion and clicking a search button SB3 with the mouse pointer MP, the additional symptom information is added to the combination of the main symptom element and its detailed symptom elements recognized in step ST11 and the detailed symptom elements obtained in step ST15, and start of a search for a caring method is instructed.

In step ST17, whether a search instruction is given or not is determined by the server control unit 102. The determination in step ST17 is repeated until a search for a caring method is instructed by the click on the search buttons SB2 and SB3 in the additional symptom input screen ARd. When a search for a caring method is instructed, the routine advances to step ST18.

In step ST18, the symptom/disease name information receiving unit 102D obtains either the combination of the data elements (main symptom elements) indicative of main symptoms and the data elements (detailed symptom elements) indicative of one or more detailed symptoms of each of the main symptom elements filled in the boxes RS1 to RS5 in the additional symptom input screen ARd, or the additional symptom information written in the write area WA2 in the additional symptom input screen ARd. The routine advances to step ST31 in FIG. 16.

In step ST19, by the server control unit 102 and the terminal control unit 12, a screen for selecting a main symptom (hereinbelow, also called "main symptom selection screen") is displayed on the display unit 13 in response to the fact that the user does not know the disease name.

FIG. 24 is a diagram showing a main symptom selection screen ARe displayed in the support information display area AR in the nursing support screen G2. In the main symptom selection screen ARe, for example, a number of main symptoms are listed by classifications (constitutional symptom, head, nose, mouth, eyes, throat, abdomen, female genitalia, ears, chest, excretion, bones, limbs, and skin). By placing the mouse pointer MP on a desired main symptom in the number of main symptoms and clicking the left button of the mouse, a data element (main symptom element) of the desired main symptom can be selected.

In step ST20, whether a main symptom element is selected or not is determined by the server control unit 102 and the terminal control unit 12. Until a main symptom element is selected in the main symptom selection screen ARe, the determination in step ST20 is repeated. After a main symptom element is selected, the routine advances to step ST21.

In step ST21, the symptom/disease name information receiving unit 102D obtains the main symptom element selected on the main symptom selection screen ARe.

In step ST22, by the server control unit 102 and the terminal control unit 12, a screen for entering a detailed symptom of the main symptom element obtained in step ST21 (detailed symptom input screen) is displayed on the display unit 13.

FIG. 25 is a diagram showing a detailed symptom input screen ARf displayed in the support information display area AR in the nursing support screen G2. FIG. 25 shows the case where the main symptom element "fever" is obtained in step ST21. The detailed symptom input screen ARf has a configuration similar to that of the detailed symptom input screen ARc shown in FIG. 22. Therefore, the same reference numerals are designated to similar parts and their description will not be repeated. In FIG. 25, however, since a disease name is not selected, no disease name is displayed in the box BK1, and no element is written as a default in the pull-down menu PF. In the menu PF, a desired element can be selected.

In step ST23, like in step ST14, whether the detailed symptom elements are entered or not is determined by the server control unit 102. The determination in step ST23 is repeated until a detailed symptom is filled in the detailed symptom input screen ARf and the command button "next" NB1 is clicked. When a detailed symptom is written in the detailed symptom input screen ARf and the command button "next" NB1 is clicked, it is determined that the detailed symptom element is entered, and the routine advances to step ST24.

In step ST24, like in step ST15, a detailed symptom element indicative of a detailed symptom written in the detailed symptom input screen ARf is obtained in combination with the main symptom element recognized in step ST21 by the symptom/disease name information receiving unit 102D. By the personal information recognizing unit 102C, the past-disease element (that is, the personal information element) indicative of the past disease displayed or written in the detailed symptom input screen ARf is obtained.

In step ST25, like in step ST16, a screen for additionally entering a main symptom element (hereinbelow, also called "additional symptom input screen") different from the main symptom element obtained in the step ST21 is displayed on the display unit 13 by the server control unit 102 and the terminal control unit 12. The additional symptom input screen ARd similar to that of FIG. 23 is displayed.

In step ST26, whether a search instruction is given or not is determined by the server control unit 102. The determination in step ST26 is repeated until a search for a caring method is instructed by the click on the search buttons SB2 and SB3 in the additional symptom input screen ARd. When a search for a caring method is instructed, the routine advances to step ST27.

In step ST27, the symptom/disease name information receiving unit 102D obtains either the combination of the data elements (main symptom elements) indicative of main symptoms and the data elements (detailed symptom elements) indicative of one or more detailed symptoms of each of the main symptom elements filled in the boxes RS1 to RS5 in the additional symptom input screen ARd, or the additional symptom information written in the write area WA2 in the additional symptom input screen ARd. The routine advances to step ST33 in FIG. 16.

In step ST31 in FIG. 16, the symptom element recognizing unit 102F recognizes all symptom elements on the basis of one or more symptom elements including a main symptom element corresponding to the one disease name element recognized in step ST11, a detailed symptom element obtained in combination with the main symptom element in step ST15, and either a combination of the main symptom element and one or more detailed symptom element obtained in step ST18, or the additional symptom information. In this example, all symptom elements are recognized in a form that one or more detailed symptom elements of each of the main symptom elements is combined with the main symptom element.

In step ST31, in the case where additional symptom information is entered in a natural sentence on the additional symptom input screen ARd, by a language analysis using data for morphological analysis, data for dependency structure analysis, keyword data, dictionary data, and the like, one or more symptom elements including at least one main symptom element are recognized. For example, in the case where a natural sentence such as "I have a pain in stomach" is entered, a keyword of "have a stomach pain" is extracted. By converting "have a stomach pain" to a representative word "stomachache" using the dictionary data, one main symptom element "stomachache" is recognized. A detailed symptom element (such as "epigastric fossa") of the main symptom element "stomachache" is recognized by performing the morphological analysis and the dependency structure analysis on a modification relation of words in a natural sentence.

In step ST32, the disease name detecting unit 102G extracts one or more pieces of symptom-disease-combination information of one or more symptom elements recognized in step ST31 and one disease name element recognized in step ST10 from the disease-symptom-combination DB 111. The one or more pieces of symptom-disease-combination information extracted by the disease name detecting unit 102G are transmitted to the disease name detection route information generating unit 102H.

In step ST33, like in step ST31, the symptom element recognizing unit 102F recognizes a symptom element on the basis of the main symptom element recognized in step ST21, the detailed symptom element obtained in combination with the main symptom element in step ST24, and either each of combinations of the main symptom element and one or more detailed symptom elements obtained in step ST27, or the additional symptom information. All symptom elements are recognized in a form that one or more detailed symptom elements of each of the main symptom elements are combined with each of the main symptom elements.

In step ST34, the symptom element recognizing unit 102F recognizes a symptom element by analyzing the symptom information (symptom information written in a natural sentence) obtained in step ST6. In this case, one or more symptom elements are recognized by a language analysis using data for morphological analysis, data for dependency structure analysis, keyword data, dictionary data, and the like. For example, in the case where natural sentences such as "I have a fever and a stomach pain. What is the matter with me?" are entered, two keywords "have a fever" and "a stomach pain" are extracted by using the keyword data. With the dictionary data, "have a fever" is converted to a representative word "fever" and "a stomach pain" is converted to a representative word "stomachache". In such a manner, two main symptom elements "fever" and "stomachache" are recognized. One or more detailed symptom elements (such as "epigastric fossa") of each main symptom element (for example, "stomachache") are recognized, for example, by performing the morphological analysis and the dependency structure analysis on the modification relation of words in the natural sentences. In this case, all symptom elements are recognized in a form that one or more detailed symptom elements of each main symptom element are combined with the main symptom element.

In step ST35, the disease name detecting unit 102G detects a disease name (disease name element) according to a symptom by referring to the disease-symptom-combination DB 111 on the basis of the all symptom elements (information of the combination between a main symptom element and one or more detailed symptom elements) recognized in step ST33 or ST34. In this case, by extracting one or more pieces of symptom-disease-combination information including one or more symptom elements recognized in step ST33 or ST34 from the disease-symptom-combination DB 111, a disease name element included in the one or more symptom-disease-combination information is detected.

In step ST36, the disease name detecting unit 102G determines whether one disease name element is detected or not in step ST35. In the case where a plurality of disease name elements are detected, the routine advances to step ST37. On the other hand, when one disease name element is detected, the routine advances to step ST45. In this case, one or more pieces of symptom-disease-combination information extracted by the disease name detecting unit 102G in step ST35 is transmitted to the disease name detection route information generating unit 102H.

In step ST37, the disease name detecting unit 102G determines whether the main symptom element included in the all symptom elements recognized in step ST33 or ST34 is only "fever" or not. When the main symptom element is only "fever", to request for another input of a main symptom element, the routine returns to step ST25 in FIG. 15. On the other hand, when the main symptom element is not only "fever", the routine advances to step ST38.

In step ST38, by the server control unit 102 and the input/output control unit 12A, a screen displaying questions for narrowing down a plurality of disease name elements to one disease name element (hereinbelow, also called "narrow-down question screen") is visibly output in the display unit 13. By the disease name detecting unit 102G, the narrow-down question information for narrowing down a plurality of disease name elements to one disease name element is transmitted to the input requesting unit 102B in accordance with the plurality of combinations of the disease name elements detected. By the input requesting unit 102B, the narrow-down question information is transmitted to the terminals 10 to 40 via the input/output control unit 102A or the like. By the input/output control unit 12A in the terminal control unit 12, the narrow-down question information is visibly output in the display unit 13.

FIG. 26 is a diagram showing a narrow-down question screen ARg displayed in the support information display area AR of the nursing support screen G2. The narrow-down question screen ARg shown in FIG. 26 is an example of the screen displayed in the case where two disease name elements "cold syndrome" and "influenza" are detected in step ST35. It is assumed that data for displaying the narrow-down question screen ARg is pre-stored in the storing unit 101.

In the narrow-down question screen ARg, sentences clearly specifying that a plurality of disease names are detected as a disease name search result and sentences asking the user to answer questions for narrowing the disease names to one disease name are described in an upper part of the screen. From the center part of the screen toward the bottom, four questions are shown in order from top; "Did you receive a vaccination against influenza?", "If yes, when did you receive it ?", "Did you catch influenza in the past six months?", and "Is your family member or close person having influenza?" On the right side of each of the questions, a pull-down menu for selecting an answer to the question is provided. By operating the operation unit 14, the user selects and displays an answer to the question from the pull-down menu with the mouse pointer MP. When a search button SB4 is clicked with the mouse pointer MP, information indicative of an answer to the narrow-down question information (narrow-down answer information) is transmitted to the disease name detecting unit 102G.

In step ST39, whether a search instruction is given or not is determined by the server control unit 102. The determination in step ST39 is repeated until the search button SB4 is clicked in the narrow-down question screen ARg and the disease name detecting unit 102G receives the narrow-down answer information. When the disease name detecting unit 102G receives the narrow-down answer information, it is determined that a search instruction is given, and the routine advances to step ST40.

In step ST40, the disease name detecting unit 102G detects a disease name element corresponding to the narrow-down answer information from the plurality of disease name elements detected in step ST35.

In step ST41, the disease name detecting unit 102G determines whether the disease name elements were narrowed to one disease name element or not by the detecting process in step ST40. When the disease name elements were narrowed to one disease name element, the routine advances to step ST45. When the disease name elements are not narrowed to one disease name element, the routine advances to step ST42. By the disease name detecting unit 102G, the plurality of disease name elements detected in step ST40 are transmitted to the terminal 10. In the case where the routine advances to step ST45, only one or more pieces of symptom-disease-combination information corresponding to one disease name element detected in step ST40 out of the one or more symptom-disease-combination information pieces extracted in step ST35 are transmitted to the disease name detection route information generating unit 102H.

In step ST42, a screen for selecting one disease name from a plurality of disease names (hereinbelow, also called "disease name selection screen") on the basis of the plurality of disease name elements transmitted in step ST41 is visibly output on the display unit 13 by the input/output control unit 12A.

Figure 27:
FIG. 27 is a diagram showing a disease name selection screen of the nursing support system.

FIG. 27 is a diagram showing a disease name selection screen ARh displayed in the support information display area AR of the nursing support screen G2. As the disease name selection screen ARh shown in FIG. 27, an example of a screen displayed when the two disease name elements "cold syndrome" and "influenza" are detected in step ST40 is shown. It is assumed that data for displaying the disease name selection screen ARh is pre-stored in the storing unit 101.

In the disease name selection screen ARh shown in FIG. 27, a sentence indicating that a plurality of disease names cannot be narrowed down to one disease name as a result of the disease name search and a sentence requesting the user to select one of the disease names are written in an upper part of the screen. The plurality of disease names (in this case, "cold" and "influenza") are displayed from the center portion of the screen toward the bottom. A radio button is provided on the left side of each of the disease names. The user checks a radio button with the mouse pointer MP by operating the operation unit 14, thereby exclusively selecting one disease name. When a search button SB5 is clicked with the mouse pointer MP, a data element indicative of the disease name (disease name element) exclusively selected is transmitted to the disease name detecting unit 102G.

In step ST43, the disease name detecting unit 102G determines whether one disease name element is selected in the disease name selection screen ARh or not. The determination in step ST43 is repeated until one disease name element is received by the disease name detecting unit 102G. After one disease name element is received, the routine advances to step ST44.

In step ST44, the disease name detecting unit 102G recognizes one disease name element selected on the disease name selection screen ARh. Only one or more symptom-disease-combination information corresponding to one disease name element recognized in step ST44 out of the one or more symptom-disease-combination information extracted in step ST35 is transmitted to the disease name detection route information generating unit 102H.

In step ST45, the disease name detection route information generating unit 102H generates information indicative of a route of detecting one disease name element (disease name detection route information) on the basis of the one or more pieces of symptom-disease-combination information obtained in any of steps ST32, ST36, ST41, and ST44. The disease name detection route information is transmitted to the terminal 10 via the input/output control unit 102A and the like.

In the case where one or more pieces of symptom-disease-combination information are constructed by a plurality of pieces of symptom-disease-combination information, since the plurality of pieces of symptom-disease-combination information have a common disease name element, the disease name detection route information has a form in which the one or more pieces of symptom-disease-combination information are connected so as to converge to a single disease name element. For example, the disease name detection route information is described in the RDF (Resource Description Framework) or the like.

Figure 28:
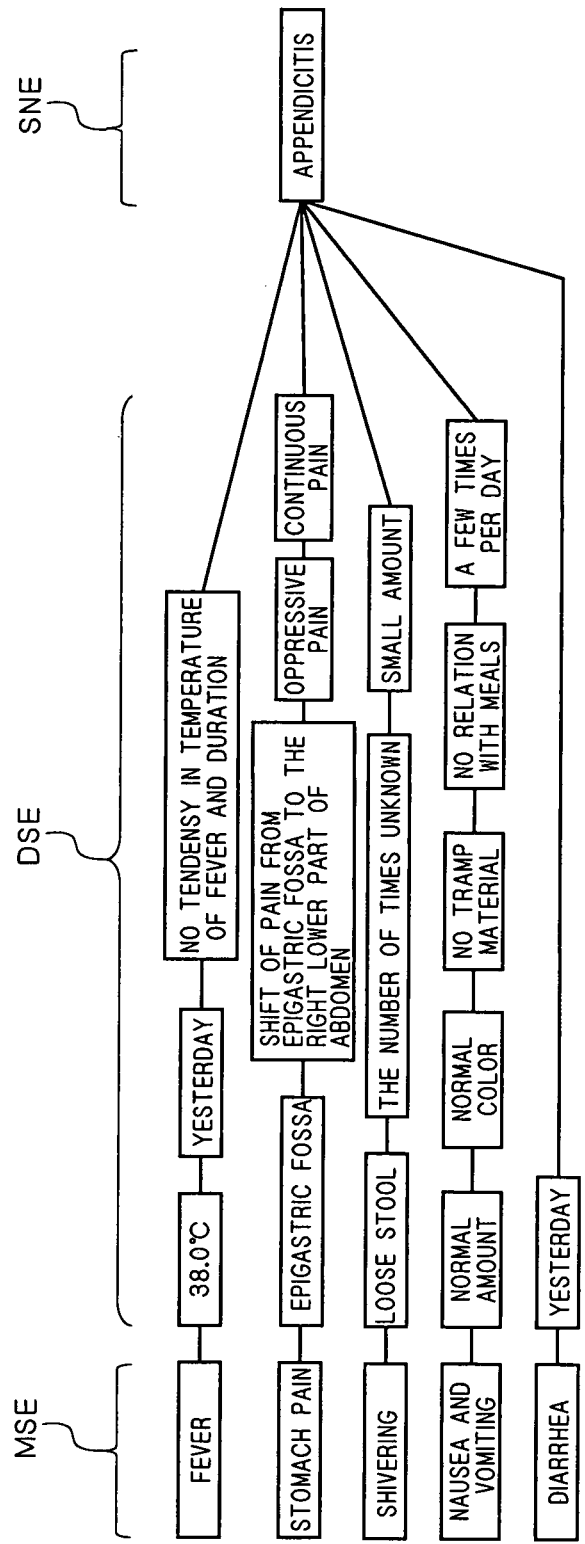
FIG. 28 is a diagram showing disease name detection route information.

FIG. 28 is a diagram showing the disease name detection route information. A line connecting elements indicates association (that is, combination) of the elements.

In FIG. 28, the symptom element recognizing unit 102F recognizes a combination of main symptom element "fever"—detailed symptom element "38.0° C."—detailed symptom element "yesterday"—detailed symptom element "no tendency in temperature and duration", a combination of main symptom element "stomachache"—detailed symptom element "epigastric fossa"—detailed symptom element "shift of pain from epigastric fossa to the right lower part of abdomen"—detailed symptom element "oppressive pain"—detailed symptom element "continuous pain", a combination of main symptom element "shivering"—detailed symptom element "loose stool"—detailed symptom element "the number of times unknown"—detailed symptom element "small amount", a combination of main symptom element "nausea and vomiting"—detailed symptom element "normal amount"—detailed symptom element "normal color"—detailed symptom element "no tramp material"—detailed symptom element "no relation with meals"—detailed symptom element "a few times per day", and a combination of main symptom element "diarrhea"—detailed symptom element "yesterday". Disease name detection route information generated in the case where one disease name element "appendicitis" is detected by the disease name detecting unit 102G is shown in FIG. 28.

As shown in FIG. 28, the disease name detection route information has a form in which a main symptom element MSE, a detailed symptom element DSE, and a disease name element SNE are associated. FIG. 28 shows the routes in which the disease name detecting unit 102G extracts five combinations of symptom-disease-combination information from the disease-symptom-combination DB 111, and the disease name element "appendicitis" common to the five combinations of symptom-disease-combination information is detected by the disease name detecting unit 102G. That is, the disease name detection route information shows the process of detecting the disease name element SNE of "appendicitis" on the basis of the combinations of the main symptom elements MSE and one or more detailed symptom elements DSE.

In step ST46, the care detecting unit 102I detects a plurality of care elements corresponding to one disease name element recognized or detected in any of steps ST10, ST35, ST40, and ST44 from the disease-care-combination DB 112.

In the case where the routine advances via step ST32, a plurality of pieces of symptom-disease-personal information-care-combination information are extracted from the disease-care-combination DB 112, thereby detecting a care element. The plurality of pieces of symptom-disease-personal information-care-combination information include one disease name element obtained in step ST10, a combination of one or more symptom elements recognized in step ST31, and one of the personal information elements recognized in steps ST2 and ST15 (information of a combination of one or more symptom elements, one disease name element, one personal information element, one (or two) care element(s), and one detailed care element).

In the case where routine advances via steps ST33 and ST36, a care element is detected by extracting a plurality of pieces of symptom-disease-personal information-care-combination information from the disease-care-combination DB 112. The plurality of pieces of symptom-disease-personal information-care-combination information include one disease name element obtained in step ST35, a combination of one or more symptom elements recognized in step ST33, and one of the personal information elements recognized in step ST2 and ST24 (information of a combination of one or more symptom elements, one disease name element, one personal information element, one (or two) care element(s), and one detailed care element). In the case where the routine advances via step ST34, the combination including one or more symptom elements recognized in step ST34 is used. In the case where the routine advances from step ST41 to step ST45, one disease name element detected in step ST40 is used. In the case where the routine advances from step ST44 to step ST45, one disease name element recognized in step ST44 is used.

A plurality of pieces of symptom-disease-personal information-care-combination information extracted in step ST46 are transmitted to the detailed information detecting unit 102K and the disease care information generating unit 102J.

In step ST47, the disease care information generating unit 102J generates disease care information in which a disease name element and a care element are combined on the basis of the plurality of pieces of symptom-disease-personal information-care-combination information extracted in step ST46. The disease care information is transmitted to the terminal 10 via the input/output control unit 102A or the like.

A process of arranging the elements included in the plurality of pieces of symptom-disease-personal information-care-combination information by item, re-associating the elements with each other, and describing the re-associated elements in the RDF is performed on all of the pieces of symptom-disease-personal information-care-combination information. Since the plurality of pieces of symptom-disease-personal information-care-combination information have a common disease name element, the disease care information has a form in which the one disease name element is used as a start point and the other elements included in the plurality of pieces of symptom-disease-personal information-care-combination information are arranged by item and re-associated with each other. In other words, the disease care information is formed in such a manner that a plurality of elements (in this case, words) are listed item by item, and are associated with each other so as to form a network (hereinbelow, also called "network information"). The association among the elements in the network information is limited to the combinations of elements in the symptom-disease-personal information-care-combination information.

Figure 29:
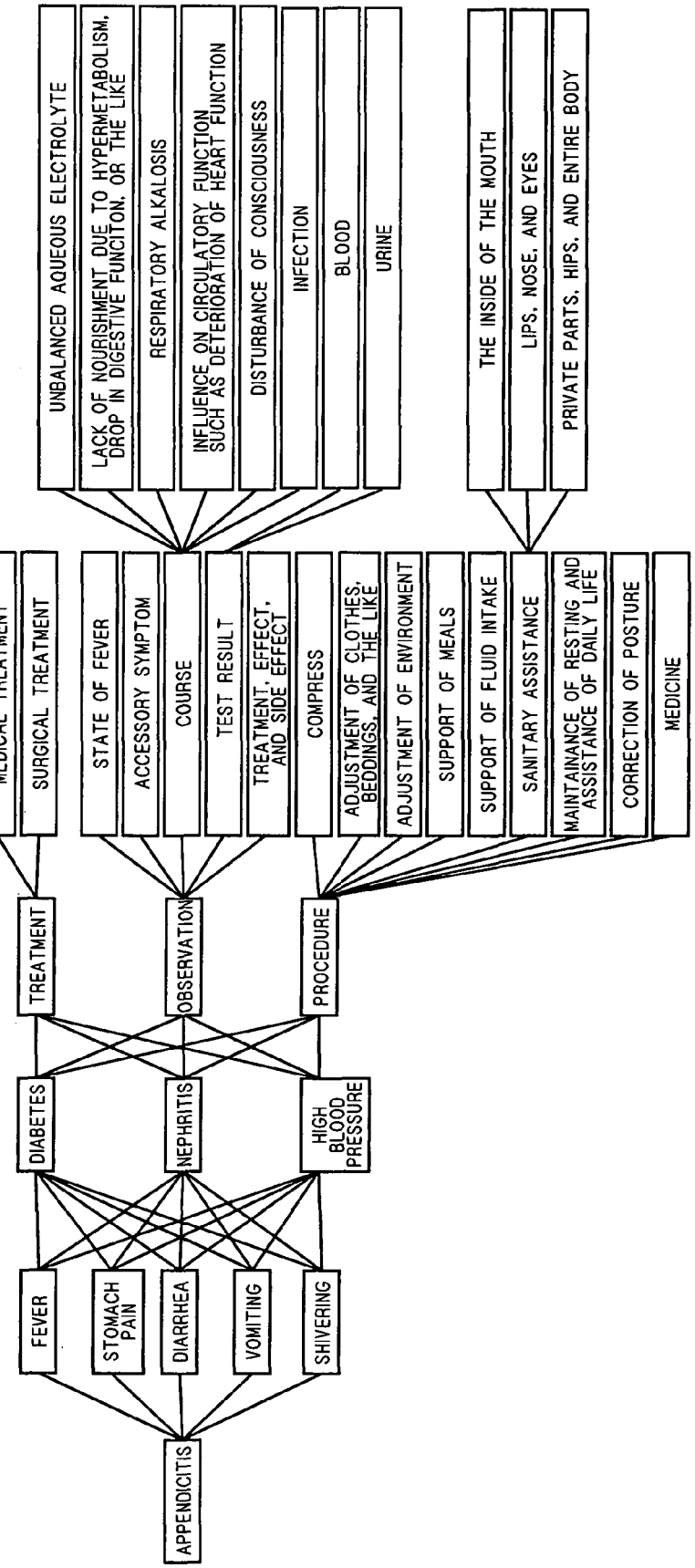
FIG. 29 is a diagram showing disease care information.

FIG. 29 is a diagram showing the disease care information. A line connecting elements indicates association of the elements (that is, combination in the symptom-disease-personal information-care-combination information). In FIG. 29, the disease name element SNE of "appendicitis" belonging to the item of a disease name element, a plurality of symptom elements HNE of "fever", "stomach", "diarrhea", "vomiting", and "shivering" belonging to the item of symptom elements, a plurality of past-disease elements PDE of "diabetes", "nephritis", and "high blood pressure" belonging to the item of the past-disease elements (generally, personal information element), care classification elements MRE of "treatment", "observation", and "procedure" belonging to the care classification item, care elements RE1 of "medical treatment", "surgical treatment", ..., "correction of posture", and "medicine" belonging to the care element item, and care elements RE2 of "unbalanced aqueous electrolyte", ..., and "private parts, hips, and entire body" belonging to the care element item are associated with each other.

The disease care information is transmitted/received in a state where the symptom-disease-personal information-care-combination information is attached for the reason that the original symptom-disease-personal information-care-combination information cannot be known only from the network information.

In step ST48, a screen in which the disease care information generated in step ST47 is visibly output (hereinbelow, also called "disease care screen") is displayed on the display unit 13 by the input/output control unit 12A.

Figure 30:
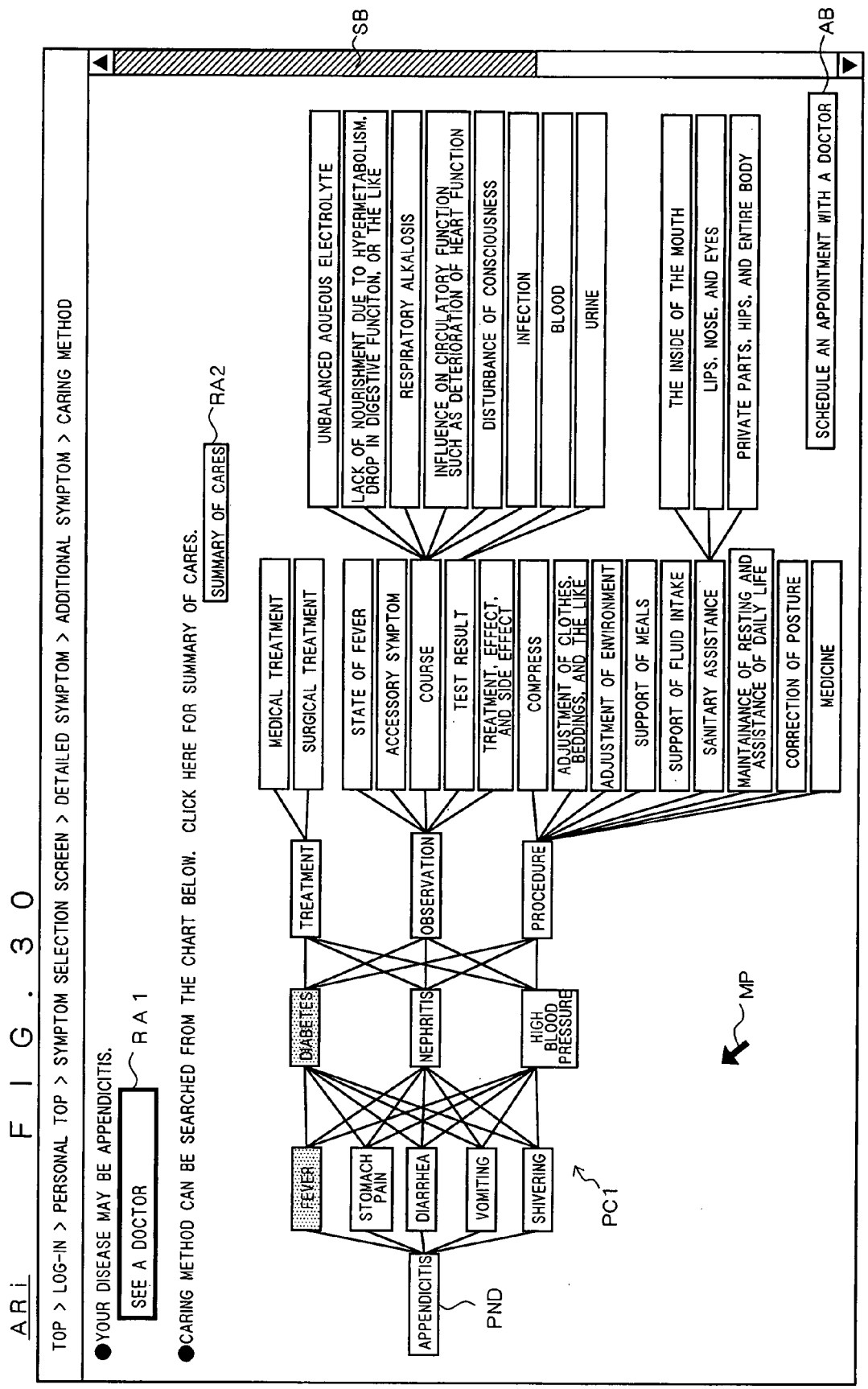
FIG. 30 is a diagram showing a disease care screen.

FIG. 30 is a diagram showing a disease care screen ARi displayed in the support information display area AR of the nursing support screen G2. FIG. 30 shows an example of visibly outputting the disease care information illustrated in FIG. 29.

As shown in FIG. 30, a chart PC1 in which the disease care information is visibly output is presented in a portion extending downward from the center of the disease care screen ARi. With reference to a number of care elements visibly presented in the chart PC1 of the disease care information, the user can easily recognize caring methods for the detected disease name.

In a left upper portion of the disease care screen ARi, an initial care element "see a doctor" which is an initial caring method RA1 to the disease (in this case, appendicitis) is displayed. A button RA2 for requesting display of summary of a general caring method to the disease (caring method summary request button) is provided in a right upper portion. The user can make the summary of the general caring method to the disease displayed on the display unit 13 by clicking the caring method summary request button RA2 with the mouse pointer MP.

Such a mode can be realized by storing the initial caring method RA1 and the information of the summary of the general caring method so as to be associated properly with disease name elements and the like in the medical DB 110 (for example, the disease-care-combination DB 112). Concretely, in the disease-care-combination DB 112, a plurality of care elements indicative of cares at a plurality of levels (the initial caring method, the summary of the general caring method, and detailed caring methods such as "compress") are combined with the disease name elements. A plurality of detailed care elements corresponding to the plurality of care elements are included in the detailed data group 115. Further, in a right lower part of the disease care screen ARi shown in FIG. 30, a button AB requesting a connection to a site for having an appointment with a doctor in a hospital of the membership of the system is provided.

In step ST49, whether an instruction of switching the screen display is given or not is determined by the terminal control unit 12. When the instruction of switching the screen display is given, the routine advances to step ST50. When the switching instruction is not given, the routine advances to step ST51 in FIG. 17. For example, when the disease care screen ARi is displayed on the display unit 13, by placing the mouse pointer MP on a disease name element PND and clicking the left button of the mouse on the disease care screen ARi, display of a screen ARj on which the disease name detection route information is visibly shown (hereinbelow, also called "disease name detection route screen") which will be described later is requested, and it is determined that the screen display switching instruction is given. In the case where the disease name detection route screen ARj is displayed on the display unit 13, by placing the mouse pointer MP on the disease name element PND and clicking the left button of the mouse on the disease name detection route screen ARj, display of the disease care screen ARi is requested, and it is determined that the screen display switching instruction is given.

In step ST50, by the input/output control unit 12A in the terminal control unit 12, the screen displayed on the display unit 13 is switched from the disease care screen ARi to the disease name detection route screen ARj or from, the disease name detection route screen ARj to the disease care screen ARi, and the routine advances to step ST51 in FIG. 17. In this case, by the input/output control unit 12A in the terminal control unit 12, the disease name detection route screen ARj is displayed on the basis of the disease name detection route information generated in step ST45, and the disease care screen ARi is displayed on the basis of the disease care information generated in step ST47.

Figure 31:
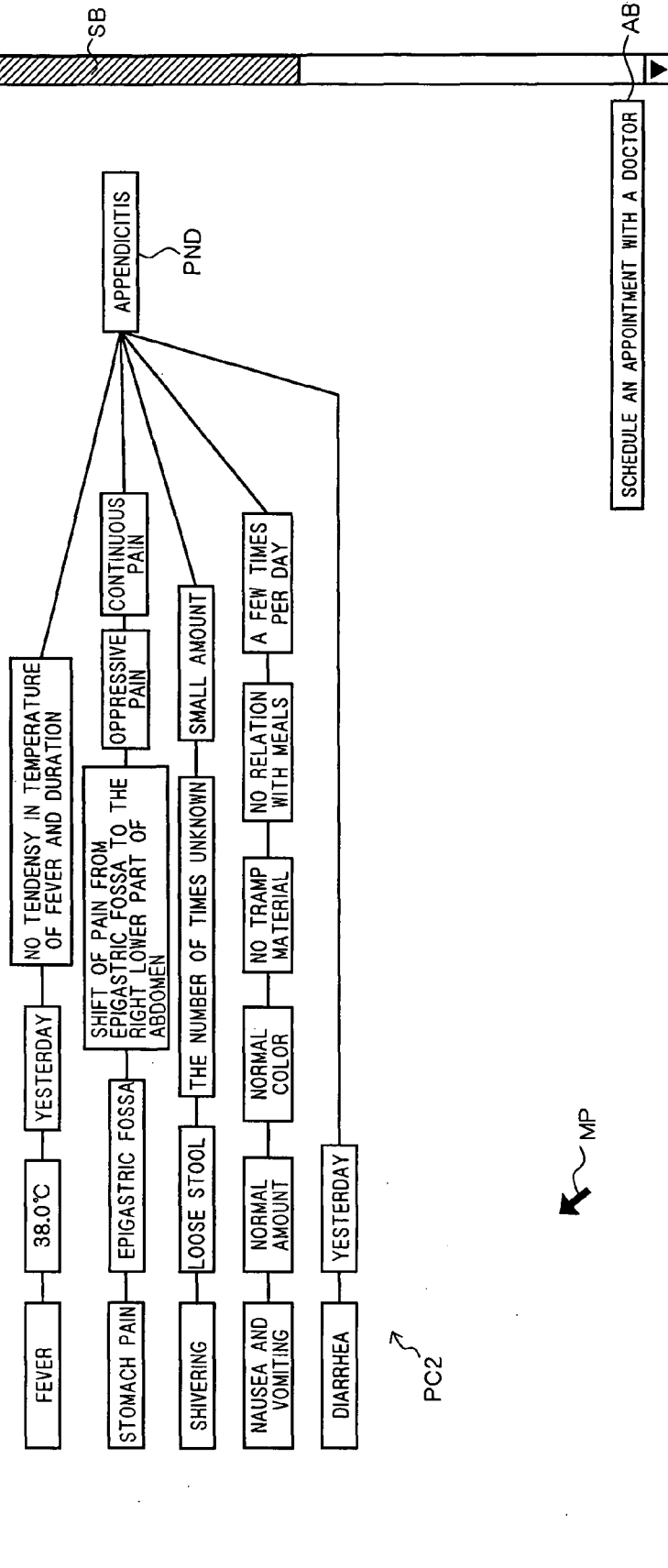
FIG. 31 is a diagram showing a disease name detection route screen.

FIG. 31 is a diagram showing the disease name detection route screen ARj displayed in the support information display area AR in the nursing support screen G2.

As shown in FIG. 31, in the disease name detection route screen ARj, the chart PC1 of the disease care information in the disease care screen ARi shown in FIG. 30 is replaced with a chart PC2 in which the disease name detection route information is visibly output. In FIG. 31, the chart PC2 of the disease name detection route information which is shown in FIG. 28 is visibly output. The user can easily know how the disease name is detected (the route) with reference to the relation between the symptom elements and the disease name elements visibly presented in the chart PC2 of the disease name detection route information, and can know erroneous entry of the symptom element. That is, the user can confirm whether the detected disease name is proper or not, so that the precision of detection of a disease name can be improved.

In the embodiment, first, the disease care screen ARi is preferentially visibly presented in the display unit 13 in step ST48. According to the screen display switching instruction, in step ST50, the disease name detection route screen ARj is visibly presented in the display unit 13. In other words, in response to detection of the plurality of care elements by the care detecting unit 102I, first, the disease care screen ARi is preferentially presented and, then, the disease name detection route screen ARj is presented. When a symptom is entered in such a manner, a combination of a disease name and a plurality of cares according to the symptom is visibly presented. Consequently, the user can know the care according to the situation promptly and easily. Since the combination of a disease name according to the symptom and a plurality of cares and a route of detecting the disease name from the symptom are presented in order with respect to time, the amount of information presented at once becomes smaller, and desired information can be viewed more easily.

In step ST51, the detailed information detecting unit 102K determines whether one care element included in the chart PC1 of the disease care information is designated or not. When the mouse pointer MP is placed on one care element included in the chart PC1 of the disease care information (FIG. 30 and the like) and the left button of the mouse is clicked, information designating the care element (care element designating information) is input to the detailed information detecting unit 102K via the input/output control unit 102A and the like. It is determined that the care element is designated, and the routine advances to step ST52. On the other hand, when the care element is not designated, the routine advances to step ST53.

In step ST52, by the input/output control unit 12A of the terminal 10, the detailed care element corresponding to information of designating one care element (care element designating information) obtained in step ST51 is visibly displayed in the display unit 13. The detailed information detecting unit 102K detects the detailed care element corresponding to the care element designating information from the detailed data group 115 on the basis of the care element designating information obtained in step ST51. The detected detailed care element is transferred to the terminal 10 via the input/output control unit 102A and the like. The detailed care element is visibly output in the display unit 13 by the input/output control unit 12A.

Figure 32:
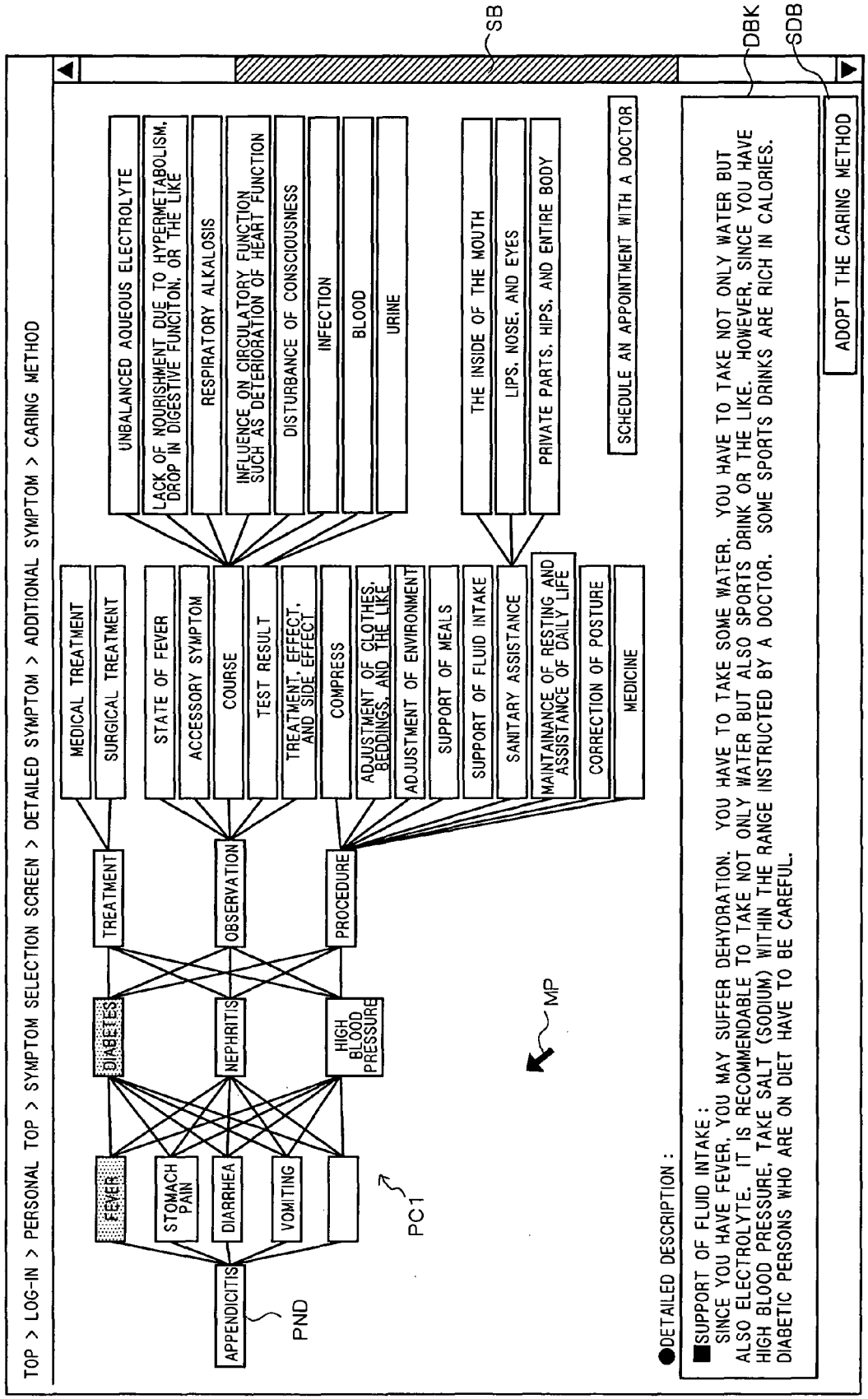
FIG. 32 is a diagram showing a state in which detailed description of a caring method is presented.

FIG. 32 is a diagram showing a state where the care element is designated and detailed care elements of the care element are visibly output in the disease care screen ARi.

As shown in FIG. 32, the disease care screen ARi can be scrolled in the vertical direction by a scroll bar SB provided at the left end. In a detailed description box DBK provided below the chart PC1 of the disease care information, detailed elements of a designated element are visibly output. In FIG. 32, by placing the mouse pointer MP on the care element "support of fluid intake" in the chart PC1 of the disease care information and clicking the left button of the mouse, detailed care elements of the care element "support of fluid intake" are visibly output in the detailed description box DBK.

In the disease care screen ARi, the user places the mouse pointer MP on a desired symptom element (for example, "fever") and a desired past-disease element (for example, "diabetes") included in the chart PC1 of the disease care information and clicks the left button of the mouse, thereby designating the elements. The designated elements are displayed in a mode (hatched in FIG. 32) which can be distinguished from the other elements. The detailed information detecting unit 102K refers to one or more pieces of symptom-disease-personal information-care-combination information entered from the care detecting unit 102I, and the detailed care elements visibly output in the detailed description box DBK correspond to the designated symptom element and past-disease element. For example, when the symptom element "fever" and the past-disease element "diabetes" are selected, the detailed care elements of the symptom-disease-personal information-care-combination information including the two elements "fever" and "diabetes" out of the symptom-disease-personal information-care-combination information obtained from the care detecting unit 102I are visibly output.

Therefore, the user can know detailed information of a care adapted to each patient, which varies depending on a symptom, personal information (in this case, a past disease) and the like even in the same disease. In the case where the personal information includes information such as drugs (for example, medicine which is currently taken), the allergy, and the like, the detailed information of the caring method to which the personal information is added is presented. Consequently, the user can know the care adapted to each patient.

In the disease care screen ARi, caring methods at a plurality of levels such as an initial caring method, summary of a general caring method, and a detailed caring method are prepared, and information of the caring method according to the level of the user can be presented. In the case where the user wishes to know prognosis or the like, an accessory symptom can be selected, or complication of the disease or the like can be selected.

Figure 33:
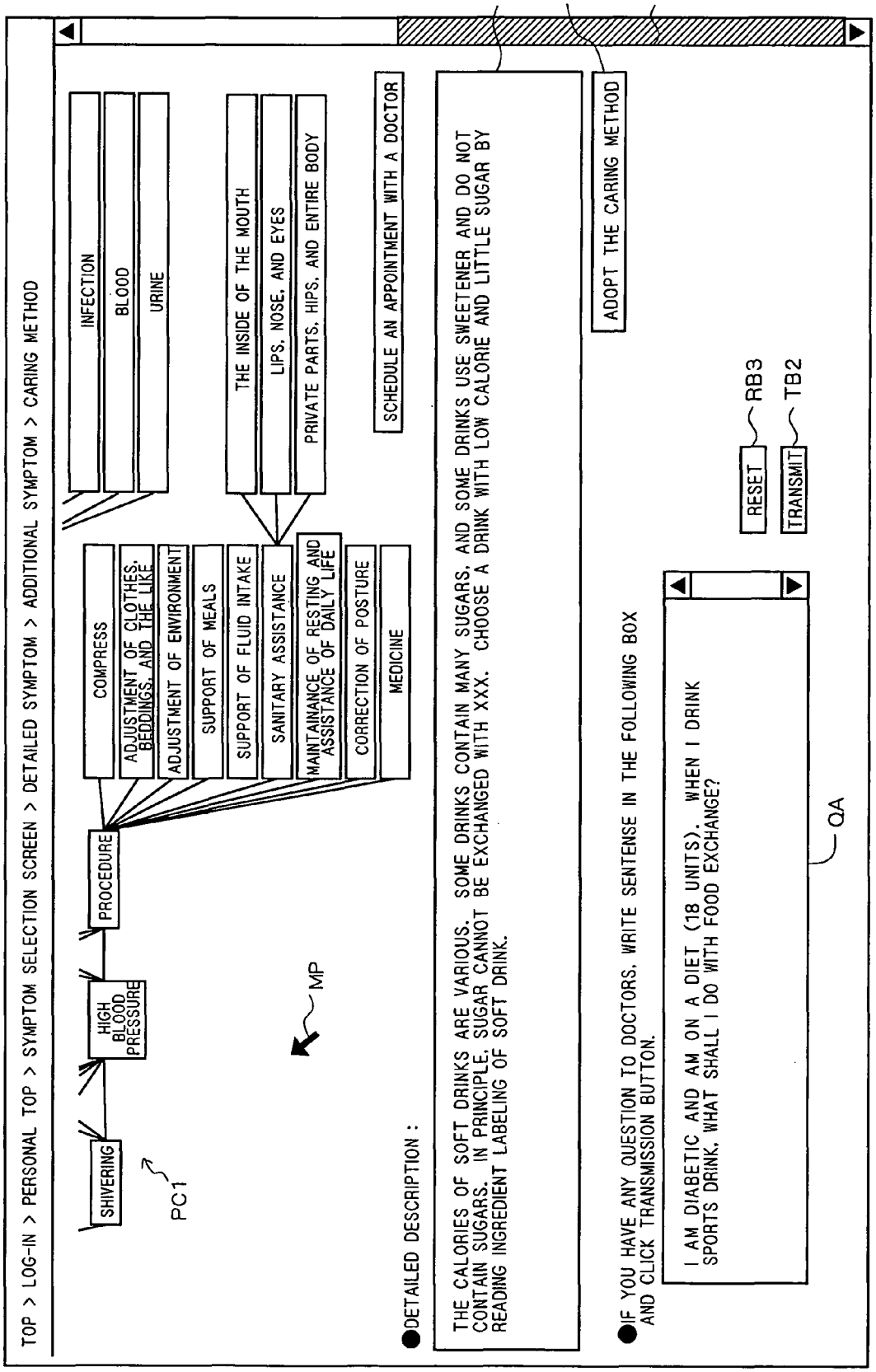
FIG. 33 is a diagram showing a state of entering a question.

Further, when the disease care screen ARi is scrolled downward by the scroll bar SB as shown in FIG. 33, a question box QA appears below the detailed description box DBK, that is, at the bottom of the disease care screen ARi. When a question in a natural sentence (question information) is entered in the question box QA and a transmission button TB2 is clicked with the mouse pointer MP, the user can make a question. Examples of questions are a question on data which is in the chart PC1 of the disease care information, a question on data which is not in the chart PC1, and a question on the other things. When a reset button RB3 is clicked with the mouse pointer MP, the information in the question box QA is erased.

In step ST53, whether the question information is entered or not is determined by the terminal control unit 12 and the server control unit 102. In response to an input operation on the terminal 10 of the user, a question sentence is written in the question box QA in the disease care screen ARi, and the transmission button TB is clicked. It is consequently determined that the question information is entered, and the routine advances to step ST54. On the other hand, when question information is not entered, the routine advances to step ST60.

In step ST54, the question information receiving unit 102M obtains the question information from the terminal control unit 12 via the input/output control unit 102A or the like.

In step ST55, the question information analyzing unit 102N performs a language analysis (a language analysis using data for morphological analysis, data for dependency structure analysis, keyword data, and dictionary data) on the question information received by the question information receiving unit 102M in step ST54, thereby recognizing a question element indicative of a question including at least one care element. The question element recognized here may be an element of any form such as a long form, a paragraph, or a term, or combination of one or more elements of any form such as a long form, a paragraph, and a term. An example of the question element is a combination of one care element and one or more symptom elements.

In step ST56, the answer retrieving unit 102O searches the medical DB 110 (concretely, the disease-care-combination DB 112) for a detailed care element (that is, answer information) corresponding to the question element recognized in step ST55 to detect it. For example, when the question element is a combination of one care element, one or more symptom elements, and one or more personal information elements, one or more pieces of the symptom-disease-personal information-care-combination information including the combination of the one care element, the one or more symptom elements, and the one or more personal information elements are detected from the disease-care-combination DB 112, thereby detecting a detailed care element (answer information) included in the one or more pieces of the symptom-disease-personal information-care-combination information.

In step ST57, whether the answer information corresponding to the question element recognized in step ST55 exists in the medical DB 110 (concretely, the disease-care-combination DB 112) or not is determined. When the answer information is detected in step ST56, it is determined that the answer information exists in the medical DB 110, and the routine advances to step ST58. At this time, the answer information is transmitted from the answer retrieving unit 102O to the terminal 10 via the input/output control unit 102A or the like. On the other hand, when the answer information is not detected in step ST56, it is determined that the answer information does not exist in the medical DB 110, and the routine advances to step ST59. At this time, one or more care elements included in the question element are transmitted as additional elements to the data updating unit 102P.

In step ST58, by the input/output control unit 12A, the answer information detected in step ST56 is visibly output in the display unit 13, and the routine returns to step ST49 in FIG. 16. In step ST58, for example, as shown in FIG. 33, when question sentences (question information) of "I am diabetic and am on a diet (18 units). When I drink a sports drink, what shall I do with food exchange?" written in the question box QA are entered, sentences of an answer (answer information) are visibly output such as "The calories of soft drinks are various. Some drinks contain many sugars, and some drinks use sweetener and do not contain sugars. In principle, sugar cannot be exchanged with xxx. Choose a drink with low calorie and little sugar by reading the ingredient labeling of a soft drink."

In step ST59, the data updating unit 102P adds the additional elements obtained in step ST57 to the disease-care-combination DB 112. In this case, the additional elements (care elements) are added to the disease-care-combination DB 112 in accordance with the question elements recognized in step ST55, and the routine returns to step ST49 in FIG. 16.

For example, in the case where the question element is a combination of one care element, one or more symptom elements, and one or more personal information elements, a new symptom-disease-personal information-care-combination information obtained by adding and combining the additional elements (care elements) to the combination of the one care element, one or more symptom elements, and one or more personal information elements in the disease-care-combination DB 112 is added to the disease-care-combination DB 112. For example, in the case where the question element is one care element, new symptom-disease-personal information-care-combination information generated by replacing the care element included in one or more pieces of symptom-disease-personal information-care-combination information already extracted by the care detecting unit 102I with the question element (one care element) may be added to the disease-care-combination DB 112. Further, for example, when the question element is a combination of one care element and other elements, new symptom-disease-personal information-care-combination information generated by replacing the care element in one or more pieces of symptom-disease-personal information-care-combination information including the combination of the other elements in the one or more symptom-disease-personal information-care-combination information already extracted by the care detecting unit 102I with the question element (one care element) may be added to the disease-care-combination DB 112.

Figure 34:
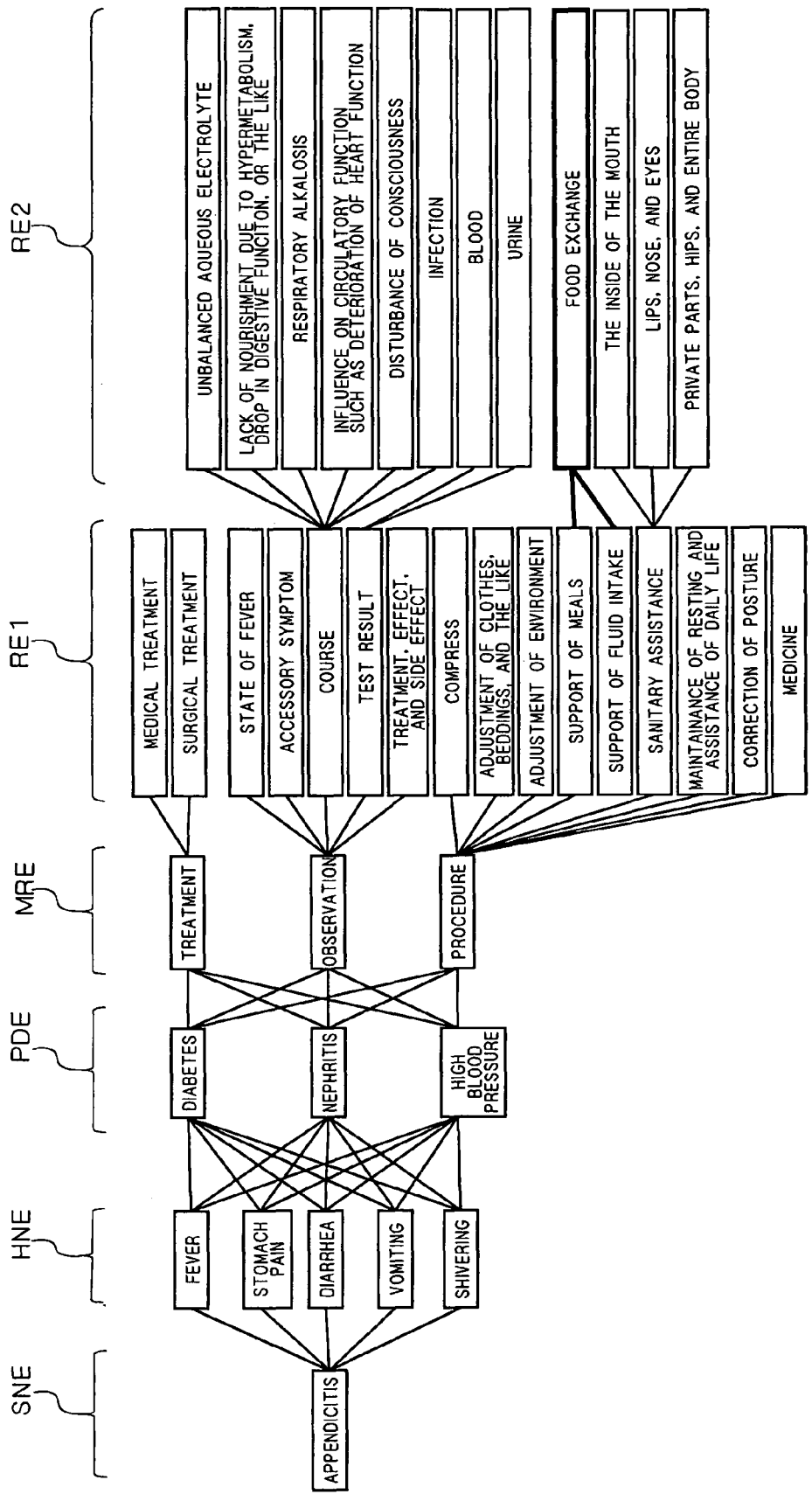
FIG. 34 is a diagram showing a state in which care elements are added to a disease-care-combination DB.

FIG. 34 is a diagram showing a mode of adding a care element to the disease-care-combination DB 112. FIG. 34 shows a state where a new care element "food exchange" RE2 is added by being associated so that the new care element "food exchange" RE2 depends from the care elements RE1 of "support of meals" and "support of fluid intake" included in the disease care information shown in FIG. 29.

As described above, only by entering a question in a normal sentence, a care element corresponding to the question is automatically added to the disease-care-combination DB 112. Thus, the work to enrich the information in the medical DB 110 can be reduced.

In the case where the routine advances to ST59, that is, in the case where answer information corresponding to the question element is not detected from the disease-care-combination DB 112, the information of a request to send the answer information corresponding to the question element to the user (answer request information) is transmitted from the answer retrieving unit 102O to the input/output control unit 102A. Under control of the input/output control unit 102A and the PC control unit 192, the answer request information is visibly output in the display unit 193. When the administrator of the system sees the answer request information visibly output, by properly obtaining the answer information from a doctor or the like, the administrator transmits the answer information to the user by an e-mail or the like. The detailed care element corresponding to the care element added to the disease-care-combination DB 112 in step ST59 is added to the medical DB 110 by the administrator of the system or the like.

In step ST60, whether the care element is adopted or not is determined by the adopted care designating unit 12D. As shown in FIG. 32, by clicking a command button SDB of "adopt the caring method" provided in a right lower part of the disease care screen ARi by an input operation on the operation unit 14 of the user in a state where the detailed care elements of the care element are visibly output in the detailed description box DBK, the one care element whose detailed care element is visibly output can be designated as an actually adopted element (adopted caring method element). Therefore, in step ST60, when one care element is designated as an actually adopted caring method element by the adopted care designating unit 12D in response to an input operation on the operation unit 14 of the user in a state where the disease care screen ARi is presented in the display unit 13, it is determined that the care element is adopted, and the routine advances to step ST61. The data element (adopted care element) indicative of an adopted caring method element is transmitted from the adopted care designating unit 12D to the server control unit 102 by the input/output control unit 12A. On the other hand, when the care element is not adopted, the routine returns to step ST49 in FIG. 16.

In step ST61, under control of the input/output control unit 12A and the like, a screen in which information can be added to electronic medical record information of a patient (hereinbelow, also called "electronic medical record input screen") is displayed in the support information display area AR in the nursing support screen G2.

FIG. 35 is a diagram showing an electronic medical record input screen ARk displayed in the support information display area AR in the nursing support screen G2. In the electronic medical record input screen ARk, a measurement value of the maximum blood pressure, a measurement value of the minimum blood pressure, and a measurement of body temperature can be selected in pull-down menus MX, MN, and TP, respectively, with the mouse pointer MP. As the measurement values, measurement values instructed to be measured in advance by a doctor or the like are used. The measurement values are designated from parameters (blood pressure, body temperature, blood sugar level, and the like) as indices of the health state of a human in accordance with the state of a patient and various conditions. By clicking a command button RC of "register the measurement values together with the symptom, disease name, and caring method" with the mouse pointer MP, information of the measurement values (measurement value information) selected in the menus MX, MN, and TP can be entered. When a command button RT of "return" is clicked in the electronic medical record input screen ARk, the routine returns to the state where the original disease care screen ARi is displayed. When a command button CL of "clear" is clicked, the measurement values selected in the pull-down menus MX, MN, and TP are erased.

In step ST62, whether measurement value information is entered or not is determined by the measurement value obtaining unit 12E. When a command button RC of "register the measurement values together with symptom, disease, and caring method" is clicked with the mouse pointer MP in a state where measurement values are selected in the menus MX, MN, and TP in the electronic medical record input screen ARk and the measurement value information is entered, the routine advances to step ST63. By the medical record information description control unit 102L, the measurement value information is obtained and the adopted care element designated by the adopted care designating unit 12D is obtained. On the other hand, when the command button RT of "return" is clicked in the electronic medical record input screen ARk, it is determined that the measurement value information is not entered, and the routine returns to step ST48 in FIG. 16.

In step ST63, by the control of the medical record information description control unit 102L and the control unit 202, the electronic medical record information stored in the medical record DB 210 is updated, and the routine returns to step ST48 in FIG. 16. One or more symptom elements and one disease name element are obtained from the detailed information detecting unit 102K by the medical record information description control unit 102L. The one or more symptom elements and the one disease name element and the measurement value information obtained in step ST62 and the adopted care element are transmitted as additional medical record information to be added to the electronic medical record to the hospital server 200 via the input/output control unit 102A and the like. By the control unit 202 in the hospital server 200, the additional medical record information is added to the electronic medical record information of the patient stored in the medical record DB 210, thereby updating the electronic medical record information. The electronic medical record information to which the information is added can be identified by using the medical record number entered in the general top screen G1. Therefore, for example, when the medical record number is not entered, designation of the adopted care element is inhibited.

By updating the electronic medical record information in such a manner, concerned doctors and health workers can view the electronic medical record information which is updated as needed, from the hospital server 200 and terminals connected to the hospital server 200. The patient himself/ herself and his/her family can log in the nursing support system and view the information from the terminals 10 to 40. Therefore, with such a configuration, at-home care and remote medical care can be enriched.

As described above, by the nursing supporting process in the nursing learning support system 1, when one or more symptoms are entered, disease names and a plurality of cares according to the one or more symptoms are visibly presented. Consequently, information of a desired caring method according to the situation can be easily obtained. Since a disease name can be detected from a plurality of symptoms, the precision of detecting a disease name can be increased. For example, by detecting a disease name in consideration of a plurality of main symptoms including accessory symptoms, the precision of detecting a disease name can be improved. Further, by detecting a disease name from a combination of a main symptom and a detailed symptom of the main symptom, the precision of detecting a disease name by narrowing down the symptoms can be improved. By narrowing down the detailed symptoms by region, degree, period, kind, amount, the number of times, the generation period, and the like, the precision of detecting a disease name can be further increased.

Only by entering a symptom in a natural sentence, the disease name corresponding to the symptom is detected. Therefore, anyone can easily enter a symptom.

When a desired care is designated in a state where the combination of the disease name according to the symptom and a plurality of cares is visibly presented, detailed information of the care is visibly presented. Consequently, detailed information of a desired caring method according to the situation can be easily obtained.

Only by entering information specifying the location of the personal information (in this case, the medical record number), the personal information is automatically recognized. Consequently, without performing complicated input operation of personal information, a caring method adapted to each patient can be known.

Learning Supporting Process

Outline of Learning Supporting Process

Figure 36:
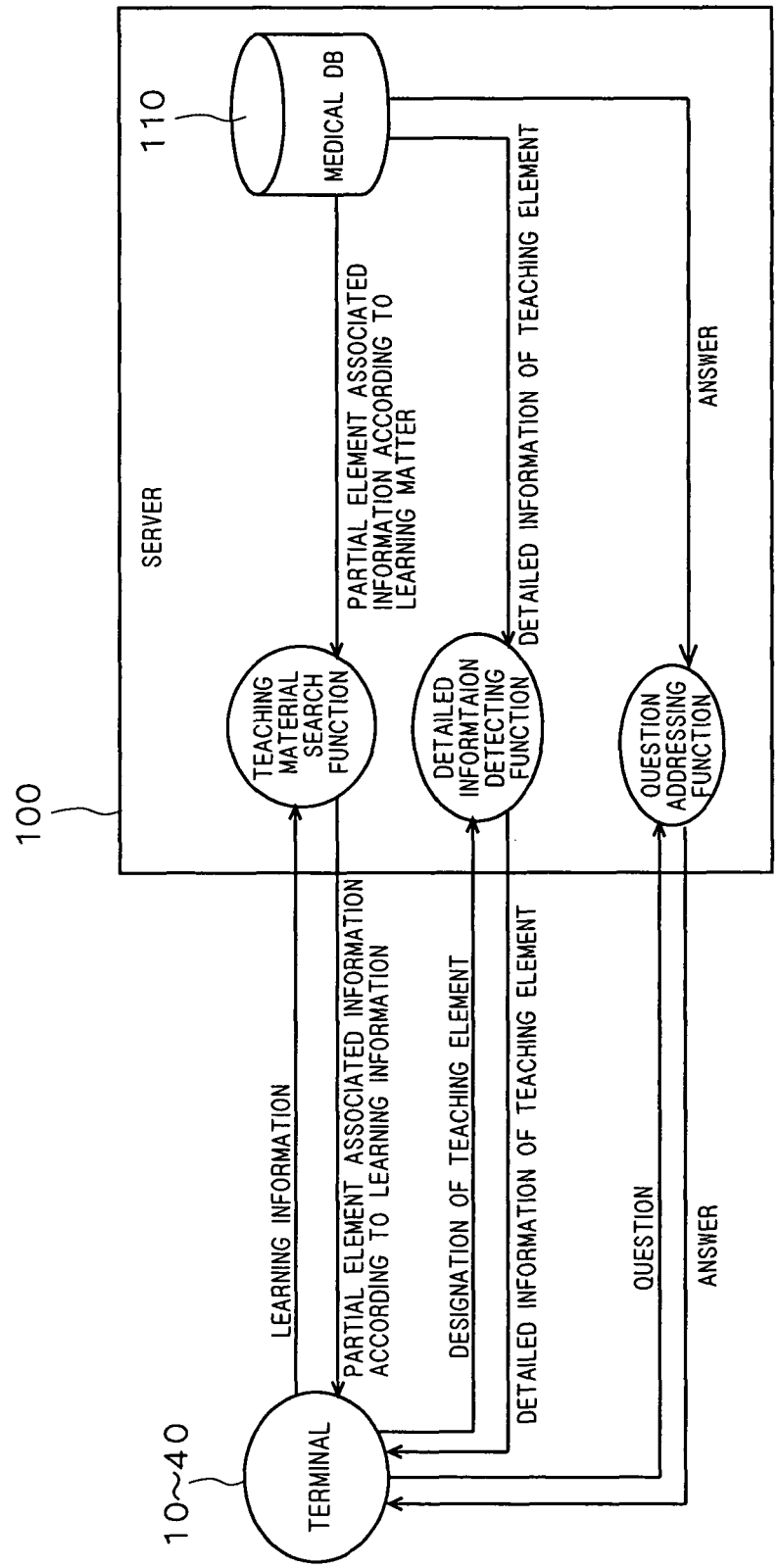
FIG. 36 is a diagram showing outline of information process operations in a learning supporting process.

FIG. 36 is a diagram showing outline of learning supporting process in the nursing learning support system 1.

When the user enters content desired to be learned in the terminals 10 to 40, by the teaching material search function of the server 100, a part of teaching element associated information (partial element associated information) according to the content desired to be learned is extracted from the medical DB 110 (concretely, the teaching element associated information 114) and visibly presented in the terminals 10 to 40. When the user designates a desired teaching element in the partial element associated information visibly presented in the terminals 10 to 40, detailed information of the teaching element is read from the medical DB 110 (concretely, the detailed data group 115) and visibly presented in the terminals 10 to 40.

When the user has a question, the user can enter the question in the terminals 10 to 40. When there is an answer to the question in the medical DB 110, the answer is visibly presented in the terminals 10 to 40. Although not shown, when the answer is not prepared in the medical DB 110, the answer is directly sent from a specialist or administrator to the terminals 10 to 40. As necessary, information of the question and the answer is added to the medical DB 110, thereby enriching the knowledge stored in the medical DB 110.

Data Stored in Medical DB in Learning Supporting Process

As described above, the teaching element associated information 114 is information obtained by associating a plurality of teaching elements indicative of items of teachings of a plurality of items including at least symptoms, diseases, and caring methods with each other. The teaching element associated information 114 is described in, for example, so-called RDF.

FIGS. 37 and 38 are diagrams showing concrete example of the teaching element associated information 114.

As shown in FIG. 37, in the teaching element associated information 114, a plurality of teaching elements "1. Basic nursing science", "2. Anatomic physiology", "3. Biochemistry", "4. Pharmacology", "5. Adult nursing science", "6. Child nursing science", "7. Maternal nursing science" . . . corresponding to learning items on nursing science are listed. To each of the teaching elements, further, one or more teaching elements are associated so as to belong to the teaching element. Teaching elements related to diseases are associated so as to systematically depend on the above-described teaching elements. In FIG. 37, the teaching elements belonging to the teaching element "5. Adult nursing science" are shown. Teaching elements belonging to the teaching elements of "1. Basic nursing science", "2. Anatomic physiology", "3. Biochemistry", "4. Pharmacology", "6. Child nursing science", "7. Maternal nursing science" . . . are not shown.

In FIG. 37, for the teachings of nursing science, there are a plurality of large items "1. Basic nursing science", "2. Anatomic physiology", "3. Biochemistry", "4. Pharmacology", "5. Adult nursing science", "6. Child nursing science", "7. Maternal nursing science" . . . and, for each of the large items, one or more small items exist (depend). In such a manner, in the teaching element associated information 114, each of teaching elements included in the plurality of teaching elements belongs to any of a plurality of hierarchical levels.

The plurality of teaching elements associated in the teaching element associated information 114 include one or more element (hereinbelow, also called "element with a detailed item") on which one or more elements indicative of detailed items constructing a teaching (hereinbelow, also called "detailed item element") depend (are linked). That is, each of a plurality of teaching elements has one or more detailed item element and one or more element with a detailed item.

FIG. 38 shows a state in which teaching elements further depend on the teaching elements of diseases included in the teaching element associated information shown in FIG. 37.

As shown in FIG. 38, for example, on the element "appendicitis" with detailed items, six detailed item elements "occurrence mechanism", "test", "symptom", "complication", "caring method", and "medicine" of the disease depend. The "occurrence mechanism", "test", "symptom", "complication", "caring method", and "medicine" in this case correspond to elements with detailed items of the disease to which the elements depend. On the element "symptom" with detailed items, detailed item elements "fever", "stomachache", "nausea and vomiting", "chill and rigor", "diarrhea", and "constipation" depend.

Detailed data (combination information of number, sign, and the like specifying the location of the detailed data) is linked to each of the detailed item elements "fever", "stomachache", "nausea and vomiting", "chill and rigor", "diarrhea", and "constipation". The substantial data of the detailed data is stored in the detailed data group 115 so as to be associated with the combination information such as number and sign specifying the location of the detailed data. For example, the detailed data of the detailed item elements of the caring method can be also used as the detailed care elements used for the nursing supporting process. FIG. 38 shows only the detailed item elements belonging to the teaching element "symptom" as one of the six detailed item elements belonging to the element "appendicitis" with detailed items. Also to the other five teaching elements, detailed item elements and detailed data belong.

To the detailed item element "caring method" belonging to the element with detailed items of each disease, detailed item elements indicative of two or more cares belong. Detailed data belonging to the two or more detailed item elements is formed on the basis of at least one of nursing learning information, a nursing method, and nursing knowledge so that the user can effectively learn knowledge of nursing.

To enable knowledge to be supplied according to levels of the users, detailed item elements indicative of cares corresponding to users at different two or more levels may belong to the detailed item element "caring method". The detailed data of the detailed item element belonging to the detailed item element "caring method" may include detailed data according to caring methods corresponding to the users at different two or more levels.

Further, a detailed item element indicative of a care of at least one of items of procedure, caring method, follow-up, initial care, medicine, and test may belong to the detailed item element "caring method" or detailed data of a caring method may include detailed data of at least one of items of procedure, caring method, follow-up, initial care, medicine, and test so that the user can know multiple caring methods.

To the detailed item element of the symptom such as "fever", detailed item elements of "occurrence mechanism", "complication", and the like may belong. To the detailed item elements of a symptom, detailed item elements of at least one of region, degree, period, kind, amount, the number of times, and occurrence timing may properly belong.

Functional Configuration of Learning Supporting Process Functions of Terminal Control Unit 12

Figure 39:
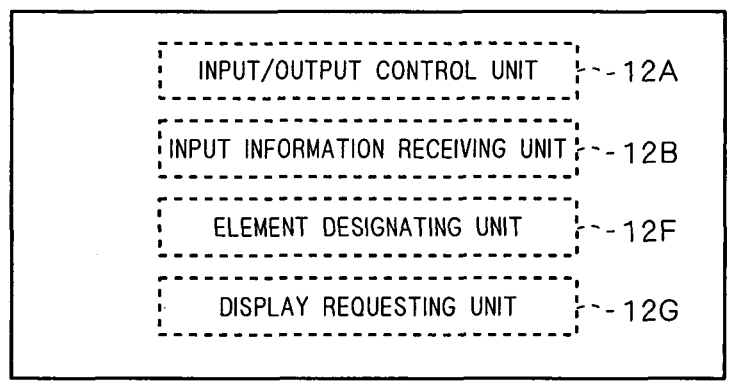
FIG. 39 is a block diagram showing functions realized by a terminal control unit.

FIG. 39 is a diagram showing the functions realized by the terminal control unit 12 when the learning supporting process is executed. When the learning supporting process is executed, the terminal control unit 12 has, as functions, the input/output control unit 12A, the input information receiving unit 12B, an element designating unit 12F, and a display requesting unit 12G. The same reference numerals are designated to the input/output control unit 12A and the input information receiving unit 12B as functions similar to those used in the nursing supporting process, and their description will not be repeated.

The element designating unit 12F designates one of a plurality of teaching elements included in the partial element associated information (specifically, network information obtained by associating a plurality of teaching elements with each other in a network shape) in response to a predetermined input operation on the operation unit 14 of the user in a state where the partial element associated information is visibly output in the display unit 13 under control of the input/output control unit 12A. Information indicative of the one teaching element (hereinbelow, also called "teaching element designation information") designated by the element designating unit 12F is transmitted to the server control unit 102 (concretely, a detailed data extracting unit 102U which will be described later) by the input/output control unit 12A.

The display requesting unit 12G requests for display of one or more detailed item elements belonging to one element with detailed items included in the partial element associated information in response to a predetermined input operation on the operation unit 14 of the user in a state where the partial element associated information (that is, the network information) is visibly output except for part of the detailed item elements included in the partial element associated information in the display unit 13 under control of the input/output control unit 12A.

Functions of Server Control Unit 102

Figure 40:
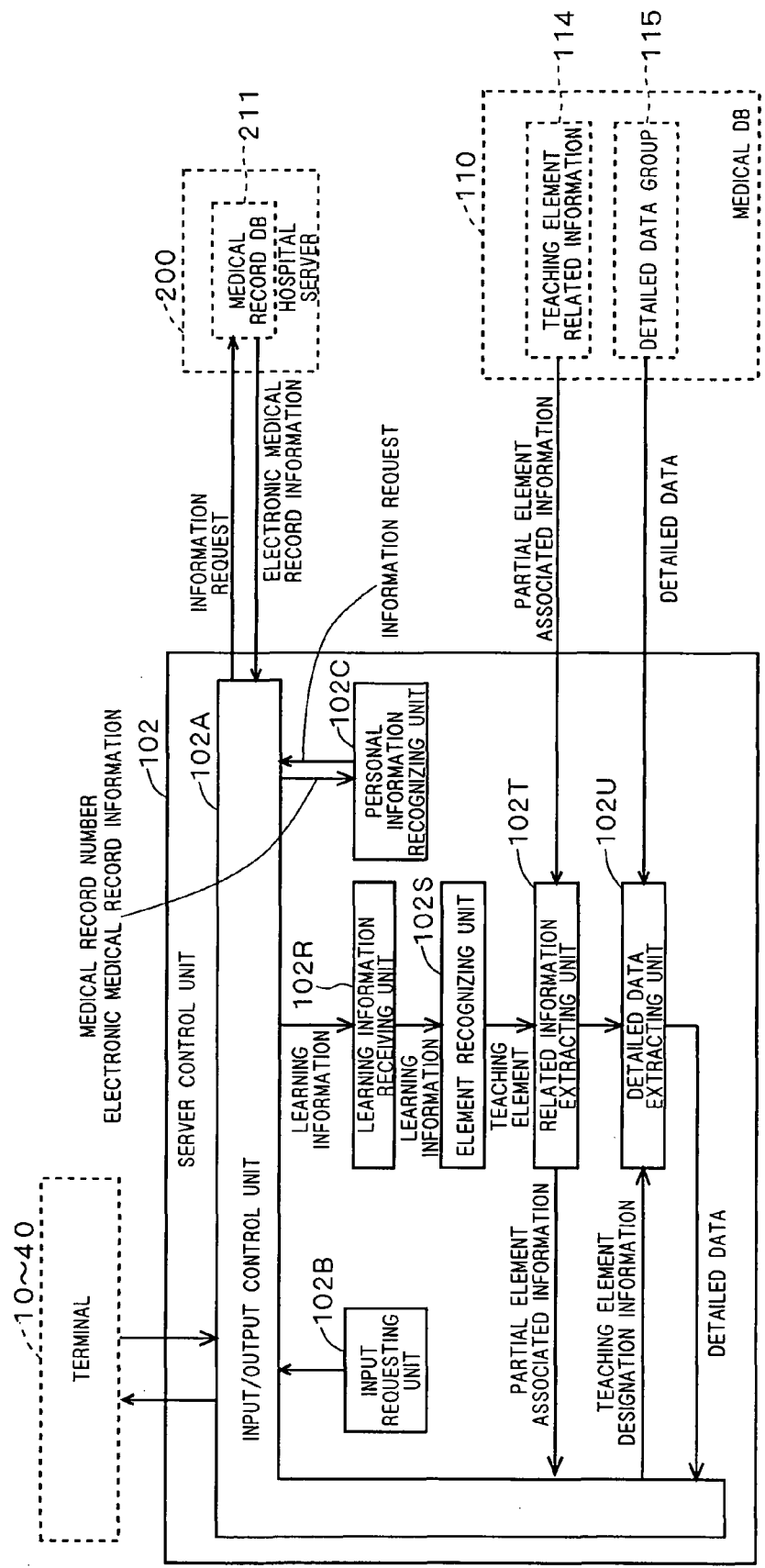
FIG. 40 is a block diagram showing functions realized by a server control unit.

FIG. 40 is a diagram showing functions realized by the server control unit 102 at the time of executing the learning supporting process.

At the time of executing the learning supporting process, the server control unit 102 has, as functions, the input/output control unit 102A, the input requesting unit 102B, the personal information recognizing unit 102C, a learning information receiving unit 102R, an element recognizing unit 102S, a related information extracting unit 102T, and the detailed data extracting unit 102U. Since the input/output control unit 102A, the input requesting unit 102B, and the personal information recognizing unit 102C have the same configurations as those described in the nursing supporting process, so that the same reference numerals are designated. Only different points will be described. The server control unit 102 also has functions similar to those shown in FIG. 13.

The learning information receiving unit 102R receives learning information in response to a predetermined input operation on the operation unit 14 of the user. The learning information is information indicative of one teaching element and is, for example, information indicative of one teaching element of a disease. The learning information receiving unit 102R transmits the learning information to the element recognizing unit 102S.

The element recognizing unit 102S recognizes one teaching element from the learning information obtained from the learning information receiving unit 102R. For example, one teaching element of a disease is recognized. The element recognizing unit 102S transmits the recognized teaching element to the related information extracting unit 102T.

The related information extracting unit 102T extracts, from the teaching element associated information 114, a plurality of teaching elements including one teaching element recognized by the element recognizing unit 102S, and a teaching element having a predetermined relation with the one teaching element, and a part of information showing the association among the plurality of teaching elements (hereinbelow, also called "partial element associated information"). The predetermined relation is that the teaching element belongs to the one teaching element recognized by the element recognizing unit 102S. The predetermined relation is that, for example, two or more teaching elements of a caring method belong to one teaching element of a disease. The related information extracting unit 102T transmits the extracted partial element associated information to the terminals 10 to 40 via the input/output control unit 102A or the like.

On the basis of element designation information obtained from the element designating unit 12F via the input/output control unit 102A or the like, the detailed data extracting unit 102U extracts detailed data corresponding to one teaching element indicated by the element designation information from the detailed data group 115. The detailed data extracting unit 102U transmits the extracted detailed data to the terminals 10 to 40 via the input/output control unit 102A or the like.

Operations of Learning Supporting Process

Figure 41:
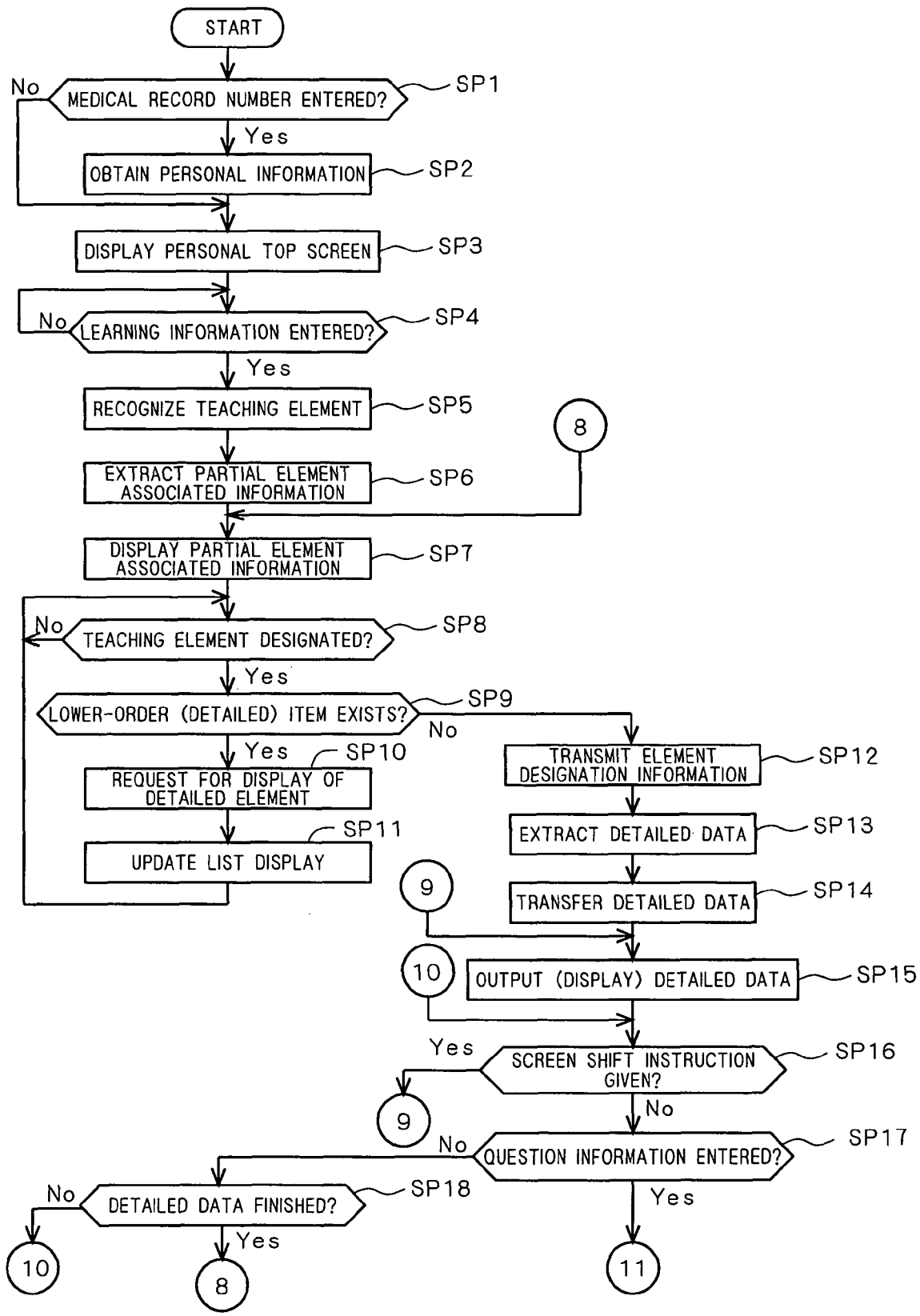
FIGS. 41 and 42 are flowcharts showing the operation flow of the learning supporting process.
Figure 42:
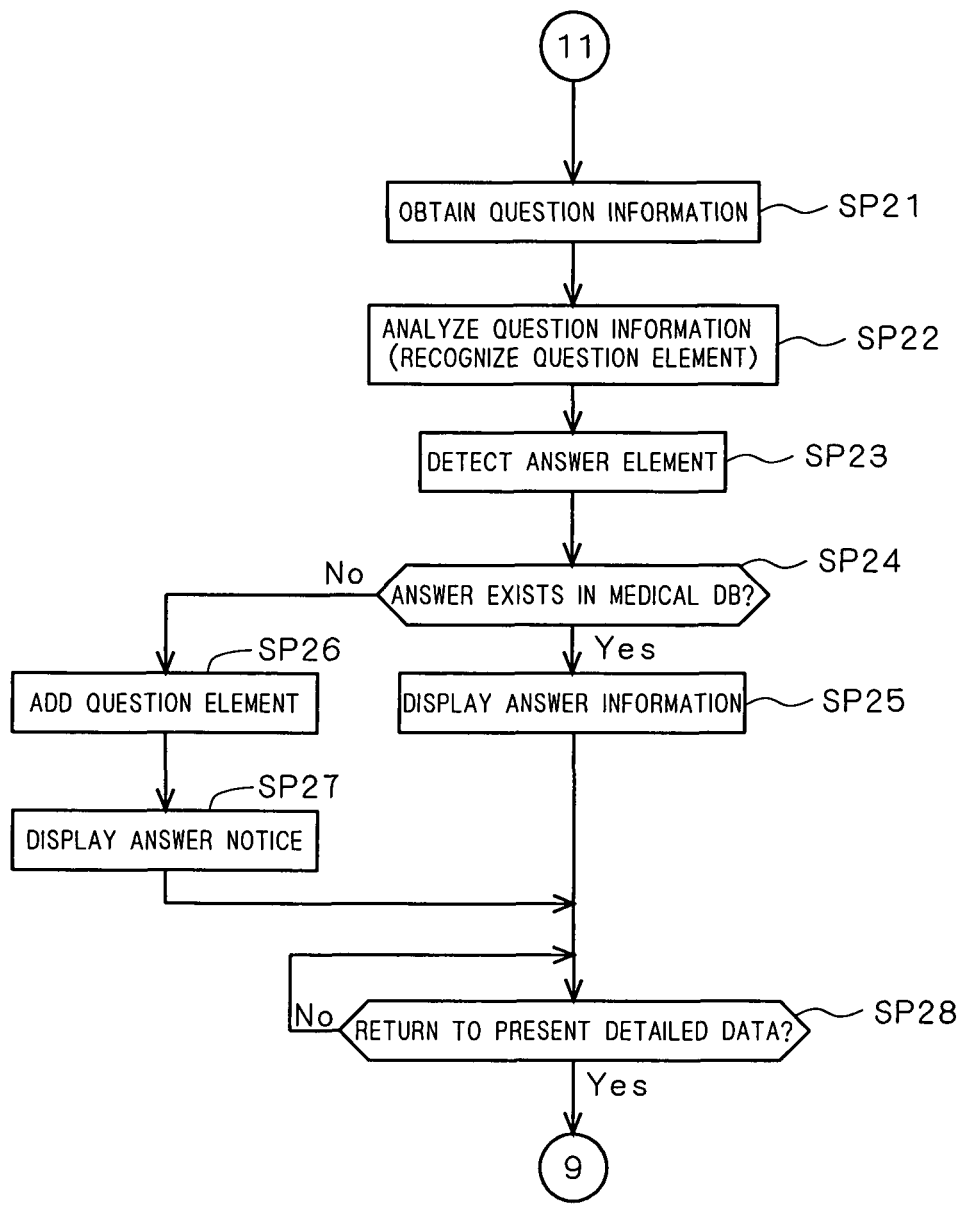

FIGS. 41 and 42 are flowcharts showing the flow of operations of the learning supporting process, which is an operation flow executed when the routine advances to step S5 in FIG. 14. FIGS. 43 to 52 are diagrams showing screens visibly presented in the terminals 10 to 40 in the learning supporting process operations. In the following, an example that the user uses the nursing learning support system 1 in the terminal 10 as one of the terminals 10 to 40 will be described.

When the routine advances to step S5 in FIG. 14, the flow of the learning supporting process operations shown in FIGS. 41 and 42 starts, and the routine advances to step SP1.

In step SP1, like in step ST1 in FIG. 15, whether a medical record number is entered in the general top screen G1 or not is determined by the personal information recognizing unit 102C. When it is determined that a medical record number is entered, the routine advances to step SP2. When it is determined that a medical record number has not been entered, the routine advances to step SP3.

In step SP2, like in step ST2 in FIG. 15, the personal information recognizing unit 102C obtains electronic medical record information (that is, personal information) corresponding to the medical record number entered by the user from the medical record DB 210. The personal information recognizing unit 102C requests the hospital server 200 to transmit the electronic medical record information on the basis of the input medical record number. The electronic medical record information is transmitted from the hospital server 200 to the server 100 via the input/output control unit 102A and the like.

In step SP3, the personal top screen of the learning support system is displayed by the server control unit 102 and the terminal control unit 12.

FIG. 43 is a diagram showing a screen G11 displayed on the display unit 13 (hereinbelow, also called "learning support screen") after log-in of the learning support system. A wide area extending to the left from the center in the learning support screen G11 is an area (support information display area) AE in which various learning support information is displayed. On the right part of the learning support screen G11, command buttons B10 to B40 in which various commands can be entered are arranged in order from top.

FIG. 44 is a diagram showing a screen (hereinbelow, also called "personal top screen") AEa displayed in the support information display area AE in the learning support screen G2 after log-in. In an upper-half area LS1 of the personal top screen AEa, teaching elements of nursing are displayed systematically. FIG. 44 shows an example of visibly outputting the information illustrated in FIG. 37. The user can enter learning information indicative of a desired teaching element by operating the operation unit 14 to properly place the mouse pointer MP on the desired teaching element in a plurality of teaching elements displayed in the area LS1 and to click the left button of the mouse.

In a lower-half area LS2 of the personal top screen AEa, the teaching elements (for example, "fever", "headache", "vomiting", . . . ) of symptoms included in the teaching element associated information 114 are listed. The user can enter the learning information of a teaching element of a desired symptom by operating the operation unit 14 to properly place the mouse pointer MP on the desired symptom in the plurality of symptoms listed in the area LS2 and clicking the left button of the mouse.

At the time of selecting a desired teaching element on the personal top screen AEa, in the case where the user has not obtained knowledge which should be acquired in advance, it is also possible not to allow the user to select the desired teaching element as long as the user does not obtain the knowledge. For example, even when the user wishes to learn "appendicitis", the user cannot learn it as long as the user does not obtain the knowledge of "basic nursing science", "anatomic physiology", "biochemistry", "pharmacology", and the like.

In step SP4, whether the learning information is entered or not is determined by depending on whether the learning information receiving unit 102R has received the learning information or not. The determination in step SP4 is repeated until learning information is entered in the personal top screen AEa. When learning information is entered, it is received by the learning information receiving unit 102R, and the routine advances to step SP5.

In step SP5, a teaching element is recognized from the learning information received in step SP4 by the element recognizing unit 102S. For example, when a desired teaching element "appendicitis" is entered in the personal top screen AEa, the teaching element "appendicitis" is recognized as it is.

In step SP6, the related information extracting unit 102T extracts partial element associated information of a plurality of teaching elements including the teaching element recognized in step SP5 and a teaching element having a predetermined relation with the teaching element. For example, when the teaching element "appendicitis" is recognized in step SP5, partial element associated information including the teaching element "appendicitis" and one or more teaching elements belonging to the teaching element "appendicitis" are extracted. The partial element associated information is transmitted to the terminal 10 via the input/output control unit 102A or the like.

In step SP7, under control of the input/output control unit 12A of the terminal 10, on the basis of the partial element associated information extracted in step SP6, a screen (hereinbelow, also called "network information screen") to which network information obtained by associating the teaching elements with each other so as to form a network is visibly output is displayed on the display unit 13.

When all of the teaching elements included in the partial element associated information are visibly output, the number of teaching elements displayed at once becomes too large, and there is the possibility that the viewability of the network information screen becomes poor. Consequently, by the control of the input/output control unit 12A, network information obtained by associating only teaching elements belonging to a predetermined number of levels from the highest level of the partial element associated information with each other so as to form a network is visibly output. In other words, network information is visibly output, which is obtained by associating teaching elements with each other so as to form a network except for teaching elements other than the teaching elements belonging to the predetermined number of levels from the highest level of the partial element associated information among a plurality of teaching elements included in the partial element associated information. The predetermined number of levels may be, for example, a few levels.

Figure 45:
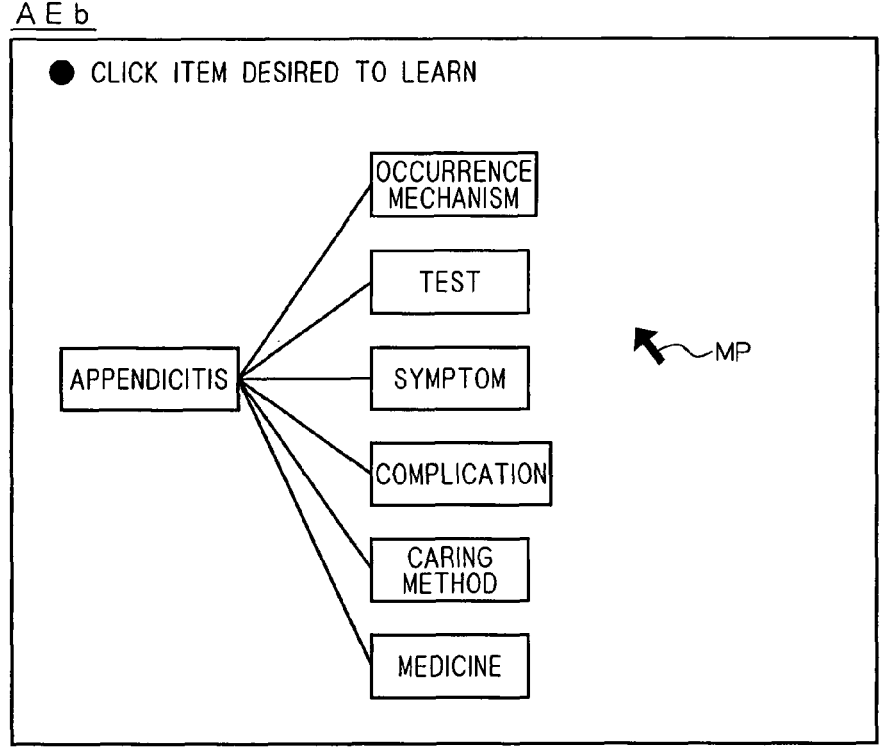
FIGS. 45 and 46 are diagrams showing display examples of partial element associated information.

FIG. 45 is a diagram showing a network information screen AEb displayed in the support information display area AE in the learning support screen G11. The network information screen AEb displays the screen which is displayed in the case where the partial element associated information shown in FIG. 38 is extracted in step SP6. As shown in FIG. 45, in the network information screen AEb, the teaching element "appendicitis" and six teaching elements "occurrence mechanism", "test", "symptom", "complication", "caring method", and "medicine" directly belonging to the teaching element "appendicitis" are associated with each other. That is, the diagram shows the case where the predetermined number of levels is two. In the network information screen AEb, the user can designate a desired teaching element by the element designating unit 12F by operating the operation unit 14 to place the mouse pointer MP on the desired teaching element and clicking the left button of the mouse.

In step SP8, whether a teaching element is designated by the element designating unit 12F or not is determined. For example, in the network information screen AEb as shown in FIG. 45, when the mouse pointer MP is placed on a teaching element and the left button of the mouse is clicked, it is determined that the teaching element is designated, and the routine advances to step SP9. On the other hand, the process of step SP8 is repeated until a teaching element is designated.

In step SP9, the terminal control unit 12 determines whether a detailed item element belongs to the teaching element designated in step SP8, that is, the teaching element designated in step SP8 is an element with a detailed item or not. By referring to the partial element associated information extracted in step SP6, when the teaching element designated in step SP8 is an element with detailed items, the routine advances to step SP10. On the other hand, when the teaching element designated in step SP8 is not an element with detailed items, the routine advances to step SP12.

In step SP10, display of the detailed item elements belonging to the element with the detailed items designated in step SP8 is requested by the display requesting unit 12G.

In step SP11, in response to the request in step SP10, display in the display unit 13 is updated by the control of the input/output control unit 12A, and the routine returns to step SP8. Concretely, by the control of the input/output control unit 12A, one or more detailed item elements directly belonging to the element with detailed items designated in step SP8 are visibly output on the basis of the partial element associated information extracted in step SP6. As long as an element with detailed items is designated, the processes in steps SP8 to SP11 are repeated.

Figure 46:
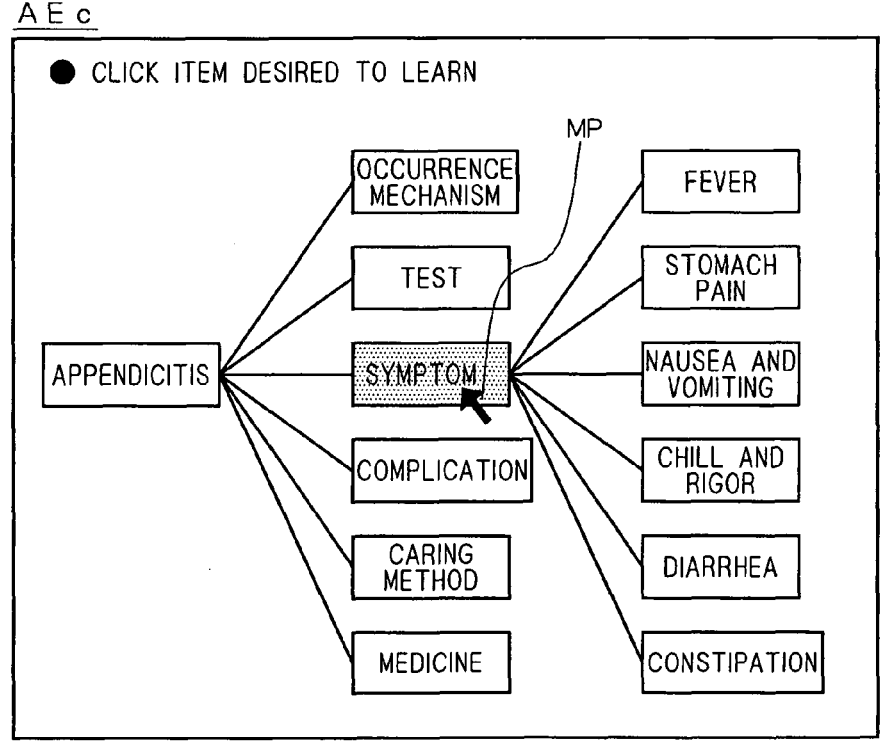

FIG. 46 is a diagram showing a network information screen AEc displayed in the support information display area AE in the learning support screen G11. For example, by placing the mouse pointer MP on the element "symptom" with detailed items and clicking the left button of the mouse in the network information screen AEb shown in FIG. 45, as shown in FIG. 46, a network information screen AEc in which detailed item elements "fever", "stomachache", "nausea and vomiting", "chill and rigor", "diarrhea", and "constipation" directly belonging to the "symptom" with detailed items are visibly output is displayed in the support information display area AE. A line connecting elements in the network information screen AEc indicates direction association. In the case where the user wishes to learn "symptom" or the like of the "appendicitis", by clicking "symptom", items related to "symptom" are displayed.

As described above, a plurality of teaching elements which are initially limited to main teaching elements are associated with each other so as to form a network shape and presented visibly. In response to a request from the user, detailed teaching elements of the main items are visibly presented. Consequently, the user can easily find a desired teaching item, and can easily obtain desired detailed information. Further, viewability of detailed teaching items improves.

In step SP12, the element designating unit 12F transmits the teaching element designation information to the detailed data extracting unit 102U.

In step SP13, the detailed data extracting unit 102U extracts detailed data corresponding to the teaching element designation information from the detailed data group 115 on the basis of the teaching element designation information transmitted in step SP12.

In step SP14, the detailed data extracted in step SP13 is transferred from the detailed data extracting unit 102U to the terminal 10 via the input/output control unit 102A or the like.

In step SP15, on the basis of the detailed data transferred in step SP14, the detailed data is visibly output in the display unit 13 by the input/output control unit 12A.

FIGS. 47 and 48 are diagrams showing a screen (hereinbelow, also called "comment display screen") displayed in the support information display area AE in the learning support screen G11 and displaying a comment on the teaching element on the basis of the detailed data of the teaching element. FIG. 47 shows a comment display screen AEd displayed on the display unit 13 on the basis of the detailed data of the detailed item element "occurrence mechanism" belonging to the element "appendicitis" with detailed items. FIG. 48 shows a comment display screen AEe displayed on the display unit 13 on the basis of the detailed data of the detailed item element "occurrence mechanism" belonging to the detailed item element "fever" belonging to the element "appendicitis" with detailed elements.

The user can learn the details of the teaching element with reference to the comment display screens AEd and AEe. In each of the comment display screen AEd and AEe, four command buttons "next", "back", "end", and "question" are provided. By clicking a command button with the mouse pointer MP, the command corresponding to the button can be instructed. The command button "next" instructs a shift to the next screen on the basis of the detailed data. The command button "back" instructs a shift to the screen immediately previously displayed on the basis of the detailed data. The command button "end" instructs end of display based on the detailed data. The command button "question" instructs a shift to a question entry screen (which will be described later).

In step SP16, whether a screen shift is instructed or not is determined by the terminal control unit 12. When any of the command buttons "next", "back", and "question" is clicked, it is determined that the screen shift instruction is given, and the routine returns to step SP15. In the case where the command button "next" is clicked and the routine returns to step SP15, the next screen is displayed on the basis of the detailed data transferred in step SP14. When the command button "back" is clicked and the routine returns to step SP15, the immediately preceding screen is displayed on the basis of the detailed data transferred in step SP14. Further, when the command button "question" is clicked and the routine returns to step SP15, the question entry screen (which will be described later) is displayed on the basis of the detailed data transferred in step SP14. When there is no screen shift instruction in step SP16, the routine advances to step SP17.

Figures 49, 50:
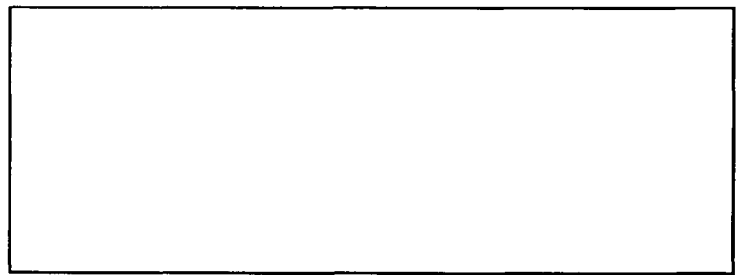
FIG. 49 is a diagram showing a display example of a question display screen.
FIG. 50 is a diagram showing a display example of a question entry screen.

FIG. 49 is a diagram showing a screen AEf displaying a question on a teaching element (hereinbelow, called "question display screen"), which is displayed in the support information display area AE of the learning support screen G11 on the basis of the detailed data of the teaching element. FIG. 49 illustrates a question display screen displayed after the comment display screen, on the basis of the detailed data of the detailed item elements "fever", "stomachache", "nausea and vomiting", "chill and rigor", "diarrhea", and "constipation" belonging to the detailed item element "symptom" belonging to the element "appendicitis" with detailed items.

In the question display screen AEf, a question sentence is presented in an upper part of the screen, an answer column in which characters and signs can be entered is provided in a center portion of the screen, and command buttons "answer" and "clear" are provided in a lower part. The user enters characters and the like in the answer column in the question display screen AEf by properly operating the operation unit 14 and can enter the data written in the answer column by clicking the command button "answer" with the mouse pointer MP. When the command button "clear" is clicked with the mouse pointer MP, the data written in the answer column is erased. The screen based on the detailed data of the detailed item element to be learned may be automatically displayed next according to the answer. For example, in the case where only "fever" is answered as a symptom of appendicitis, a comment display screen based on the detailed data of the detailed item elements of the remaining symptoms may be automatically displayed. When all of the symptoms cannot be answered, the program may not be allowed to go to an advanced item. For example, when the user does not know "symptoms", the program may not be allowed to go to the detailed item element "complication".

FIG. 50 is a diagram showing a screen AEg for accepting writing of a question (hereinbelow, also called "question entry screen"), which is displayed in the support information display area AE in the learning support screen G11 on the basis of the detailed data of the teaching element. As shown in FIG. 50, in the question entry screen AEg, a question entry column for writing a question in a natural sentence is provided in a center portion of the screen, and the command buttons "transmit" and "clear" are provided in a lower part of the screen. The user properly operates the operation unit 14 to enter characters and the like in the question entry column and clicks the command button "transmit" with the mouse pointer MP. In such a manner, the question information indicative of the writing in the question entry column can be entered. When the command button "clear" is clicked with the mouse pointer MP, the data written in the question entry column is erased. At this time, the question information is transmitted to the question information receiving unit 102M.

In step SP17, whether the question information is entered or not is determined by the terminal control unit 12. For example, when the command button "transmit" is clicked in the question entry screen AEg, it is determined that the question information is entered, the routine advances to step SP21 in FIG. 42. On the other hand, when the question information is not entered, the routine advances to step SP18.

In step SP18, whether output of the detailed data transferred in step SP14 is finished or not is determined by the input/output control unit 12A. When the command button "end" in FIGS. 47 and 48 is clicked or when the command button "answer" in FIG. 49 is clicked, it is determined that output of the detailed data is finished, the routine returns to step SP7, and the partial element associated information is displayed. On the other hand, when output of the detailed data is not finished, the routine returns to step SP16.

In step SP21 in FIG. 42, the question information entered by the terminal control unit 12 is obtained by the question information receiving unit 102M.

In step SP22, the question information analyzing unit (question element recognizing unit) 102N performs a language analysis (a language analysis using data for morphological analysis, data for dependency structure analysis, keyword data, and dictionary data) on the question information received by the question information receiving unit 102M in step SP21, thereby recognizing a question element including at least one teaching element. The question element recognized at this time may be an element of any form of a long form, a paragraph, and a term, or combination of one or more elements of any of a long form, a paragraph, and a term. Examples of the question element are one teaching element and a combination of one or more symptom elements.

In step SP23, the answer retrieving unit 102O searches the medical DB 110 (concretely, the teaching element associated information 114 and the detailed data group 115) for detailed data (that is, answer information) of the detailed item element corresponding to the question element recognized in step SP22. When the question element is one teaching element, detailed data of the one teaching element is simply detected from the medical DB 110 (concretely, the detailed data group 115). When the question element is a combination of a plurality of teaching elements, the combination (that is, association) of teaching elements is extracted from the teaching element associated information 114, and the detailed data of the teaching element at the lowest order is detected from the medical DB 110 (concretely, the detailed data group 115).

In step SP24, whether the answer information corresponding to the question element recognized in step SP22 exists in the medical DB 110 (concretely, the detailed data group 115) or not is determined by the answer retrieving unit 102O. When the answer information is detected in step SP23, the routine advances to step SP25. At this time, the answer information is transmitted by the answer retrieving unit 102O to the terminal 10 via the input/output control unit 102A or the like. On the other hand, when the answer information is not detected in step SP23, the routine advances to step SP26. At this time, the question element is transmitted as an additional element to the data updating unit 102P.

In step SP25, by the input/output control unit 12A, the answer information detected in step SP23 is visibly output in the display unit 13, and the routine advances to step SP28.

Figures 51, 52:
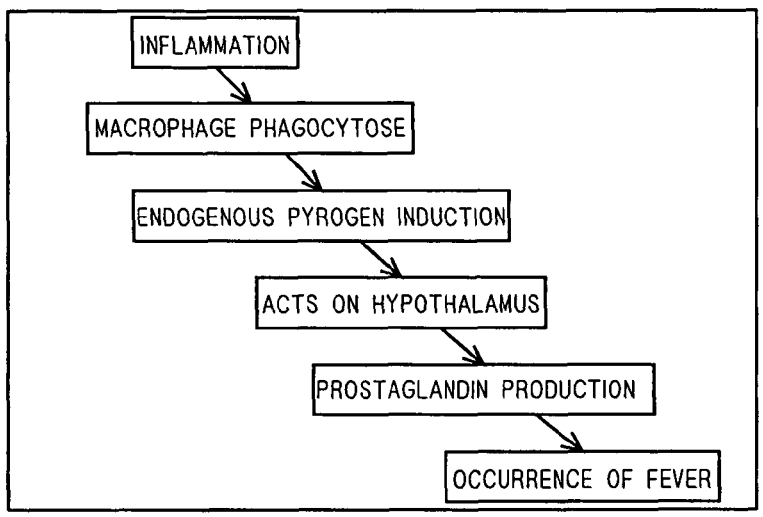
FIGS. 51 and 52 are diagrams showing display examples of an answer display screen.

FIG. 51 is a diagram showing a screen AEh displaying an answer to a question (hereinbelow, also called "answer display screen"), which is displayed in the support information display area AE in the learning support screen G11 on the basis of detailed data of the teaching element. In FIG. 51, when a question sentence (question information) of "Why does appendicitis occur?" written in the question entry column is entered, a combination between the element "appendicitis" with detailed items and the detailed item element "occurrence mechanism" is recognized in step S22. The detailed data indicative of the detailed item element "occurrence mechanism" at the lowest level in the combination between the element "appendicitis" with detailed items and the detailed item element "occurrence mechanism" is detected in step SP23. On the basis of the detailed data, the description of the detailed item element "occurrence mechanism" is visibly presented. In the answer display screen AEh, the command button "return" provided in the lower part of the screen is clicked with the mouse pointer MP, thereby enabling an instruction to return to the screen displayed immediately before the question entry screen to be given.

In step SP26, the question element (teaching element) recognized in step SP22 is added to the teaching element associated information 114 by the data updating unit 102P. On the basis of the analysis result in step SP22, the teaching element which should belong such as a disease name and a symptom is determined. For example, when the question element is the combination of the teaching element "appendicitis" and the detailed item element "occurrence mechanism", the detailed item element "occurrence mechanism" is added so as to belong to the teaching element "appendicitis". Generally, by the data updating unit 102P, one or more new teaching elements recognized by the question information analyzing unit 102N for recognizing the teaching elements are added to the teaching element associated information 114 and associated with at least one other teaching element.

As described above, when the user just enters a question in a natural sentence, the teaching element corresponding to the question is automatically added to the medical DB 110. Consequently, the teaching materials can be enriched in response to the needs of the user, and the work to enrich information in the database can be lessened.

In step SP27, by the control of the answer retrieving unit 102O and the terminal control unit 12, a notice to answer later (answer notice) is displayed in the display unit 13. FIG. 52 is a diagram showing the answer display screen AEi displaying an answer notice. In the answer display screen AEi, by clicking the command button "back" provided in the lower part of the screen with the mouse pointer MP, an instruction to return to the screen display immediately before the question entry screen can be given.

Under control of the input/output control unit 102A and the PC control unit 192, the answer request information is visibly output in the display unit 193. When the administrator of the system sees the answer request information which is visibly output, by obtaining the answer information from a doctor or the like, the administrator transmits the answer information to the user by an e-mail or the like. The detailed data corresponding to the teaching element added to the teaching element associated information 114 in step SP26 is added to the medical DB 110 by the administrator of the system or the like. By addition of the element and detailed data to the medical DB 110, the learning content is enriched, and a learning effect can be improved.

In step SP28, whether the program returns to visible output of the detailed data transferred in step SP14 or not is determined by the terminal control unit 12. When the command button "back" provided in the lower part of the screen is clicked with the mouse pointer MP in the answer display screen AEh or AEi, an instruction to return to the screen displayed immediately before the question entry screen is given, and the routine returns to step SP15 in FIG. 41. In this case, the program returns to the screen displayed immediately before the shift to the question entry screen. Until the instruction to return to the screen displayed immediately before the question entry screen is given, the determination in step SP28 is repeated.

As described above, when data to learn about a disease is entered, partial element associated information including at least a teaching item on the disease and two or more teaching items on a caring method belonging to the teaching item is extracted. On the basis of the partial element associated information, a plurality of teaching elements are associated with each other so as to form a network shape and presented visibly. Consequently, the user can easily obtain information on a desired caring method according to the situations.

When a desired teaching element is designated in a state where a plurality of teaching elements are associated so as to form a network shape and presented visibly, the detailed data of the designated teaching element is presented visibly. Consequently, the user can easily obtain detailed information on a desired caring method according to the situations.

Modifications

Although the embodiment of the present invention has been described above, the invention is not limited to the above description.

For example, in the foregoing embodiment, as shown in FIGS. 8 to 10, in the disease-care-combination DB 112, a detailed element specifying number corresponding to one detailed care element is included for each of the symptom-disease-personal information-care-combination information shown line by line. Instead, two or more detailed element specifying numbers corresponding to two or more detailed care elements may be included for each of the symptom-disease-personal information-care-combination information. In such a case, for example, detailed description of one care element may be constructed by two or more detailed care elements. A concrete example will be described below.

FIG. 53 is a diagram showing a concrete example of information of the disease-care-combination DB 112 in a modification. FIG. 54 is a diagram showing a concrete example of information of the detailed data group 115 in the modification. FIG. 55 is a diagram showing a state where a detailed care element is visibly output in the detailed description box DBK in the disease-care screen ARi in the modification.

As shown in FIG. 53, in the disease-care-combination DB 112, two or more detailed element specifying numbers corresponding to two or more detailed care elements are included for each of the symptom-disease-personal information-care-combination information shown line by line. As shown in FIG. 54, in the detailed data group 115, the detailed care elements are stored so as to be associated with the detailed element specifying numbers (1 to 7 in FIG. 54).

At the time of visibly outputting the detailed care elements corresponding to the symptom-disease-personal information-care-combination information, two or more detailed care elements corresponding to two or more detailed element specifying numbers included in the symptom-disease-personal information-care-combination information in the disease-care-combination DB 112 shown in FIG. 53 are read from the detailed data group 115 shown in FIG. 54 and combined. The resultant elements are visibly output in the display unit 13.

For example, in the case where it is requested to visibly output the detailed care elements on the symptom-disease-personal information-care-combination information of a combination of the symptom element "chill and rigor (chill and shaking)"—symptom element "fever"—symptom element "high fever"—symptom element "short time"—disease name element "adenoiditis"—past disease "scleroderma"—detailed initial care element "consult a doctor"—care classification element "procedure"—care name "(hot or cold) compress"—detailed element specifying numbers "2, 4, 5, 6, 7" in the plurality of pieces of symptom-disease-personal information-care-combination information shown in FIG. 53, five detailed care elements corresponding to the five detailed element specifying numbers 2, 4, 5, 6, and 7 shown in FIG. 54 are read from the detailed data group 115 and combined. The corresponding five detailed care elements are "Cool the forehead with an ice bag, a cold pack, an ice pillow, or the like", "During cooling, not to cool your limbs", "Be careful not to cool the same region for more than one hour", "Warm your body with bedding or the like. In the case of using electric blanket or hot pillow, be careful not to burn the body", and "If blood flow to legs is poor, be very careful because temperature sensibility may be low". As a result, information obtained by combining the five detailed care elements is visibly output in the detailed description box DBK in the disease-care screen ARi as shown in FIG. 55.

In FIG. 55, one description is formed by combining, in order, the detailed care element of the detailed element specifying number 6 of "Warm your body with bedding or the like. In the case of using electric blanket or hot pillow, be careful not to burn the body", the detailed care element of the detailed element specifying number 7 of "If blood flow to legs is poor, be very careful because temperature sensibility may be low", the detailed care element of the detailed element specifying number 2 of "Cool the forehead with an ice bag, a cold pack, an ice pillow, or the like", the detailed care element of the detailed element specifying number 4 of "During cooling, not to cool your limbs", and the detailed care element of the detailed element specifying number 5 of "Be careful not to cool the same region for more than one hour". With respect to the order of combining two or more detailed care elements, it is sufficient to set priorities and rules and pre-store the setting information in the storing unit 101.

Each of the detailed care elements included in the detailed data group 115 corresponds to elements as a part of the sentences. At the time of combining a plurality of detailed care elements, the plurality of detailed care elements may be filled in a plurality of locations in a predetermined sentence model. A concrete example will be described below.

FIG. 56 is a diagram showing a concrete example of information of the detailed data group 115 in a modification. FIG. 57 is a diagram showing a state where the detailed care elements are visibly output in the detailed description box DBK in the disease-case screen ARi in the modification.

As shown in FIG. 56, the detailed care elements included in the detailed data group 115 are parts constructing a sentence. In a mode, by reading a plurality of detailed care elements (parts) corresponding to a plurality of detailed element specifying numbers included in the symptom-disease-personal information-care-combination information and properly filling them in underlined locations in the sentences shown in FIG. 57, the plurality of detailed care elements are combined and visibly output. Preferably, the detailed data group 115 is properly provided with information indicative of classifications as identification information of locations in predetermined sentence models, in which the detailed care elements are to be filled.

In the foregoing embodiment, one care element is set for a combination of a symptom element, a past disease element, and the like. For example, when there are two or more combinations of symptom elements, there is the possibility that two or more contradictory care elements are detected. For example, a combination of contradictory care elements of "cool" and "warm" may be detected. In such a case, a care element corresponding to one of the two or more combinations of symptom elements may be preferentially employed.

In the foregoing embodiment, in the teaching element associated information 114, detailed item elements of a plurality of caring methods belong to a teaching element of a disease. The invention is not limited to the embodiment. For example, in the teaching element associated information 114, a plurality of teaching elements of a past disease are associated so as to belong to a teaching element of a disease, and a plurality of teaching elements are associated so as to belong to a teaching element of the past disease. When teaching elements of a plurality of caring methods are included in the plurality of teaching elements associated so as to belong to each of the teaching elements of the past disease, the user can learn a caring method of a disease according to the past disease. A concrete example will be described below.

Figure 58:
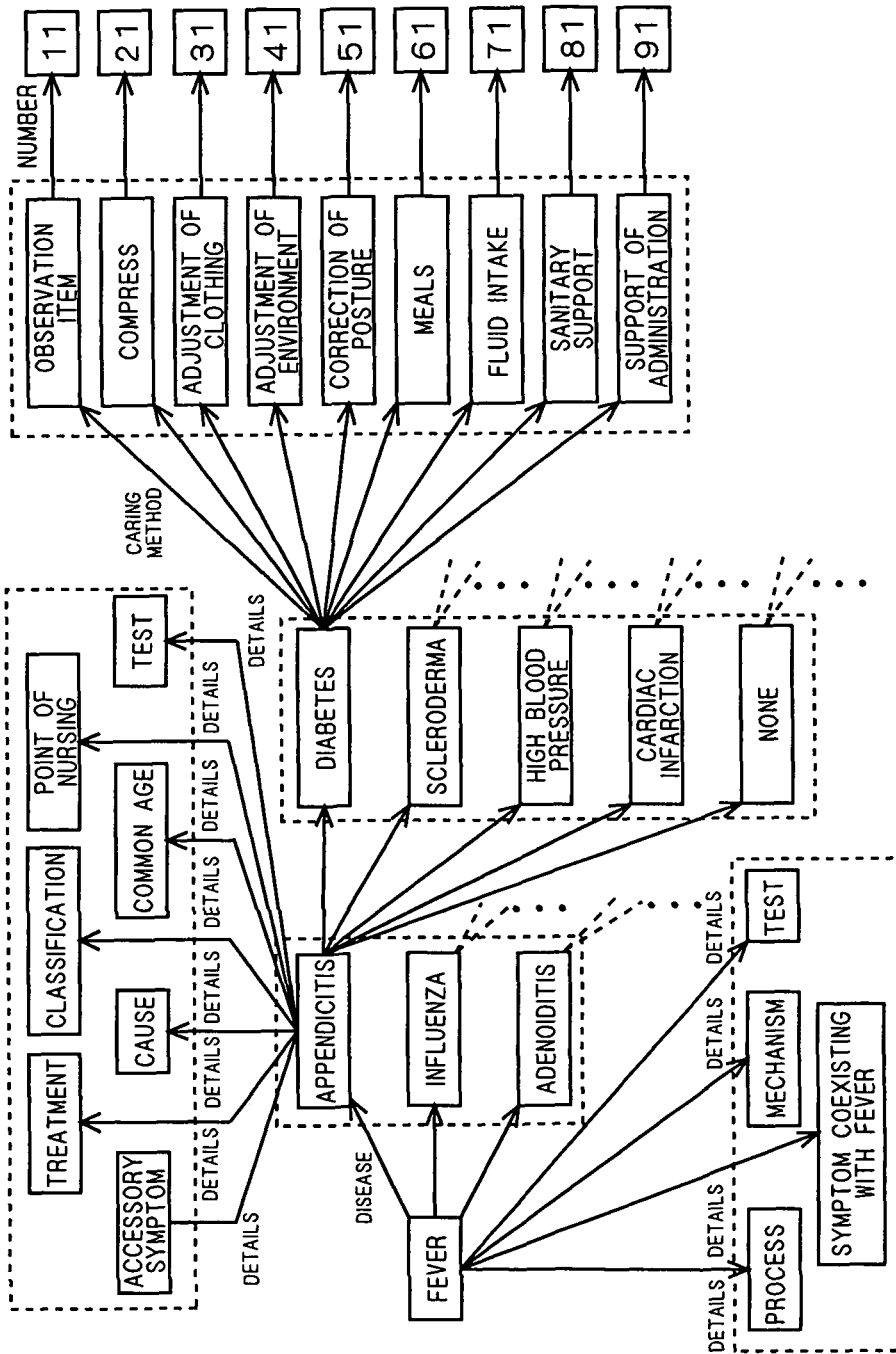
FIG. 58 is a diagram showing a concrete example of teaching element associated information in a modification.

FIG. 58 is a diagram showing a concrete example of the teaching element associated information 114 in a modification. FIG. 59 is a diagram showing a concrete example of information of the detailed data group 115 in the modification. FIG. 58 shows an example in which a plurality of teaching elements of the teaching element "fever" of a symptom are associated.

In the information shown in FIG. 58, detailed item elements "process", "mechanism", "test", and "symptom coexisting with fever" as description of the teaching element "fever" belong to the teaching element "fever" of a symptom. To the teaching element "fever", the teaching elements "appendicitis", "influenza", and "adenoiditis" of diseases developing a symptom of fever belong. In FIG. 58, for convenience of illustration, only the detailed item elements belonging to the teaching element "appendicitis" of a disease are shown as representative examples. The detailed item elements "treatment", "classification", "point of nursing", "accessory symptom", "cause", "common age", and "test" as description of the disease belong to each of the teaching elements "appendicitis", "influenza", and "adenoiditis" of diseases. To each of the teaching elements "appendicitis", "influenza", and "adenoiditis" of diseases, the detailed item elements of the caring methods for the diseases belong via the teaching elements of past diseases.

Concretely, in FIG. 58, for convenience of illustration, only detailed item elements belonging to the teaching element "appendicitis" of a disease are shown as representative examples. To the teaching elements "appendicitis", "influenza", and "adenoiditis" of diseases, the teaching elements "diabetes", "scleroderma", "high blood pressure", "cardiac infarction", and "none" as past diseases belong. Further, in FIG. 58, for convenience of illustration, only the detailed item elements belonging to the teaching element "diabetes" as a past disease are shown as representative examples. To the teaching elements "diabetes", "scleroderma", "high blood pressure", "cardiac infarction", and "none" as past diseases, detailed item elements "observation item", "compress", "adjustment of clothing", "adjustment of environment", "correction of posture", "meals", "fluid intake", "sanitary support", and "support of administration" as caring methods belong. The detailed element specifying numbers "11, 21, 31, 41, 51, 61, 71, 81, and 91" are designated to the detailed item elements "observation item", "compress", "adjustment of clothing", "adjustment of environment", "correction of posture", "meals", "fluid intake", "sanitary support", and "support of administration", respectively.

In the information included in the detailed data group 115 shown in FIG. 59, nine detailed data "be careful with water balance . . . ", "at the time of cooling the femoral region, . . . ", "when sweating, change clothes frequently . . . ", "not to apply stimulus . . . ", "the same body posture for two hours . . . ", "due to fever, energy becomes . . . ", "at the time taking fluid, saccharides . . . ", "to prevent infection . . . ", and "insulin . . . " are associated with the detailed element specifying numbers "11, 21, 31, 41, 51, 61, 71, 81, and 91", respectively.

In the foregoing embodiment, in the learning supporting process, learning information received by the learning information receiving unit 102R is a single teaching element of a disease. The invention is not limited to the embodiment. For example, the learning information may be a plurality of teaching elements including single teaching element of a disease. In such a case, a plurality of teaching elements including a single teaching element of a disease are recognized by the element recognizing unit 102S.

Further, the learning information may be a natural sentence of one or more teaching elements including at least a teaching element of a disease, and the element recognizing unit 102S may recognize a single teaching element of a disease or a plurality of teaching elements including a single teaching element of a disease by a language analyzing process using the analysis data 101a stored in the storing unit 101. Examples of the language analyzing process using the analysis data 101a are a morphological analysis using data for morphological analysis, a dependency structure analysis using data for dependency structure analysis, recognition of a term or paragraph indicative of a disease or the like by using keyword data, and replacement with a representative term such as synonym using dictionary data.

A concrete example will be described with respect to the case where a plurality of teaching elements including a single teaching element of a disease are recognized by the element recognizing unit 102S. It is assumed here that the teaching element associated information 114 has the information shown in FIG. 58, and the detailed data group 115 has the information shown in FIG. 59.

FIG. 60 is a diagram illustrating a personal top screen AEk of the learning support system displayed in the support information display area AE of the learning support screen G11 after log-in in a modification. In the personal top screen AEk, different from the personal top screen AEa shown in FIG. 44, by writing information desired to learn (learning information) in a natural sentence in an upper part of the screen and clicking a search button SB31 with the mouse pointer MP, the learning information written in a natural sentence can be entered. The learning information is received by the learning information receiving unit 102R. The element recognizing unit 102S recognizes one or more teaching elements including a single teaching element of a disease from the learning information written in a natural sentence by the language analyzing process using the analysis data 101a.

For example, in the case where learning information written in a natural sentence such as "I'd like to know the occurrence mechanism of appendicitis" is entered, the teaching element "appendicitis" as a disease and the teaching element "occurrence mechanism" are recognized. In the case where learning information written in a natural sentence such as "caring methods for a diabetic patient having fever due to appendicitis" is entered, the teaching element "fever" related to a symptom, teaching elements "appendicitis" and "diabetes" related to diseases, and an attribute "caring method" are recognized.

Figures 61, 62:
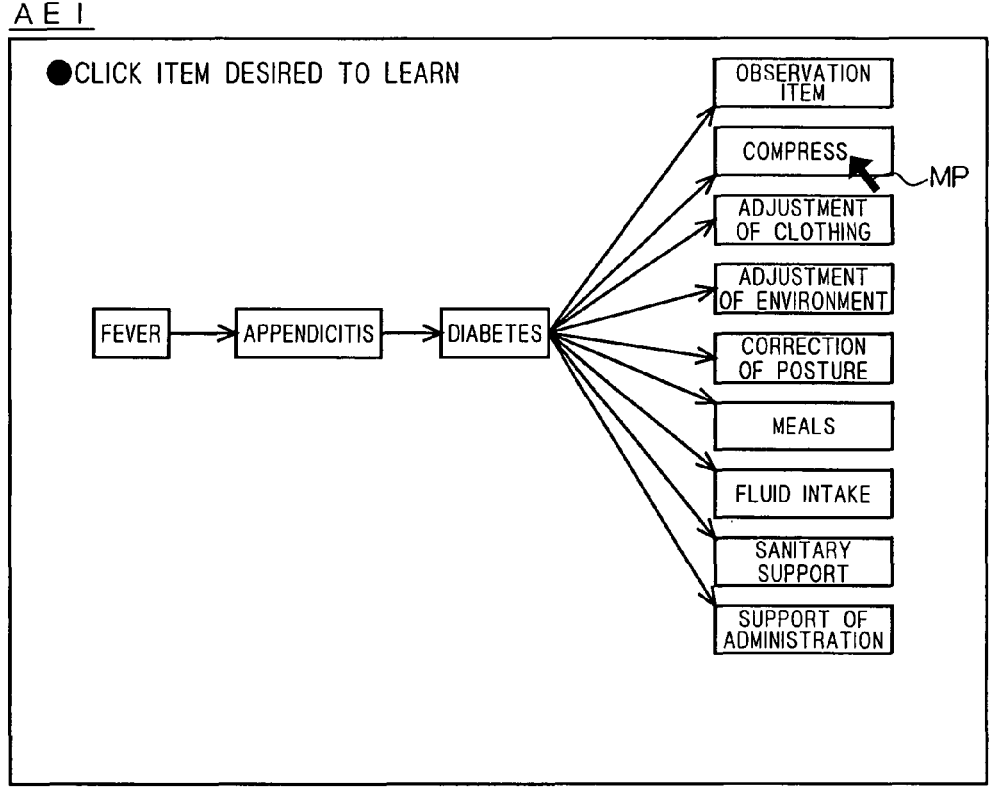
FIG. 61 is a diagram showing a display example of partial element associated information in a modification.
FIG. 62 is a diagram showing a display example of a comment display screen in a modification.

In the cases where the element recognizing unit 102S recognizes the symptom teaching element "fever", disease teaching elements "appendicitis" and "diabetes", and the attribute "caring method", the related information extracting unit 102T extracts partial element associated information including the teaching elements "fever", "appendicitis", and "diabetes" and the attribute "caring method" from the information shown in FIG. 58. FIG. 61 is a diagram showing a network information screen AE1 displayed in the support information display area AE of the learning support screen G11 on the basis of the partial element associated information. In the network information screen AE1, partial element associated information including the teaching elements "fever", "appendicitis", and "diabetes" and the teaching elements of the attribute "caring method" is visibly output in the display unit 13 by the input/output control unit 12A. When a teaching element of a desired caring method is clicked with the mouse pointer MP on the network information screen AE1, the detailed data extracting unit 102U extracts detailed data corresponding to the designated teaching element of the caring method from the information shown in FIG. 59, and the input/output control unit 12A performs display based on the detailed data on the display unit 13. FIG. 62 is a diagram showing a comment display screen AEm displayed in the support information display area AE of the learning support screen G11. In the case where the teaching element "compress" in the partial element associated information which is visibly output as shown in FIG. 61 is designated, the comment display screen AEm as shown in FIG. 62 is displayed in the display unit 13. The comment is for appendicitis accompanying fever and for a compress applied to a diabetic patient.

In such a manner, the user can easily know a concrete caring method for a disease which varies according to symptom and past diseases only by entering information desired to learn in a natural sentence.

In the foregoing embodiment, the data updating unit 102P automatically adds a new care element to the disease-care-combination DB 112 or adds a new teaching element to the teaching element associated information 114. The invention is not limited to the embodiment. For example, by a proper operation on the operation unit 194 of the administrator of the system in the management terminal 190, the data updating unit 102P may add a new care element to the disease-care-combination DB 112 so that the added care element is combined with at least another one element, and add a detailed care element corresponding to the new care element to the detailed data group 115 so that the new care element and the detailed care element are combined with each other. To be concrete, when the number of similar questions is large or an expert thinks it is better to add an element to the disease-care-combination DB 112, on the basis of an input operation on the operation unit 194 in the management terminal 190 of the administrator, the data updating unit 102P may add new combination information of elements belonging to the items in the disease-care-combination DB 112 to the disease-care-combination DB 112. With such a configuration, enrichment of information addressing needs of the user can be achieved.

For example, by a proper operation on the operation unit 194 of the administrator of the system in the management terminal 190, the data updating unit 102P adds a new teaching element to the teaching element associated information 114 so that the teaching element is associated with another one teaching element, adds detailed data corresponding to the new teaching element to the detailed data group 115 so that the new teaching element and the detailed data may be associated with each other. Also in such a mode, enrichment of information addressing needs of the user and the like can be achieved. In particular, by the learning supporting process, the learning information is enriched, and the learning effect can be improved.

In the embodiment, a disease name element included in the disease-symptom-combination DB 111 may include a data element indicative of complication. With such a configuration, from a symptom, not only a so-called disease name but also complication can be also detected. Since a caring method for the complication also exists, the kinds of caring methods visibly presented increase. Therefore, the user can know caring methods more broadly.

In the foregoing embodiment, when a desired care element is designated in the chart PC1 of the disease care information, a detailed care element corresponding to the care element is visibly output. The invention is not limited to the embodiment. By placing the mouse pointer MP on a desired main symptom element displayed on a chart PC2 of the disease name detection route information and clicking the right button of the mouse, detailed information (for example, occurrence mechanism of a symptom) of the designated main symptom element may be visibly output. By properly designating the disease name element PND in the chart PC1 of the disease care information or in the chart PC2 of the disease name detection route information, detailed information (for example, occurrence mechanism of a disease) of the disease name element may be visibly output. In the following, concrete examples of the cases will be described.

First, a concrete example of visibly outputting detailed information of a main symptom element will be described.

The disease-care-combination DB 112 includes detailed element combination information in which one or more detailed care elements of detailed information are combined with each care element. In a similar manner, information (detailed element combination information) obtained by combining each main symptom element with one or more detailed elements (detailed main symptom elements) as detailed information of a main symptom is included in at least one of the disease-symptom-combination DB 111 and the disease-care-combination DB 112. For example, in the detailed element combination information, numbers specifying the detailed main symptom elements (detailed element specifying numbers) are designated. One or more detailed main symptom elements corresponding to each main symptom element are pre-stored in the detailed data group 115. In the detailed data group 115, for example, information is stored in a mode that actual detailed main symptom elements are associated with the detailed element specifying numbers.

When the user operates the operation unit 14 to place the mouse pointer MP on a desired main symptom element included in the chart PC1 or PC2 and performs a predetermined operation (for example, right click) in a state where the chart PC1 of the disease care information or the chart PC2 of the disease name detection route information are visibly output in the display unit 13, the desired one main symptom element is designated in the terminal control unit 12. In response to the designation, the server control unit 102 detects one or more detailed main symptom elements combined with the designated desired main symptom element in the detailed element combination information included in at least one of the disease-symptom-combination DB 111 and the disease-care-combination DB 112. The one or more detailed main symptom elements are read from the detailed data group 15 and transferred to the terminal control unit 12. By the control of the input/output control unit 12A of the terminal control unit 12, detailed information of a main symptom corresponding to the one main symptom element designated by the user is visibly output in the display unit 13 on the basis of the transferred one or more detailed main symptom elements. The detailed information of the main symptom includes, for example, information of the occurrence mechanism of the main symptom. The detailed information is, for example, the sentences shown in FIG. 48.

With such a configuration, when a desired symptom (in this case, a main symptom) is designated from one or more symptoms included in the visibly presented information, detailed information such as information of the occurrence mechanism of the symptom is visibly presented. Therefore, the user can easily obtain the detailed information of a desired symptom according to the situations.

Next, a concrete example of visibly outputting detailed information of a disease name element will be described.

The disease-care-combination DB 112 includes the detailed element combination information obtained by combining each of the care elements with one or more detailed care elements as detailed information. In a similar manner, at least one of the disease-symptom-combination DB 111 and the disease-care-combination DB 112 includes information (detailed element combination information) obtained by combining each of the disease name elements with one or more detailed elements (detailed disease name elements) as detailed information of the disease name. For example, in the detailed element combination information, numbers specifying the detailed disease name elements (detailed element specifying numbers) are designated. One or more detailed disease name elements corresponding to the disease name elements are stored in the detailed data group 115. In the detailed data group 115, for example, information is stored in a mode such that actual disease name detailed elements are associated with the detailed element specifying numbers.

When the user operates the operation unit 14 to place the mouse pointer MP on a desired disease name element included in the chart PC1 or PC2 and performs a predetermined operation (for example, right click) in a state where the chart PC1 of the disease care information or the chart PC2 of the disease name detection route information are visibly output in the display unit 13, the one disease name element is designated in the terminal control unit 12. In response to the designation, the server control unit 102 detects one or more detailed disease name elements combined with the designated one disease name element in the detailed element combination information included in at least one of the disease-symptom-combination DB 111 and the disease-care-combination DB 112. The one or more detailed disease name elements are read from the detailed data group 15 and transferred to the terminal control unit 12. By the control of the input/output control unit 12A of the terminal control unit 12, detailed information of the disease name corresponding to the one disease name element designated by the user is visibly output in the display unit 13 on the basis of the transferred one or more detailed disease name elements. The detailed information of the disease name includes, for example, information of the occurrence mechanism of the disease. The detailed information is, for example, the sentences shown in FIG. 47.

With such a configuration, when a desired disease name is designated in a state where the combination between a disease name according to a symptom and a plurality of cares or combination of one or more symptoms and one disease name with a route of detecting the disease name from the symptom is visibly outputted, detailed information such as information of the occurrence mechanism of the disease is visibly presented for disease name. Therefore, the user can easily obtain the detailed information of a disease name according to the situations.

In the foregoing embodiment, in the nursing supporting process, one or more symptoms are entered by the user. After that, a disease name corresponding to the symptom is detected, and a plurality of cares for the disease name are detected. The invention is not limited to the embodiment. For example, when disease name information of a disease name is entered by the user, a plurality of cares for a disease name element recognized from the disease name information may be detected. With such a configuration, when the user knows the disease name, the user can know caring methods more promptly and easily.

In the foregoing embodiment, one or more teaching elements are recognized by the element recognizing unit 102S in the learning supporting process. The invention is not limited to the embodiment. For example, a keyword indicative of detailed data is given as search metadata to each of the teaching elements included in the teaching element associated information 114. The element recognizing unit 102S recognizes the keyword corresponding to the search metadata. The related information extracting unit 102T extracts partial element associated information including the teaching element to which the search metadata matching with the keyword is given and one or more teaching elements having a predetermined relation with the teaching element.

Although the user enters data by manual operation in the foregoing embodiment, the invention is not limited to the embodiment. For example, voice uttered by the user is received by a microphone, thereby properly entering a symptom, what the user desires to learn, or the like by using sound recognition. That is, it is sufficient to enter information from the user in response to various operations of the user.

In the embodiment, the nursing learning support system 1 is realized by one or more servers 100 and 200, the management terminal 190, and the terminals 10 to 40.

The invention is not limited to the configuration. For example, the functions of the nursing learning support system 1 may be realized by a single computer. In this case, a program for realizing the nursing learning support system 1 can be regarded as one mode.

Although the number of terminals 10 to 40 is four and the number of the hospital server 200 is one in the foregoing embodiment, the invention is not limited to the configuration. The number of the terminals and the number of the hospital servers are arbitrary.

While the invention has been shown and described in detail, the foregoing description is in all aspects illustrative and not restrictive. It is therefore understood that numerous modifications and variations can be devised without departing from the scope of the invention.

What is claimed is:
1. A nursing learning support system comprising:
a first database that stores information obtained by combining each of a plurality of disease name elements with one or more symptom elements, each of said plurality of disease name elements is a first word or first phrase indicating a disease name, and each of said one or more symptom elements is a second word or second phrase indicating a symptom;
a second database that stores information obtained by combining each of said plurality of disease name elements with a plurality of care elements, each of said plurality of care elements is a third word or third phrase indicating a care, wherein said second database includes detailed element combination information that includes first information obtained by combining each of said plurality of care elements with one or more detailed elements each is a fourth word or fourth phrase indicative of information of a caring method, wherein said detailed element combination information includes second information obtained by combining each of said plurality of care elements with one or more personal information elements indicative of personal information and one or more detailed elements, each of which is a fourth word or fourth phrase indicative of information of a caring method;

a nursing learning support system computer server comprising:

a symptom recognizing unit that recognizes one or more symptom elements in response to an input of information from a user;

a disease name detecting unit that detects one disease name element combined with all of one or more symptom elements recognized by said symptom recognizing unit in said first database;

a care detecting unit that detects a plurality of care elements combined with one disease name element detected by said disease name detecting unit in said second database;

a disease care information generating unit that generates disease care information obtained by combining one disease name element detected by said disease name detecting unit with a plurality of care elements detected by said care detecting unit;

an output control unit that receives said disease care information and outputs said disease care information;

a detailed element storing unit that stores one or more detailed elements of each of said plurality of care elements;

a terminal computer comprising:

a care designating unit that designates one of said plurality of care elements included in said disease care information in response to an operation of the user in a state where said disease care information is visibly output in said output device;

wherein said nursing learning support computer server further comprises:

a detailed element detecting unit that detects one or more detailed elements combined with one care element designated by said care designating unit in said detailed element combination information, and on the basis of one or more detailed elements detected by said detailed element detecting unit, said output control unit visibly outputs information of a caring method corresponding to one care element designated by said care designating unit in said output device; and a personal information recognizing unit that recognizes one or more personal information elements indicative of personal information in response to an input of information from the user, and said detailed element detecting unit detects one or more detailed elements combined with both of one care element designated by said care designating unit and one or more personal information elements recognized by said personal information recognizing unit in said detailed element combination information; and a display unit that receives said disease care information from said output control unit and generates a visible image of said disease care information.

2. The nursing learning support system according to claim 1, further comprising a disease name detection route information generating unit that generates disease name detection route information obtained by combining one or more symptom elements recognized by said symptom recognizing unit with one disease name element detected by said disease name detecting unit, wherein said output control unit visibly outputs said disease name detection route information in said output device.

3. The nursing learning support system according to claim 2, wherein said output control unit visibly outputs said disease care information and said disease name detection route information sequentially in order in said output device.

4. The nursing learning support system according to claim 3, wherein said output control unit visibly outputs said disease care information prior to said disease name detection route information in said output device.

5. The nursing learning support system according to claim 2, wherein at least one of said first and second databases includes detailed element combination information obtained by combining each of said plurality of disease name elements with one or more detailed elements each indicative of detailed information of a disease name, said database system further comprises:

a detailed element storing unit that stores one or more detailed elements of each of said plurality of disease name elements;

a disease name designating unit that designates one disease name element included in said disease name detection route information in response to an operation of the user in a state where said disease name detection route information is visibly output in said output device; and a detailed element detecting unit that detects one or more detailed elements combined with one disease name element designated by said disease name designating unit, in said detailed element combination information, wherein said output control unit visibly outputs, in said output device, detailed information of a disease name corresponding to one disease name element designated by said disease name designating unit on the basis of one or more detailed elements detected by said detailed element detecting unit.

6. The nursing learning support system according to claim 5, wherein detailed information of each of said plurality of disease names includes information of occurrence mechanism of a disease.

7. The nursing learning support system according to claim 2, wherein said first database includes detailed element combination information obtained by combining each of said plurality of symptom elements with one or more detailed elements each indicative of detailed information of a symptom, said database system further comprises:

a detailed element storing unit that stores one or more detailed elements of each of said one or more symptom elements;

a symptom designating unit that designates one symptom element included in said disease name detection route information in response to an operation of the user in a state where said disease name detection route information is visibly output in said output device; and a detailed element detecting unit that detects one or more detailed elements combined with one symptom element designated by said symptom designating unit in said detailed element combination information, wherein said output control unit visibly outputs, in said output device, detailed information of a symptom corresponding to one symptom element designated by said symptom designating unit on the basis of one or more detailed elements detected by said detailed element detecting unit.

8. The nursing learning support system according to claim 7, wherein said detailed information of said symptom includes information of occurrence mechanism of a symptom.

9. The nursing learning support system according to claim 1, wherein said second database includes information obtained by combining each of said plurality of disease name elements with a plurality of care elements each indicative of cares at a plurality of levels.

10. The nursing learning support system according to claim 1, further comprising:
a medical record information storing unit that stores electronic medical record information;
an adoption designating unit that designates one care element designated by said care designating unit as one adopted care element adopted by the user in response to an input operation of the user in a state where one or more detailed elements detected by said detailed element detecting unit are visibly output in said output device;
a measurement value obtaining unit that obtains information of a measurement value of a parameter as an index of a health state of a human in response to an input of information from the user; and
a description control unit that controls so as to write, in said electronic medical record information, one or more symptom elements recognized by said symptom recognizing unit, one disease name element detected by said disease name detecting unit, one adopted care element designated by said adoption designating unit, and measurement value information obtained by said measurement value obtaining unit.

11. The nursing learning support system according to claim 1, wherein said detailed element combination information includes information obtained by combining each of said plurality of care elements with at least one symptom element and at least one detailed element, and said detailed element detecting unit detects one or more detailed elements combined with both of one care element designated by said care designating unit and one or more symptom elements recognized by said symptom recognizing unit in said detailed element combination information.

12. The nursing learning support system according to claim 11, further comprising:
an input requesting unit that requests for input of symptom elements in a predetermined number of items;
a third database that stores information obtained by combining each of said plurality of disease name elements with one or more symptom elements of items as part of said predetermined number of items; and
a disease name recognizing unit that recognizes one disease name element indicative of one disease name in response to an input of information from the user, wherein said symptom recognizing unit recognizes one or more symptom elements each combined with one disease name element recognized by said disease name recognizing unit with respect to said part of said predetermined number of items in said third database in response to recognition of one disease name element by said disease name recognizing unit, and said input requesting unit requests for input of symptom elements of the items that remain after said part of said predetermined number of items are excluded from said predetermined number of items.

13. The nursing learning support system according to claim 1, further comprising a disease name recognizing unit that recognizes one disease name element indicative of one disease name in response to an input of information from the user, wherein said care detecting unit detects a plurality of care elements combined with one disease name element recognized by said disease name recognizing unit in said second database.

14. The nursing learning support system according to claim 1, wherein said personal information includes information of past disease.

15. The nursing learning support system according to claim 1, further comprising a personal information database that stores one or more personal information elements and location specifying information specifying location of information so that said one or more personal information elements and said location specifying information are associated with each other, wherein in response to input of said location specifying information from the user, said personal information recognizing unit recognizes one or more personal information elements corresponding to said location specifying information from said personal information database.

16. The nursing learning support system according to claim 1, wherein said personal information includes at least one of information indicating whether a patient takes medicine or not and information indicating whether a patient has allergy or not.

17. The nursing learning support system according to claim 1, wherein said first database includes information obtained by combining each of said plurality of disease name elements with a plurality of symptom elements, said symptom recognizing unit recognizes a plurality of symptom elements indicative of symptoms in response to an input of information from the user, and said disease name detecting unit detects one disease name element combined with all of the plurality of symptom elements recognized by said symptom recognizing unit in said first database.

18. The nursing learning support system according to claim 17, wherein said plurality of symptom elements include one or more symptom elements indicative of accessory symptoms.

19. The nursing learning support system according to claim 17, wherein said plurality of symptom elements include one symptom element indicative of a predetermined symptom and one or more detailed symptom elements indicative of further detailed symptoms of said predetermined symptom.

20. The nursing learning support system according to claim 19, wherein said one or more detailed symptom elements include an element indicative of at least one of a region, degree, period, kind, amount, the number of times, and occurrence timing.

21. The nursing learning support system according to claim 1, wherein said one disease name element includes a disease name element indicative of complication.

22. The nursing learning support system according to claim 1, further comprising:
a data updating unit that adds at least one care element to a plurality of care elements combined with each of said plurality of disease name elements in said second database in response to an input of information from the user.

23. The nursing learning support system according to claim 1, further comprising:
a question information receiving unit that receives question information constructed by a natural sentence in response to an input of information from the user;
a care element recognizing unit that recognizes at least one care element by performing a predetermined language analyzing process on said question information; and
a data updating unit that adds at least one care elements recognized by said care element recognizing unit to a plurality of care elements combined with each of said plurality of disease name elements in said second database.

24. The nursing learning support system according to claim 1, further comprising:
a symptom information receiving unit that receives symptom information indicative of a symptom constructed by a natural sentence in response to an input of information from the user, wherein said symptom recognizing unit recognizes one or more symptom elements by performing a predetermined language analyzing process on said symptom information.

25. The nursing learning support system according to claim 1, wherein at least one of said first and second databases includes detailed element combination information obtained by combining each of said plurality of disease name elements with one or more detailed elements each indicative of detailed information of a disease name, said database system further comprises:
a detailed element storing unit that stores one or more detailed elements of each of said plurality of disease name elements;
a disease name designating unit that designates one disease name element included in said disease care information in response to an operation of the user in a state where said disease care information is visibly output in said output device; and
a detailed element detecting unit that detects one or more detailed elements combined with one disease name element designated by said disease name designating unit, in said detailed element combination information, wherein said output control unit visibly outputs, in said output device, detailed information of a disease name corresponding to one disease name element designated by said disease name designating unit on the basis of one or more detailed elements detected by said detailed element detecting unit.

26. The nursing learning support system according to claim 25, wherein detailed information of each of said plurality of disease names includes information of occurrence mechanism of a disease.

* * * * *

UNITED STATES PATENT AND TRADEMARK OFFICE
CERTIFICATE OF CORRECTION

| | | |
|---|---|---|
| PATENT NO. | : 8,510,125 B2 | Page 1 of 3 |
| APPLICATION NO. | : 11/974968 | |
| DATED | : August 13, 2013 | |
| INVENTOR(S) | : Kosuke Sasai et al. | |

It is certified that error appears in the above-identified patent and that said Letters Patent is hereby corrected as shown below:

In the Claims

In column 56, claim 1, line 46, before "comprising" replace "nursing learning support system" with --database system--.

In column 57, claim 1, line 4, before "computer server" replace "nursing learning support system" with --database system--.

In column 57, claim 1, line 35, before "computer server" replace "nursing learning support" with --database system--.

In column 57, claim 2, line 62, before "according to" replace "nursing learning support system" with --database system--.

In column 58, claim 3, line 4, before "according to" replace "nursing learning support system" with --database system--.

In column 58, claim 4, line 8, before "according to" replace "nursing learning support system" with --database system--.

In column 58, claim 5, line 12, before "according to" replace "nursing learning support system" with --database system--.

In column 58, claim 6, line 37, before "according to" replace "nursing learning support system" with --database system--.

In column 58, claim 7, line 41, before "according to" replace "nursing learning support system" with --database system--.

Signed and Sealed this
Seventh Day of October, 2014

Michelle K. Lee
*Deputy Director of the United States Patent and Trademark Office*

In the Claims (cont'd)

In column 58, claim 8, line 64, before "according to" replace "nursing learning support system" with --database system--.

In column 59, claim 9, line 1, before "according to" replace "nursing learning support system" with --database system--.

In column 59, claim 10, line 6, before "according to" replace "nursing learning support system" with --database system--.

In column 59, claim 11, line 30, before "according to" replace "nursing learning support system" with --database system--.

In column 59, claim 12, line 41, before "according to" replace "nursing learning support system" with --database system--.

In column 59, claim 13, line 63, before "according to" replace "nursing learning support system" with --database system--.

In column 60, claim 14, line 4, before "according to" replace "nursing learning support system" with --database system--.

In column 60, claim 15, line 7, before "according to" replace "nursing learning support system" with --database system--.

In column 60, claim 16, line 19, before "according to" replace "nursing learning support system" with --database system--.

In column 60, claim 17, line 24, before "according to" replace "nursing learning support system" with --database system--.

In column 60, claim 18, line 35, before "according to" replace "nursing learning support system" with --database system--.

In column 60, claim 19, line 39, before "according to" replace "nursing learning support system" with --database system--.

In column 60, claim 20, line 44, before "according to" replace "nursing learning support system" with --database system--.

In column 60, claim 21, line 49, before "according to" replace "nursing learning support system" with --database system--.

CERTIFICATE OF CORRECTION (continued)
U.S. Pat. No. 8,510,125 B2

In the Claims (cont'd)

In column 60, claim 22, line 52, before "according to" replace "nursing learning support system" with --database system--.

In column 60, claim 23, line 58, before "according to" replace "nursing learning support system" with --database system--.

In column 61, claim 24, line 4, before "according to" replace "nursing learning support system" with --database system--.

In column 61, claim 25, line 13, before "according to" replace "nursing learning support system" with --database system--.

In column 62, claim 26, line 17, before "according to" replace "nursing learning support system" with --database system--.